US010111926B2

(12) United States Patent
Eckert et al.

(10) Patent No.: US 10,111,926 B2
(45) Date of Patent: *Oct. 30, 2018

(54) SELECTIVELY TARGETED ANTIMICROBIAL PEPTIDES AND THE USE THEREOF

(71) Applicant: The Regents of the University of California, Oakland, CA (US)

(72) Inventors: Randal H. Eckert, Redondo Beach, CA (US); Daniel K. Yarbrough, Ann Arbor, MI (US); Wenyuan Shi, Los Angeles, CA (US); Maxwell H. Anderson, Sequim, WA (US); Fengxia Qi, Edmond, OK (US); Jian He, Los Angeles, CA (US); Ian H. McHardy, Venice, CA (US)

(73) Assignees: The Regents of the University of California, Oakland, CA (US); C3 Jian, LLC, Marina del Rey, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 15/163,334

(22) Filed: May 24, 2016

(65) Prior Publication Data

US 2016/0331804 A1 Nov. 17, 2016

Related U.S. Application Data

(63) Continuation of application No. 14/178,061, filed on Feb. 11, 2014, now Pat. No. 9,351,490, which is a continuation of application No. 12/938,278, filed on Nov. 2, 2010, now Pat. No. 8,680,058, which is a continuation of application No. 11/851,372, filed on Sep. 6, 2007, now Pat. No. 7,846,895.

(60) Provisional application No. 60/842,871, filed on Sep. 6, 2006.

(51) Int. Cl.
| *C07K 7/06* | (2006.01) |
| *A61K 38/10* | (2006.01) |
| *C07K 7/08* | (2006.01) |
| *C07K 14/315* | (2006.01) |
| *A01N 37/46* | (2006.01) |
| *C07K 14/00* | (2006.01) |
| *A01N 37/18* | (2006.01) |
| *A61K 38/17* | (2006.01) |
| *A61K 47/65* | (2017.01) |
| *A61K 38/00* | (2006.01) |

(52) U.S. Cl.
CPC ............ *A61K 38/10* (2013.01); *A01N 37/18* (2013.01); *A01N 37/46* (2013.01); *A61K 38/1709* (2013.01); *A61K 47/65* (2017.08); *C07K 7/06* (2013.01); *C07K 7/08* (2013.01); *C07K 14/001* (2013.01); *C07K 14/315* (2013.01); *A61K 38/00* (2013.01); *C07K 2319/01* (2013.01)

(58) Field of Classification Search
CPC .......... C07K 7/06; C07K 7/08; C07K 14/001; C07K 14/315
See application file for complete search history.

(56) References Cited

U.S. PATENT DOCUMENTS

| 4,150,116 A | 4/1979 | Taubman et al. |
| 4,250,262 A | 2/1981 | Taubman et al. |
| 4,324,782 A | 4/1982 | Beck |
| 4,442,085 A | 4/1984 | Colman et al. |
| 4,448,768 A | 5/1984 | Colman et al. |
| 4,521,513 A | 6/1985 | Russell |
| 4,671,958 A | 6/1987 | Rodwell et al. |
| 4,693,888 A | 9/1987 | Miyahara et al. |
| 4,725,428 A | 2/1988 | Miyahara et al. |
| 5,057,313 A | 10/1991 | Shih et al. |
| 5,281,524 A | 1/1994 | Horikoshi et al. |
| 5,332,567 A | 7/1994 | Goldenberg |
| 5,352,446 A | 10/1994 | Lehner |
| 5,352,450 A | 10/1994 | Koga et al. |
| 5,439,680 A | 8/1995 | Horikoshi et al. |
| 5,518,721 A | 5/1996 | Lehner et al. |
| 5,612,031 A | 3/1997 | Lehner et al. |
| 5,645,835 A | 7/1997 | Fell, Jr. et al. |
| 5,646,119 A | 7/1997 | Oppenheim et al. |
| 5,672,351 A | 9/1997 | Chikindas et al. |
| 5,686,075 A | 11/1997 | Taubman et al. |
| 5,726,293 A | 3/1998 | Seed |
| 5,851,527 A | 12/1998 | Hansen |

(Continued)

FOREIGN PATENT DOCUMENTS

| CN | 1415301 | 5/2003 |
| EP | 0140498 | 5/1985 |

(Continued)

OTHER PUBLICATIONS

International Search Report dated Sep. 30, 2008, for International Application No. PCT/US07/77795, filed on Sep. 6, 2007, 6 pages.

(Continued)

*Primary Examiner* — Karen Cochrane Carlson
(74) *Attorney, Agent, or Firm* — Gates & Cooper LLP

(57) ABSTRACT

The present invention relates to targeting peptides capable of specifically binding to microbial organisms (e.g., *P. aeruginosa* or *S. mutans*), antimicrobial peptides having antimicrobial activities, and specifically/selectively targeted antimicrobial peptides (STAMPs). In addition, the present invention provides methods of selectively killing or inhibiting microbial organisms by using the peptides or compositions provided by the present invention.

15 Claims, 14 Drawing Sheets

Specification includes a Sequence Listing.

(56) References Cited

U.S. PATENT DOCUMENTS

| | | |
|---|---|---|
| 5,874,068 A | 2/1999 | Engelman et al. |
| 5,875,798 A | 3/1999 | Petrus |
| 5,877,293 A | 3/1999 | Adair et al. |
| 5,891,422 A | 4/1999 | Pan et al. |
| 5,910,573 A | 6/1999 | Pluckthun et al. |
| 5,981,726 A | 11/1999 | Pastan et al. |
| 6,046,037 A | 4/2000 | Hiatt et al. |
| 6,183,744 B1 | 2/2001 | Goldenberg |
| 6,197,299 B1 | 3/2001 | Dohlsten et al. |
| 6,231,857 B1 | 5/2001 | Shi et al. |
| 6,254,856 B1 | 7/2001 | Tsuchiya |
| 6,309,835 B1 | 10/2001 | Iyer et al. |
| 6,346,267 B1 | 2/2002 | Fry et al. |
| 6,492,328 B2 | 12/2002 | Lehrer et al. |
| 6,559,176 B1 | 5/2003 | Bassler et al. |
| 6,673,900 B2 | 1/2004 | Rowe |
| 6,923,962 B2 | 8/2005 | Cvitkovitch et al. |
| 7,071,293 B1 | 7/2006 | Tack et al. |
| 7,087,228 B2 | 8/2006 | Goodman et al. |
| 7,148,404 B2 | 12/2006 | Hogenhaug et al. |
| 7,504,375 B2 | 3/2009 | Hogenhaug et al. |
| 7,556,807 B2 | 7/2009 | Cvitkovitch et al. |
| 7,846,895 B2 | 12/2010 | Eckert et al. |
| 8,680,058 B2 * | 3/2014 | Eckert .................. C07K 7/06 514/2.6 |
| 9,351,490 B2 * | 5/2016 | Eckert .................. C07K 7/06 |
| 2002/0068066 A1 | 6/2002 | Shi et al. |
| 2002/0081302 A1 | 6/2002 | Cvitkovitch et al. |
| 2002/0082195 A1 | 6/2002 | Lehrer et al. |
| 2002/0102316 A1 | 8/2002 | Weissman |
| 2003/0143234 A1 | 7/2003 | Shi et al. |
| 2003/0171421 A1 | 9/2003 | Davies et al. |
| 2003/0186916 A1 | 10/2003 | Yu et al. |
| 2003/0211185 A1 | 11/2003 | Alexis |
| 2003/0228379 A1 | 12/2003 | Shi et al. |
| 2003/0229000 A1 | 12/2003 | Merritt et al. |
| 2004/0023254 A1 | 2/2004 | Fuhrmann et al. |
| 2004/0052814 A1 | 3/2004 | Shi et al. |
| 2004/0137482 A1 | 7/2004 | Eckert et al. |
| 2004/0147595 A1 | 7/2004 | Kjelleberg et al. |
| 2004/0170642 A1 | 9/2004 | Fritiz et al. |
| 2004/0234662 A1 | 11/2004 | Ben-Yehoshua |
| 2005/0152853 A1 | 7/2005 | Huang et al. |
| 2005/0245452 A1 | 11/2005 | Hogenhaug |
| 2005/0250699 A1 | 11/2005 | Hogenhaug et al. |
| 2005/0255128 A1 | 11/2005 | Merritt et al. |
| 2005/0288229 A1 | 12/2005 | Sindrey et al. |
| 2006/0067951 A1 | 3/2006 | Cvitkovitch et al. |
| 2006/0135498 A1 | 6/2006 | Shi et al. |
| 2006/0280780 A1 | 12/2006 | Hogenhaug et al. |
| 2007/0178054 A1 | 8/2007 | Srinivasa et al. |
| 2008/0069782 A1 | 3/2008 | Goodman et al. |
| 2008/0170991 A1 | 7/2008 | Shi et al. |
| 2008/0269122 A1 | 10/2008 | Imboden et al. |
| 2008/0280781 A1 | 11/2008 | Chen et al. |
| 2008/0286210 A1 | 11/2008 | He et al. |
| 2009/0098050 A1 | 4/2009 | Yarbrough et al. |
| 2009/0137481 A1 | 5/2009 | Hogenhaug et al. |
| 2010/0016234 A1 | 1/2010 | Huang et al. |

FOREIGN PATENT DOCUMENTS

| | | |
|---|---|---|
| EP | 0334467 | 9/1989 |
| GB | 2143829 | 2/1985 |
| JP | 52-21571 | 6/1977 |
| JP | 2-177899 | 7/1990 |
| JP | 5-227916 | 9/1993 |
| JP | 6-122633 | 5/1994 |
| JP | 2000-198724 | 7/2000 |
| WO | 92/22653 | 12/1992 |
| WO | 94/09817 | 5/1994 |
| WO | 99/58141 | 11/1994 |
| WO | 00/11037 | 3/2000 |
| WO | 01/85664 | 11/2001 |
| WO | 02/15931 | 2/2002 |
| WO | 02/22686 | 3/2002 |
| WO | 02/102975 | 12/2002 |
| WO | 2004/028519 | 4/2004 |
| WO | 2006/060903 | 6/2006 |
| WO | 2008/151434 | 12/2008 |

OTHER PUBLICATIONS

Joyce, E.A. et al., "Evidence for a Signaling System in Heliobacter pylori: Detection of a luxS-Encoded Autoinducer," Journal of Bacteriology, 2000, vol. 182, No. 13, pp. 3638-3643.

Jun, Z., "Some bioactive substances from plants of West China," Pure & Appl. Chem., 1989, vol. 61, No. 3, pp. 457-460.

Keene, H.J. et al., "Relationship of *Streptococcus mutans* Carrier Status to the Development of Carious Lesions in Initially Cariesfree Recruits," J. Dent. Res., Oct. 1974, vol. 53, No. 5. p. 1295.

Kiyota, T. et al., "Design and Synthesis of Amphiphilic .alpha.-Helical Model Peptides With Systematically Varied Hydrophobic-Hydrophilic Balance and Their Interaction With Lipid- and Bio-Membranes," Biochemistry, 1996, vol. 35, No. 40, pp. 13196-13204.

Kobayashi, I. et al., "Biological Behavior of Human Dental Pulp Cells in Response to Carious Stimuli Analyzed by PCNA Immunostaining and AgNOR Staining," Caries Research, 1996, vol. 30, No. 3, pp. 225-230.

Kolenbrander, P.E. "Oral Microbial Communities: Biofilms, Interactions, and Genetic Systems," Anna. Rev. Microbiol., 2000, vol. 54, pp. 413-437.

Kolenbrander, P.E. et al., "Intergeneric Coaggregation of Oral *Treponema* spp. With *Fusobacterium* spp. and Intrageneric Coaggregation Among *Fusobacterium* spp.," Infection and Immunity, Dec. 1995, vol. 96, No. 12, pp. 4584-4588.

Kuby, J., Immunology, 2nd Edition, W.H. Freeman and Company: New York, NY, 1994, pp. 19-20.

Lee. K.-H., "Development of Short Antimicrobial Peptides Derived From Host Defense Peptides or by Combinatorial Libraries," Current Pharmaceutical Design, 2002, vol. 8, No. 9, pp. 795-813.

Leher, R.I. et al., "Defensins of Vertebrate Animals," Current Opinion in Immunology, 2002, vol. 14, pp. 96-102.

Lehner, T. et al., "A Mechanism of Passive Immunization With Monoclonal Antibodies to a 185,000 M.sub.r Streptococcal Antigen," Advances in Experimental Medicine and Biology (Genetically Engineered Vaccines), 1992, vol. 327, pp. 151-163.

Lehner, T. et al., "Local Passive Immunization by Monoclonal Antibodies Against Streptococcal Antigen I/II in the Prevention of Dental Caries," Infection and Immunity, Dec. 1985, vol. 50, No. 3, pp. 796-799.

Li, P. et al., "An Antimicrobial Peptide Gene Found in the Male Reproductive System of Rats," Science, Mar. 2, 2001, vol. 291, pp. 1783-1785.

Li, Y.H. et al., "Nature Genetic Transformation of *Stretococcus mutans* Growing in Biofilms," J. Bacterial., Feb. 2001, vol. 183, No. 3, pp. 897-908.

Li, Y-H. et al., "A Quorum-Sending System Essential for Induction of Genetic Competence in *Streptococcus mutans* is Involved in Biofilm Formation," Abstracts of the General Meeting of the American Society for Microbiology, May 2001, vol. 101, Abstract No. J-8, p. 442.

Loo, C.Y. et al., "*Streptococcus gordonii* Biofilm Formation: Identification of Genes That Code for Biofilm Phenotypes," Journal of Bacteriology, Mar. 2000, vol. 182, No. 5, pp. 1374-1382.

Lyon, W.R. et al., "Mutation of luxS Affects Growth and Virulence Factor Expression in *Streptococcus pyogenese*," Molecular Microbiology, 2001, vol. 42, No. 1, pp. 145-157.

Ma, J. K-C. et al., "Assembly of Monoclonal Antibodies With IgG1 and IgA Heavy Chain Domains in Transgenic Tobacco Plants," European Journal of Immunology, 1994, vol. 24, No. 1, pp. 131-138.

Ma, J. K-C. et al., "Characterization of a Recombinant Plant Monoclonal Secretory Antibody and Preventive Immunotherapy in Humans," Nature Medicine, May 1998, vol. 4, No. 5, pp. 601-606.

(56) References Cited

OTHER PUBLICATIONS

Ma, J.C.N. et al., "Structure Characterization of Haemostatic Diosgenin Glycosides from Paris Polyohylia," Phytochemistry, 1985, vol. 24, No. 7, pp. 1561-1565.

Ma, J.K-C. et al., "An Investigation Into the Mechanism of Protection by Local Passive Immunization With Monoclonal Antibodies Against *Streptococcis mutans*," Infection and Immunity, Oct. 1990, vol. 58, No. 10, pp. 3407-3414.

Ma, J.K-C. et al., "Use of Monoclonal Antibodies in Local Passive Immunization to Prevent Colonization of Human Teeth by *Streptoccus mutans*," Infection and Immunity, May 1987, vol. 55, No. 5, pp. 1274-1278.

Marshall, S.A. et al., "Spectrum and Antimicrobial Activity of Alexomycin (PNU-82, 127), a Peptide Compound Prejected for Use in Animal Health," Diagn. Microbiol. Infect. Dis., 1999, vol. 33, pp. 181-186.

Mattos-Graner, R.O. et al., "Cloning of the *Streptcpccus mutans* Gene Encoding Glucan Binding Protein B and Analysis of Genetic Diversity and Protein Production in Clinical Isolates," Infection and Immunity, Nov. 2001, vol. 69, No. 11, pp. 6931-6941.

Miyasaki, K.T., et al., ".beta.-Sheet Antibiotic Peptides as Potential Dental Therapeutics," International Journal of Antimicrobial Agents, 1988, vol. 9, pp. 269-280.

Morrison, S.L. et al., "Chimeric Human Antibody Molecules: Mouse Antigen-Binding Domains With Human Constant Region Domains," Proc. Natl. Acad. Sci. USA, Nov. 1984, vol. 81, pp. 6851-6855.

Namba, T. et al., "Chronotropic Effect of the Methanolic Extracts of the Plants of the *Paris* Species and Steroidal Glycosides Isolated from P. vietnamensis on Spontaneous Beating of Myocardial Cells," Planta Medica, 1989, vol. 55, pp. 501-505.

Nicolas, P. et al., "Peptides as Weapons Against Microorganisms in the Chemical Defense System of Vertebrates," Annual Review of Microbiology, 1995, vol. 49, 19 pages.

Parsek, M.R. et al., "Acyl-homoserine Lactone Quorum Sensing in Gram-negative Bacteria: A Signaling Mechanism Involved in Associations With Higher Organisms," PNAS, Aug. 1, 2000, vol. 97, No. 16, pp. 8789-8793.

Penichet, M.L. et al., "Antibody-Cytokine Fusion Proteins for the Therapy of Cancer," Journal of Immunological Methods, 2001, vol. 248, pp. 91-101.

Pratt, L.A. et al., "Genetic Analyses of Bacterial Biofilm Formation," Current Opinion in Microbiology, 1999, vol. 2, pp. 598-603.

Qi, F. et al., "Purification of Mutacin III From Group III *Streptococcus mutans*, UA787 and Genetic Analyses of Mutacin III Biosynthesis Genes," Applied and Environmental Microbiology, Sep. 1999, vol. 65, No. 9, pp. 3880-3887.

Qi, F. et al., "The Group I Strain of *Streptococcus mutans*, UA140, Produces Both the Lantibiotic Mutacin I and a Nonantiobiotic Bacteriocin, Mutacin IV," Applied and Environmental Microbiology, Jan. 2001, vol. 67, No. 1, pp. 15-21.

Qiu, X-Q. et al., "An Engineered Multidomain Bactericidal Peptide as a Model for Targeted Antibiotics Against Specific Bacteria," Nature Biotechnology, Dec. 2003, vol. 21, No. 12, pp. 1480-1485.

Qiu, X-Q. et al., "A Novel Engineered Peptide, a Narrow-Spectrum Antibiotic, is Effective against Vancomycin-Resistant Enterococcus faecalis," Antimicrobial Agents and Chemotherapy, Mar. 2005, vol. 49, No. 3, pp. 1184-1189.

Ruzheinikov, S.N. et al., "The 1.2 .ANG. Structure of a Novel Quorum-Sensing Protein, Bacillus subtilis LuxS," J. Mol. Biol., 2001, vol. 313, pp. 111-122.

Sajjan, U.S. et al., "P-1130, an Antimicrobial Peptide Active against Pseudomonas aeruginosa, Retains Activity in the Presence of Sputum from Cystic Fibrosis Patients," Antimicrobial Agents and Chemotherapy, Dec. 2001, vol. 45, No. 12, pp. 3437-3444.

Sal-Man, N. et al., "Preassembly of Membrane-Active Peptides is an Important Factor in Their Selectivity Toward Target Cells," Biochemistry, 2002, vol. 41, pp. 11921-11930.

Sawai, M.V. et al., "Impact of Single-Residue Mutations on the Structure and Function of Ovispirin/novispirin Antimicrobial Peptides," Protein Engineering, 2002, vol. 15, No. 3, pp. 225-232.

Schauder, S. et al., "The LuxS Family of Bacterial Autoinducers: Biosynthesis of a Novel Quorum-Sensing Signal Molecule," Molecular Microbiology Biology, 2001, vol. 41, No. 2, pp. 463-476.

Schroder, J-M., "Commentary: Epithelial Peptide Antibiotics," Biochemical Pharmacology, 1999, vol. 57, pp. 121-134.

Shai, Y., "Mechanism of the Binding, Insertion and Destabilization of Phospholipid Bilayer Membranes by .alpha.-Helical Antimicrobial and Cell Non-Selective Membrane-Lytic Peptides," Biochimica of Biophysica Acta, 1999, vol. 1462, pp. 55-70.

Shai, Y., "Mode of Action of Membrane Active Antimicrobial Peptides," Biopolymers, 2002, vol. 66, pp. 236-248.

Sharma, A.K. et al., "Transgenic Plants for the Production of Edible Vaccines and Antibodies for Immunotherapy," Current Science, Aug. 25, 1999, vol. 77, No. 4, pp. 524-529.

Shi, W. et al., "Rapid and Quantitative Detection of *Streptococcus mutans* With Species-Specific Monoclonal Antibodies," Hybridoma, 1998, vol. 17, No. 4, pp. 365-374.

Sperandio, V. et al., "Quorum Sensing Controls Expression of the Type III Secretion Gene Transcription and Protein Secretion in Enterohemorrhagic and Enteroptahogenic *Escherichia coli*," PNAS, Dec. 21, 1999, vol. 96, No. 26, pp. 15196-15201.

Stickler, D., "Biofilms," Current Opinion in Microbiology, 1999, vol. 2, pp. 270-275.

Stoodley, P. et al., "Biofilms as Complex Differentiated Communities," Ann. Rev. Microbiol., 2002, vol. 56, pp. 187-209.

Surette, M.G. et al., "Quorum Sensing in *Escherichia coil* and *Salmonella typhimurium*," Proc. Natl. Acad. Sci. USA, Jun. 1998, vol. 95, pp. 7046-7050.

Surette, M.G. et al., "Quorum Sensing in *Escherichia coil, Salmonella typhimuruium*, and *Vibrio harveyi*: A New Family of Genes Responsible for Autoinducing Production," Proc. Natl. Acad. Sci. USA, Feb. 1999, vol. 96, pp. 1639-1644.

Tamamura, H. et al., "Synthesis of Protegrin-Related Peptides and Their Antibacterial and Anti-Human Immunodeficiency Virus Activity," Chem. Pharm. Bull., 1995, vol. 43, No. 5, pp. 853-858.

Tossi, A. et al., "Amphipathic, .alpha.-Helical Antimicrobial Peptides," Biopolymers, 2000, vol. 55, pp. 4-30.

Travis, S.M. et al., "Bactericidal Activity of Mammalian Cathelicidin-Derived Peptides," Infection and Immunity, May 2000, vol. 68, No. 5, pp. 2748-2755.

U.S. Appl. No. 09/378,577, filed Aug. 20, 1999, for Wenyuan Shi et al.

U.S. Appl. No. 12/065,033, filed Feb. 27, 2008, for Daniel K. Yarbrough et al.

Van Raamsdonk, M. et al., "Effect of Antibodies on Chemiluminescence and on Killing of *Streptococcus sobrinus* by Polymorphonuclear Leukocytes," Oral Microbiology and Immunology, 1996, vol. 11, No. 4, pp. 254-258.

Van Raamsdonk, M. et al., "Effect of Monoclonal Antibodies on the Colonization of Rats by *Streptococcus sobrinus*," Caries Research, 1993, vol. 27, pp. 31-37.

Vogel, H.J. et al., "Towards a Structure-Function Analysis of Bovine Lactoferricin and Related Tryptophan- and Arginine-Containing Peptides," Biochem Cell Biol, 2002, vol. 80, pp. 49-63.

Vuong, C. et al., "Impact of the agr Quorum-Sensing System on Adherence to Polystyrene in *Staphylococcus aureus*," The Journal of Infectious Diseases, 2000, vol. 182, pp. 1688-1693.

Walker, C.B., "Microbial effects of mouthrinses containing antimicrobials," J. Clin. Periodontol, 1988, vol. 15, pp. 499-505.

Wei, S-Y. et al., "Solution Structure of a Novel Tryptophan-Rich Peptide With Bidirectional Antimicrobial Activity," Journal of Bacteriology, Jan. 2006, vol. 188, No. 1, pp. 328-334.

Wen, Z.T. et al., "Functional Genomics Approach to Identifying Genes Required to Biofilm Development by *Streptococcus mutans*," Applied and Environmental Microbiology, Mar. 2002, vol. 68, No. 3, pp. 1196-1203.

Wessolowski, A. et al., "Antimicrobial Activity of Arginine- and Trytophan-Rich Hexapeptides: The Effects of Aromatic Clusters, D-Amino Acid Substitution and Cyclization," J. Pept. Res., 2004, vol. 64, pp. 159-169.

(56) References Cited

OTHER PUBLICATIONS

Wimmer, R. et al., "Versatile Interactions of the Antimicrobial Peptide Novispirin With Detergents and Lipids," Biochemistry, 2006, vol. 45, No. 2, pp. 481-497.

Wolinsky, L.E. et al., "The Inhibiting Effect of Aqueous Azradirachta indica (Neem) Extract Upon Bacterial Properties Influencing in vitro Plaque Formation," J. Dent Res., Feb. 1996, vol. 75, No. 2, pp. 816-822.

Yasin, B. et al., "Susceptibility of Chlamydia trachomatis serovars L2, D, and E to G-10 novispirin," Database Biosis Biosciences Information Service: Philadelphia, PA, 2001, 2 pages.

Yoshida, A. et al., "Role of the *Streptococcus mutans* luxS Gene in Biofilm Formation," Abstracts of the General Meeting of the American Society for Microbiology, May 2002, vol. 102, Abstract No. D. 27, p. 161.

Yoshida, A. et al., "Molecular Analysis of the *Streptococcus mutans* Genes Involved in Biofilm Formation," Abstracts of the General Meeting of the American Society for Microbiology, May 2001, vol. 101, Abstract No. D. 242, pp. 326-327.

Zhang, L. et al., "Antimicrobial Peptide Therapectics for Cystic Fibrosis," Antimicrobial Agents and Chemotherapy, Jul. 2005, vol. 49, No. 7, pp. 2921-2927.

Breukink et al., "Use of the Cell Wall Precursor Lipid II by a Pore-Forming Peptide Antibiotic". Science, Dec. 17, 1999, vol. 286, pp. 2361-2364.

Database Entrez: Ajdic et al., "Hypothetical protein SMU. 1903c (*Streptococcus mutans* UA159)". Proc. Natl. Acad. Sci. U.S.A., 1999, vol. 22, pp. 14434-14439, Database Accession NP_722209, Sep. 10, 2004, 1 page.

Eckert et al., "Adding Selectivity to Antimicrobial Peptides: Rational Design of a Multidomain Peptide against *Pseudomonas* spp.," Antimicrobial Agents and Chemotherapy, Apr. 2006, vol. 50, No. 4, pp. 1480-1488.

Eckert et al., "Enhancement of Antimicrobial Activity Against Pseudomonas aeruginosa by Coadministration of G10KHc and Tobramycin". Antimicrobial Agents and Chemotherapy, Nov. 2006, vol. 50, No. 11, pp. 3833-3838.

Eckert et al., "Targeted Killing of *Streptococcus mutans* by a Pheromone-Guided "Smart" Antimicrobial Peptide". Antimicrobial Agents and Chemotherapy, Nov. 2006, vol. 50, No. 11, pp. 3651-3657.

Eckert et al., "Stability and Activity in Sputum of G10KHc, a Potent Anti-Pseudomonas Antimicrobial Peptide". Chem Biol. Drug Des., 2007, vol. 70, pp. 456-460.

Qi et al., "Peptide pheromone induced cell death of *Sreptococcus mutans*", FEMS Microbiology Letters, vol. 251, 2005, pp. 321-326.

Sawai et al., "Impact of Single-residue mutations on the structure and function of ovispirin/novispirin antimicrobial peptides". Protein Engineering, 2002, vol. 15, No. 3, pp. 225-232.

Steinstraesser et al., "Activity of Novispirin G10 against Pseudomonas aeruginosa In Vitro and in Infected Burns". Antimicrobial Agents and Chemotherapy, Jun. 2002, vol. 46, No. 6, pp. 1837-1844.

Australian Office Action for Australian application No. 2007292221 filed on Sep. 6, 2007.

Supplementary European Search Report dated Mar. 31, 2010, for EP application No. 078419999.1, 3 pages.

Arakawa, T. et al., "Plants Are Not just Passive Creatures!" Nature Medicine, May 1998, vol. 4, No. 5, pp. 550-551.

Axelsson, P. et al., "Efficacy of mouthrinses in inhibiting dental plaque and gingivitis in man," J. Clin. Periodontal, 1987, vol. 14, pp. 205-212.

Barbeau, J. et al., "Biofilms, Infectious Agents, and Dental Unit Waterlines: A Review," Can. J. Microbial., 1998, vol. 44, pp. 1019-1028.

Bassler, B.L., "How Bacteria Talk to Each Other: Regulation of Gene Expression by Quorum Sensing," Current Opinion in Microbiology, 1999, vol. 2, pp. 582-587.

Bhagwat, S.P. et al., "Effects of Mutating Putatuve Two-Component Systems on Biofilm Formation by *Streptococcus mutans* UA159," FEMS Microbiology Letters, 2001, vol. 205, pp. 225-230.

Blondelle, S.E. et al., "Combinatorial Libraries: A Tool to Design Antimicrobial and Antifungal Peptide Analogues Having Lytic Specificities for Structure-Activity Relationship Studies," Biopolymers, 2000, vol. 55, pp. 74-87.

Bowie, J.U. et al., "Deciphering the Message in Protein sequences: tolerance to Amino Acid Substitutions," Science, Mar. 6, 1990, vol. 247, pp. 1306-1310.

Brogden, K.A. et al., "Antimicrobial Peptides in Animals and Their Role in Host Defences," International Journal of Antimicrobial Agents, 2003, vol. 22, pp. 465-478.

Brogden, K.A., "Antimicrobial Peptides: Pore Formers or Metabolic Inhibitors in Bacteria?" Nature Reviews Microbiology, Mar. 2005, vol. 3, pp. 238-250.

Chen, P. et al., "The Specific Genes for Lantobiotic Mutacin II Biosynthesis in *Streptococcus mutans*, T8 are Clustered and Can be Transferred en Bloc," Applied and Environmental Microbiology, Mar. 1999, vol. 65, No. 3, pp. 1356-1360.

Chen, X. et al., "Structural Identification of a Bacterial Quorum-Sensing Signal Containing Boron," Nature, Jan. 31, 2002, vol. 415, pp. 545-549.

Hung, W.O. et al., "Signaling Systems in Porphyromonas gingivalis Based on a LuxS Protein," Journal of Bacteriology, Jul. 2001, vol. 183, No. 13, pp. 3903-3909.

Davey, M.E. et al., "Microbial Biofilms: Form Ecology to Molecular Genetics," Microbiology and Molecular Biology Reviews, Dec. 2000, vol. 64, No. 4, pp. 847-867.

Davies, D.G. et al., "The Involvement of Cell-to-Cell Signals in the Development of a Bacterial Biofilm," Science, Apr. 10, 1998, vol. 280, pp. 295-298.

Day W.A., Jr. et al., "Shigella flexneri LuxS Quorum-Sensing System Modulates virB Expression but is Not Essential for Virulence," Infection and Immunity, Jan. 2001, vol. 69, No. 1, pp. 15-23.

Deng, S. et al., "Synthesis of three diosgenyl saponins: dioscin, polyphyllin D, and balanitin 7," Carbohydrate Research, 1999, vol. 317, pp. 53-62.

Deslouches, B. et al., "De Novo Generation of Cationic Antimicrobial Peptides: Influence of Length and Tryptophan Substitution on Antimicrobial Activity," Antimicrobial Agents and Chemotherapy, Jan. 2005, vol. 49, No. 1, pp. 316-322.

Diamond, G., "Nature's Antibiotics: The Potential of Antimicrobial Peptides as New Drugs," Biologist, 2001, vol. 48, No. 5, pp. 209-212.

Dunny, G.M. et al., "Cell-Cell Communication in Gram-Positive Bacteria," Annu. Rev. Microbiol., 1997, vol. 51, pp. 527-564.

Eckert, R. et al., "Adding Selectivity to Antimicrobial Peptides: Rational Design of a Multidomain Peptide against *Pseudomonas* spp.," Antimicrobial Agents and Chemotherapy, Apr. 2006, vol. 50, No. 4, pp. 1480-1488.

Everhart, D.L. et al., "Dental Caries Vaccine: Some Problems Solved?" Microbiological Sciences, 1985, vol. 2, No. 10, pp. 312-313.

Fong, K.P. et al., "Intra- and Interspecies Regulation of Gene Expression by Actinobacillus actinomycetemcomitans LuxS," Infection and Immunity, Dec. 2001, vol. 69, No. 12, pp. 7625-7634.

Forsyth, M.H. et al., "Intercellular Communication in Heliobacter pylori: luxS is Essential for the Production of an Extracellular Signaling Molecule," Infection and Immunity, Jun. 2000, vol. 68, No. 6, pp. 3193-3199.

Fortney, K. et al., "Haemophilus ducreyi is Susceptible to Protegrin," Antimicrobial Agents and Chemotherapy, Oct. 1998, vol. 42, No. 10, pp. 2690-2693.

Frias, J. et al., "Periodontal Pathogens Produce Quorum Sensing Signal Molecules," Infection and Immunity, May 2001, vol. 69, No. 5, pp. 3431-3434.

Fuqua, C. et al., "Self Perception in Bacteria: Quorum Sensing With Acylated Homoserine Lactones," Current Opinion in Microbiology, 1998, vol. 1, pp. 183-189.

Ganz, T. et al., "Antimicrobial Peptides in Innate Immunity," Chapter 11 in Development of Novel Antimicrobial Agents: Emerging Strategies, 2001, Horizon Scientific Press: Wymondham, England, pp. 139-147.

(56) References Cited

OTHER PUBLICATIONS

Gao, H. et al., "Hydrophobic Contribution Constants of Amino Acid Residues to the Hydrophobicities of Oligopeptides," Pharmaceutical Research, 1995, vol. 12, No. 9, pp. 1279-1283.

Gazi, M.I., "Monoclonal Antibodies in Dentistry," British Dental Journal, Dec. 6, 1986, vol. 161, No. 11, pp. 399-405.

Giacometti, A. et al., "Antimicrobial Activity of Polycationic Peptides," Peptides, 1999, vol. 20, pp. 1265-1273.

Greenspan, N.S. et al., "Defining Epitopes: Its Not Easy as it Seems," Nature Biotechnology, Oct. 1999, vol. 17, pp. 936-937.

Grigoriev, P.A. et al., "Differences in Membrane Pore Formation by Peptaibols," Journal of Peptide Science, 2003, vol. 9, pp. 763-768.

Groenink, J. et al., "Cationic Amphipathic Peptides, Derived From Bovine and Human Lactoferrins, With Antimicrobial Activity Against Oral Pathogens," FEMS Microbiology Letters, 1999, vol. 179, pp. 217-222.

Hancock, R.E.W., "Cationic Peptides: Effectors in Innate Immunity and Novel Antimicrobials," The Lancet Infectious Diseases, Oct. 2001, vol. 1, pp. 156-164.

Hazlett, K.R.O. et al., "Inactivation of the gbpA Gene of *Streptococcus mutans* Alters Structural and Functional Aspects of Plaque Biofilm Which Are Compensated by Recombincation of the gtfB and gtfC Genes," Infection and Immunity, Aug. 1999, vol. 67, No. 8, pp. 3909-3914.

Helmerhost, E.J. et al., "Synthetic Histatin Analogues With Broad-Spectrum Antimicrobial Activity," Biochem. J., 1997, vol. 326, pp. 39-45.

Hong, S:Y. et al., "The Effect of Charge Increase on the Specificity and Activity of a Short Antimicrobial Peptide," Peptides, 2001, vol. 22, pp. 1669-1674.

Huang, H.W. et al., "Molecular Mechanism of Peptide-Induced Pores in Membranes," Physical Review Letters, May 14, 2004, vol. 92, No. 19, pp. 198304-1-198304-4.

Huber, B. et al., "The Cep Quorum-Sensing System of Burkholderia cepacia H111 Controls Biofilm Formation and Swarming Motility," Microbiology, 2001, vol. 147, pp. 2517-2528.

\* cited by examiner

SELECTIVELY TARGETED ANTIMICROBIAL PEPTIDES AND THE USE THEREOF

CROSS REFERENCE TO RELATED APPLICATIONS

This application is a Continuation of U.S. patent Ser. No. 14/178,061, filed on Feb. 11, 2014, now U.S. Pat. No. 9,351,490, issued on May 31, 2016, which is a Continuation of U.S. patent application Ser. No. 12/938,278, filed on Nov. 2, 2010, now U.S. Pat. No. 8,680,058, issued on Mar. 25, 2014, which is a Continuation of U.S. patent application Ser. No. 11/851,372, filed on Sep. 6, 2007, now U.S. Pat. No. 7,846,895, issued on Dec. 7, 2010, which claims priority to U.S. Provisional Application No. 60/842,871 filed on Sep. 6, 2006, all of which are incorporated herein by reference.

FIELD OF INVENTION

The present invention relates to the field of antimicrobial compositions and treatment.

BACKGROUND OF THE INVENTION

The indigenous microflora found at human mucosal surfaces are critical for acquiring nutrients and providing protective colonization against pathogenic microorganisms. When the normal flora are disrupted by any number of factors, the result is often microbial infections at the mucosal surface, many of which affect populations worldwide. The lack of a robust immune response at mucosal surfaces has limited the prescribing clinician to conventional antibiotics or antimicrobials for treatment of mucosal infections. Unfortunately for the normal flora, most small molecule antibiotics have broad spectrum of activity, killing benign and pathogenic organisms indiscriminately. This effect often leads to severe antibiotic associated infections due to the vacated niche available for pathogen colonization. *Clostridium difficile, Candida albicans* and *Staphylococcus aureus* are examples of classical opportunistic pathogens that take advantage of increased niche size after antibiotic treatment. The problems resulting from wide-spectrum antibiotic use, combined with the emergence of drug-resistant strains, highlight the fundamental need for new "targeted" antibiotic therapies to combat mucosal pathogens with a minimal impact on normal microflora.

Previous efforts toward achieving target-specific antimicrobial therapy consisted of conjugating antibiotics to monoclonal antibodies or constructing large fusion proteins with bactericidal and bacterial recognition domains (Qiu et al., 2005). Neither method has yet to result in functional, effective therapeutics due to the low efficiency of chemical conjugation, instability of large proteins, or high cost of production.

Although G10KHc, a specifically targeted antimicrobial peptide (STAMP), has been developed and demonstrated increased killing potency, selectivity and kinetics against targeted bacteria (Eckert et al., 2006), there is a need to develop novel STAMPs that are capable of specifically or selectively killing or inhibiting the growth of undesirable target microorganisms.

SUMMARY OF THE INVENTION

One aspect of the present invention relates to a selectively/specifically targeted antimicrobial peptide (STAMP) which comprises a targeting peptide and an antimicrobial peptide. The STAMP further comprises a linker peptide.

In one embodiment, the targeting peptide is selected from the group consisting of C16 or $CSP_{C16}$ (TFFRLFNRS-FTQALGK, SEQ ID NO. 2), M8 or $CSP_{M8}$ (TFFRLFNR, SEQ ID NO 5), and peptide 1903 (NIFEYFLE, SEQ ID NO 10).

In another embodiment, the linker peptide is selected from the group consisting of GGG (SEQ ID NO 17), AAA (SEQ ID NO 18), SAT (SEQ ID NO 19), ASA (SEQ ID NO 20), SGG (SEQ ID NO 21), PYP (SEQ ID NO 22), SGS (SEQ ID NO 23), GGS (SEQ ID NO 24), SPS (SEQ ID NO 25), PSGSP (SEQ ID NO 26), PSPSP (SEQ ID NO 27), GGSGGS (SEQ ID NO 28) or a combination (a multimer) of any two (dimer), three (timer), four (tetramer), five (pentamer) or more than five thereof.

In another embodiment, the antimicrobial peptide is selected from the group consisting of G2 (a derivative of novispirin G10, KNLRRIIRKGIHIIKKY* as shown in SEQ ID NO 3) (* denotes C-terminal amidation), S6L3-33 having an amino acid sequence of FKKFWKWFRRF (SEQ ID NO 7) and BD2.21 having an amino acid sequence of KLFK-FLRKHLL (SEQ ID NO 11).

In another embodiment, the STAMP comprises a targeting peptide and an antimicrobial peptide, wherein the targeting peptide is covalently linked to the antimicrobial peptide via a peptide bond, wherein the targeting peptide is selected from the group consisting of C16 (SEQ ID NO 2), M8 (SEQ ID NO 5), and 1903 (SEQ ID NO 10); and wherein the antimicrobial peptide is selected from the group consisting of G2 (SEQ ID NO 3), S6L3-33 (SEQ ID NO 7) and BD2.21 (SEQ ID NO 11).

In another embodiment, the STAMP comprises a targeting peptide which is covalently linked to a linker peptide via a peptide bond and an antimicrobial peptide which is covalently linked to the linker peptide via a peptide bond, wherein the targeting peptide is selected from the group consisting of C16 (SEQ ID NO 2), M8 (SEQ ID NO 5), and 1903 (SEQ ID NO 10); wherein the antimicrobial peptide is selected from the group consisting of G2 (SEQ ID NO 3), S6L3-33 (SEQ ID NO 7) and BD2.21 (SEQ ID NO 11); and wherein the peptide linker is selected from the group consisting of GGG (SEQ ID NO 17), AAA (SEQ ID NO 18), SAT (SEQ ID NO 19), ASA (SEQ ID NO 20), SGG (SEQ ID NO 21), PYP (SEQ ID NO 22), SGS (SEQ ID NO 23), GGS (SEQ ID NO 24), SPS(SEQ ID NO 25), PSGSP (SEQ ID NO 26), PSPSP (SEQ ID NO 27), and GGSGGS (SEQ ID NO 28).

In another embodiment, the STAMP is selected from the group consisting of C16G2 (SEQ ID NO. 4); C16-33 (SEQ ID NO. 8); C16-BD2.21 (SEQ ID NO. 14); M8G2 (SEQ ID NO. 15); M8-33 (SEQ ID NO. 9); M8-BD2.21 (SEQ ID NO. 6); 1903-G2 (SEQ ID NO. 12); 1903-33 (SEQ ID NO. 16); and 1903-BD2.21 (SEQ ID NO. 13).

In another embodiment, the amino acids in the STAMP are D-amino acid enantiomer.

Another aspect of the present invention relates to a STAMP composition comprising a STAMP and an antibiotic, wherein the STAMP composition shows a synergistic antimicrobial effect in killing or reducing the growth of a target microbial organism. In one embodiment, the STAMP is G10KHc (SEQ ID NO 36). In another embodiment, the antibiotic is tobramycin. In a preferred embodiment, the STAMP composition comprises G10KHc (SEQ ID NO 36) and tobramycin.

Another aspect of the present invention relates to a STAMP composition comprising a STAMP and an agent which can enhance, maintain, or facilitate the function or activity of the STAMP. In one embodiment, the agent is a protease inhibitor or rhDNase. In a preferred embodiment, the STAMP composition comprises G10KHc (SEQ ID NO 36) and a protease inhibitor and/or rhDNase.

Another aspect of the present invention is a diagnostic agent comprising a targeting peptide and a detectable agent. In one embodiment, the targeting peptide is conjugated to the detectable agent.

Another aspect of the present invention relates to the use of a composition of the present invention (e.g., the STAMP or the STAMP composition) in selectively killing, inhibiting or reducing the growth of a target microbial organism in a subject or on a biofilm or treating a disease associated with a target microbial organism.

* indicates that the number of cfu/mL from G10KHc/tobramycin treated cultures was too small to appear on the log scale.

Figure 10:
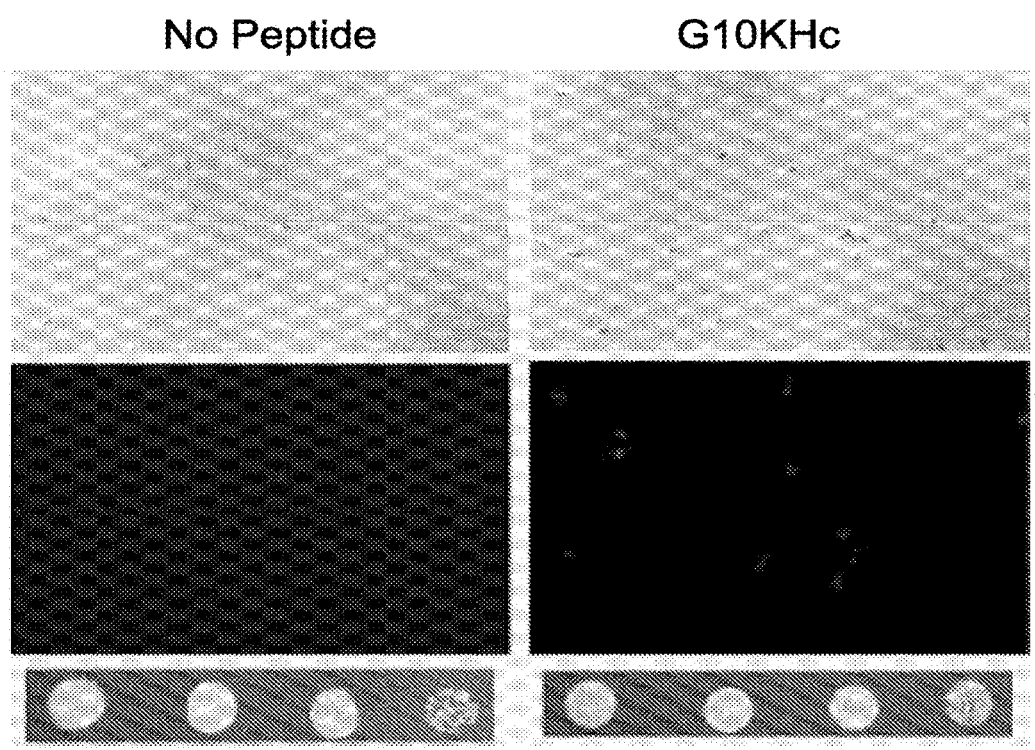

FIG. 10: Dye uptake mediated by sub-inhibitory concentrations of G10KHc. (a) *P. aeruginosa* were treated with medium (left column) or 2 μM G10KHc (right column) for 5 min followed by PI dye addition. Bright-field (upper panel) and fluorescence (lower panel) images of the same field were collected and evaluated for intracellular dye accumulation (red fluorescence). (b) Surviving cfu/mL from untreated (dye only) and G10KHc-treated cultures were quantitated after visualization and plated as 5-fold serial dilution.

Figure 11:
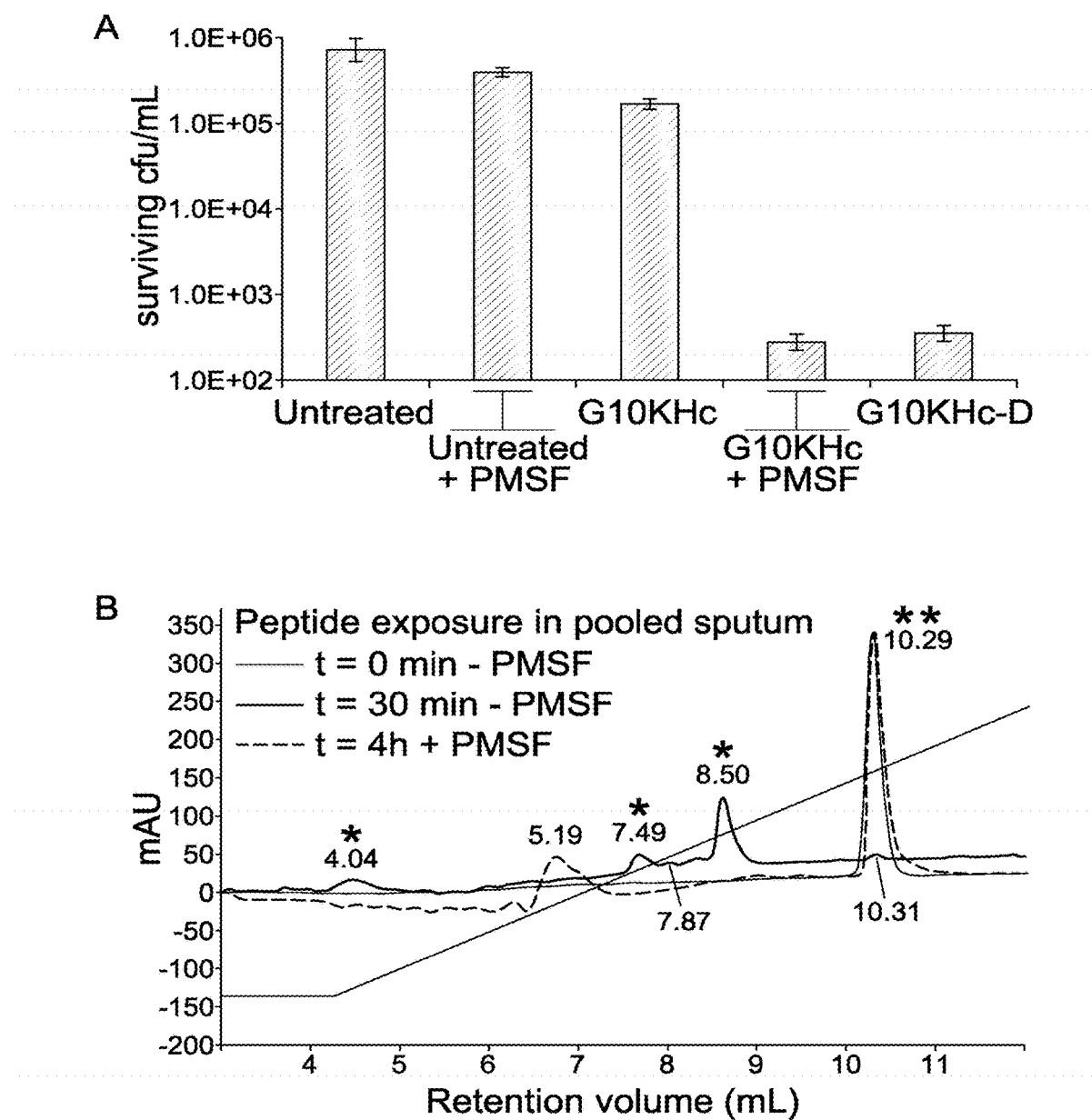

FIG. 11: Activity and stability of G10KHc and G10KHc-D in sputum. (A) Exogenously added *P. aeruginosa* were challenged with 25 μM G10KHc (with or without PMSF), 25 μM G10KHc-D, or left untreated (specified in the figure), and the surviving cfu/mL rescued and quantitated 4 h after agent addition. Rescued cfu/mL were expressed as the average of three independent experiments with standard deviations. (B) G10KHc (with and without PMSF, specified in the figure) was added to sputum for specific durations and peptide stability (milli-absorbance units, mAU) was monitored by HPLC. The increasing mobile phase linear gradient is shown in black. (**) Intact G10KHc identified by MALDI mass spectrometry at retention volume 10.29 mL. (*) Fractions collected for antimicrobial analysis (Table 1).

Figure 12:
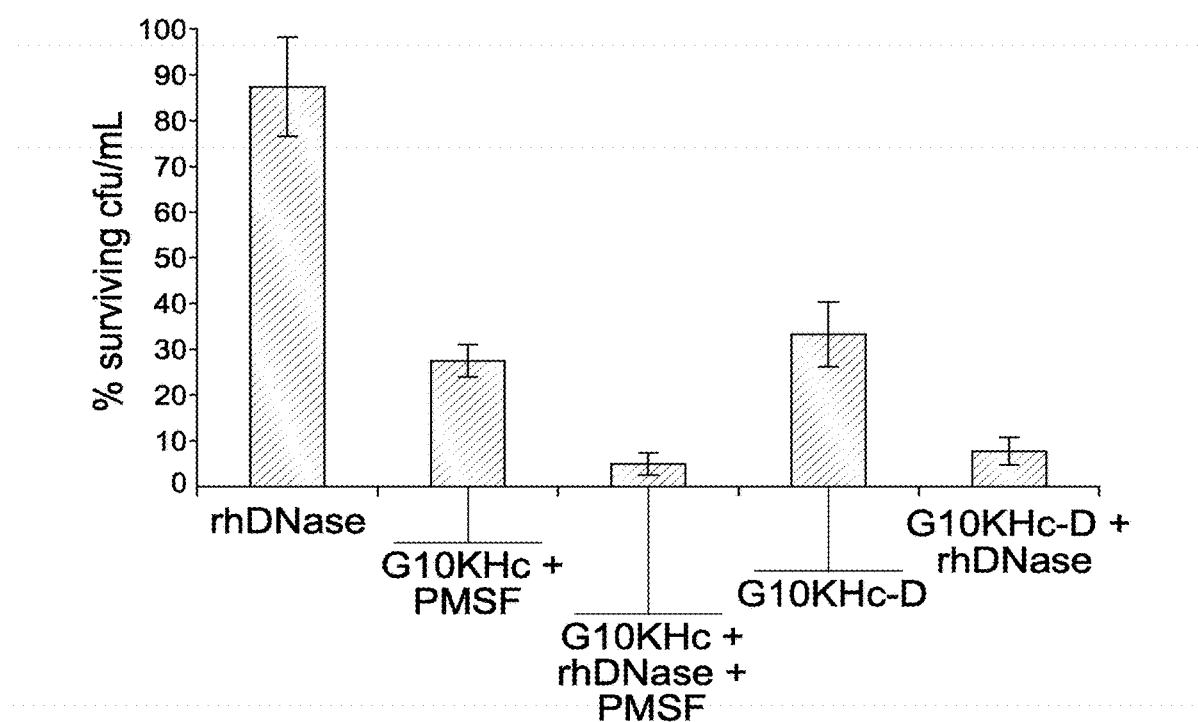

FIG. 12: Effect of rhDNase on G10KHc and G10KHc-D activity in concentrated sputum. Minimally diluted pooled sputum samples with exogenously added *P. aeruginosa* were treated with 25 μM G10KHc (with PMSF) or 50 μM G10KHc-D for 1 h after pretreatment with or without rhDNase. Rescued cells were quantitated and expressed as the percentage of input cfu/mL. The data represent the average of at least 3 independent experiments with standard deviation.

Figure 13:
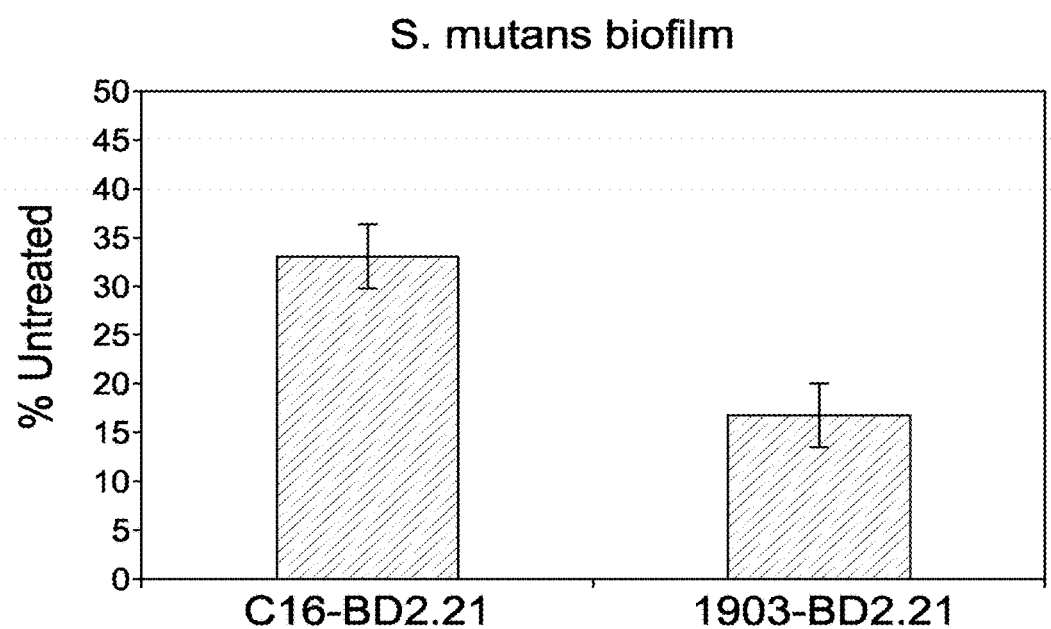

FIG. 13: Killing of single-species *Streptococcus mutans* mature biofilms with C16-BD2.21 and 1903-BD2.21. The figure indicates that C16-BD2.21 and 1903-BD2.21 can kill 33% and 15% of the viable *S. mutans* within the mature biofilm (grown 18-24 h) respectively, after the biofilm was treated by the peptides for only 20 min.

Figure 14:
Figure 14:
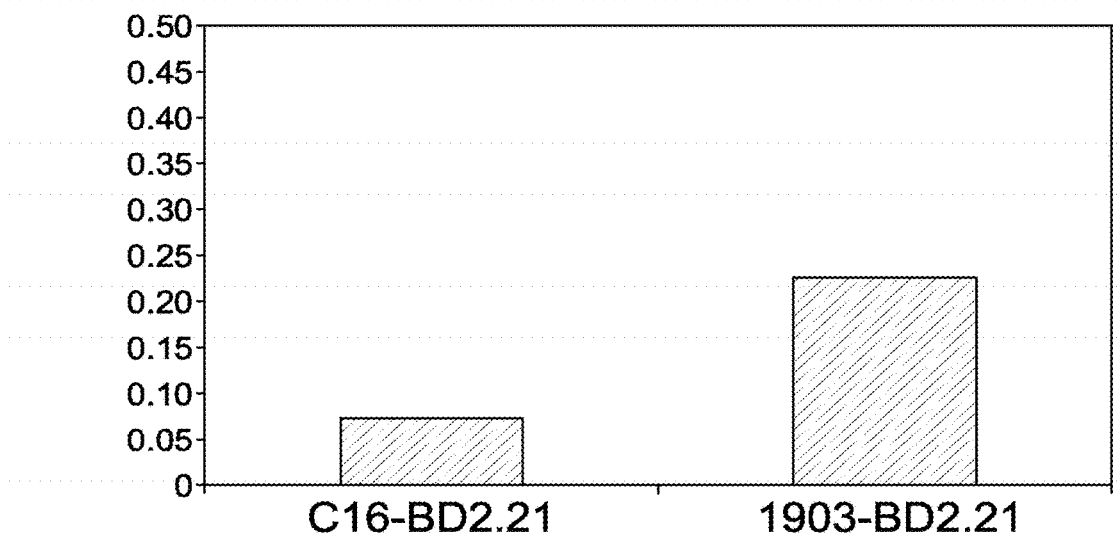

FIG. 14: Impact of C16-BD2.21 and 1903-BD2.21 on multi-species biofilm of oral Streptococci. (A) shows that C16-BD2.21 has no impact on the total cfu/mL population and 1903-BD2.21 reduced total population by about 30%. (B) shows that ratio of surviving *S. mutans* to total Streptococci was 0.075 under C16-BD2.21 treatment and the ratio was about 0.2 under 1903-BD2.21 treatment.

DETAILED DESCRIPTION OF PREFERRED EMBODIMENTS

One aspect of the present invention relates to selectively/specifically targeted antimicrobial peptides (STAMPs) and the use thereof.

The term "selectively/specifically targeted antimicrobial peptide" or "STAMP" refers to a chimeric polypeptide which comprises a targeting peptide and an antimicrobial peptide, wherein the targeting peptide is covalently linked or conjugated (e.g., via a peptide bond) to the antimicrobial peptide either at the C-terminal or N-terminal of the targeting peptide. For example, one STAMP may comprise one of the following two structures: 1) a targeting peptide with its C-terminal covalently linked to the N-terminal of an antimicrobial peptide [Amino terminus-targeting peptide-peptide bond-antimicrobial peptide-carboxyl terminus], and 2) an antimicrobial peptide with its C-terminal covalently linked to the N-terminal of a targeting peptide [Amino terminus-antimicrobial peptide-peptide bond-targeting peptide-carboxyl terminus].

In one embodiment of the present invention, the STAMP further comprises a peptide linker by which the targeting peptide is covalently linked or conjugated to the antimicrobial peptide. In this case, a STAMP may comprise one of the following two structures: 1) a targeting peptide with its C-terminal covalently linked to the N-terminal of a linker peptide and an antimicrobial peptide with its N-terminal covalently linked to the C-terminal of the linker peptide (Amino terminus-targeting peptide-peptide bond-linker peptide-antimicrobial peptide-peptide bond-carboxyl terminus) and 2) a targeting peptide with its N-terminal covalently linked to the C-terminal of a linker peptide and an antimicrobial peptide with its C-terminal covalently linked to the N-terminal of the linker peptide (Amino terminus-antimicrobial peptide-peptide bond-linker peptide-peptide bond-targeting peptide-carboxyl terminus).

According to the present invention, a targeting peptide can be any suitable peptide which recognizes or binds to a target (e.g., a target cell, a target tissue, a target microbial organism). Particularly, a targeting peptide specifically interacts with or specifically recognizes a target, through, for example, the cell surface appendages such as flagella and pili, and surface exposed proteins, lipids and polysaccharides of a target. In one embodiment, a targeting peptide specifically recognizes or interacts with only one or a few target(s) while minimally recognizing or interacting with non-target(s). In another embodiment, a targeting peptide can be a peptide capable of specifically binding to a microorganism, e.g., a target microbial organism.

In one embodiment, the targeting peptide provided by the present invention can be identified via screening peptide libraries. For example, a phage display peptide library can be screened against a target microbial organism or a desired antigen or epitope thereof. In particular, phage display peptide libraries (e.g., Ph.D 7, Ph.D. 12, Ph.D C7C libraries from New England Biolabs) that contain >$10^9$ unique random-peptide-sequence-containing phage clones. The Ph.D.-C7C library displays 7-mer peptides with disulfide linkages, while the Ph.D.-7 and Ph.D.-12 libraries contain completely randomized 7-mer and 12-mer residues, respectively. The M13 filamentous phage used for the procedure carried the random insert as an N-terminal fusion to the minor coat protein pIII. In screening a targeting peptide that specifically recognizes a target or target microbial organism, $10^{10}$ pfu/ml of phage library was incubated with $10^9$ microbial organisms (e.g., bacterial cells) for which targeting peptides are desired. After centrifugation, unbound phage was removed by aspiration. The pellet, which contained the target microbial organisms with the bound phage, was washed several times using buffers containing mild detergent to remove loosely bound phage particles, and the tightly bound phage particles were eluted. This process is termed panning. The eluted phage was amplified by infecting *E. coli* F$^+$ strains. After 3-4 rounds of panning and amplification, a phage pool was obtained, which contained clones with high binding affinity for the bacteria that it was panned against. Ten to twenty phage clones from this pool were randomly picked for DNA sequencing, from which the amino acid sequence of the peptide insert was determined. By aligning the amino acid sequence of multiple clones from the same phage pool, a consensus sequence for the binding/targeting peptide was constructed. This consensus sequence represents one of the binding/targeting peptides specific for the particular microbial organism. To confirm the binding specificity of the consensus peptide, the peptide was chemically synthesized and conjugated to a dye (e.g., FITC, a green fluorescence dye). The labeled peptide was incubated with the microbial organism and analyzed by fluorescent microscopy for target microbial species-specific binding. This methodology ensured that peptides selected from phage display exhibit the same binding specificity as a free peptide independent of the M13 phage particle.

The targeting peptide of the present invention can also be a peptide obtained based on rational design. For example, one can design a targeting peptide based on the biochemical and biophysical characteristics of amino acids and the surfaces of microorganisms. In general, positively charged peptides are likely to bind negatively charged components on the cell surface and vice versa. Similarly, hydrophobic peptides may bind to hydrophobic pockets on the cell surface based on hydrophobic interactions while the secondary or tertiary structure of a peptide may fit into certain structures on the surface of a microorganism.

A peptide identified through a screening or design method can be used as a targeting peptide for specifically recognizing a target microbial organism. Examples of such targeting peptide are disclosed in U.S. patent application Ser. No. 10/706,391 (U.S. Pub. No. 20040137482), which include, for example, 1) targeting peptides capable of specifically binding to or recognizing *Pseudomonas*, especially *P. aeruginosa* (e.g., targeting peptides 12:1, 12:2, 12:3, 12:4, 12:5, 12:6, 12:7, 12:8; 12:9, and 12:10); 2) targeting peptides capable of specifically binding to *Staphylococcus*, especially *S. aureus* (e.g., targeting peptides SA5:1, SA5:3, SA5:4, SA5:5, SA5:6, SA5:7, SA5:8, SA5:9, SA5:10, SA2:2, SA2:4, SA2:5, SA2:6, SA2:7, SA2:8, SA2:9, SA2:10, and SA2:11); and 3) targeting peptides capable of specifically binding to *E. coli* (e.g., targeting peptides DH5.1, DH5.2, DH5.3, DH5.4, DH5.5, DH5.6, DH5.7, DH5.8, and DH5.9).

In one embodiment of the present invention, targeting peptides specifically binding to or recognizing *Pseudomonas*, especially *P. aeruginosa*, include, for example, cat-1 (or KH) domain, KKH (SEQ ID NO 31). Targeting peptides specifically binding to or recognizing Streptococci include, for example, bacterial pheromones such as CSP (SGSLSTF-FRLFNRSFTQALGK, SEQ ID NO 1), CSP 1 (EMRLSKF-FRDFILQRKK, SEQ ID NO 29) and CSP2 (EMRISRIILD-FLFLRKK, SEQ ID NO 30) and fragments thereof. Further, targeting peptides specifically binding to or recognizing *S. pneumoniae* include, for example, CSP1 and CSP2. Targeting peptides specifically binding to or recognizing *S. mutans* include, for example, CSP, C16 or $CSP_{C16}$ (TFFRLFNRS- FTQALGK, SEQ ID NO 2), M8 or CSP$_{M8}$ (TFFRLFNR, SEQ ID NO 5), and peptide 1903 (NIFEYFLE, SEQ ID NO 10).

The targeting peptides provided by the present invention can be naturally or non-naturally occurring peptides. For example, the targeting peptides provided by the present invention can be recombinantly made, chemically synthesized, or naturally existing. In one embodiment, the targeting peptide contains an amino acid sequence that naturally exists (e.g., CSP, CSP 1 and CSP2). In another embodiment, the targeting peptide contains an amino acid sequence that constitutes an internal part of a naturally occurring polypeptide (e.g., C16 and M8 in the present invention). In another embodiment, the targeting peptide contains an amino acid sequence encoded by a sequence naturally existing in a genome and such amino acid sequence is not adjacent to any amino acid sequence naturally adjacent to it, e.g., such amino acid sequence is adjacent to a heterologous sequence in the targeting peptide.

The targeting peptide provided by the present invention can also include a peptide having an amino acid sequence that is derived or modified from a targeting amino acid sequence specifically illustrated in the present invention, provided that the derived or modified sequence still maintains or has an enhanced specificity with respect to its target microbial organism. For example, the targeting amino acid sequence can be structurally modified via deletion, mutation, addition of amino acids or other structural entities, or any other structural changes as long as these changes do not alter or adversely affect the binding ability of the targeting amino acid sequence to its target microbial organism.

The targeting peptide according to the present invention specifically interacts with or binds to the target organism (e.g., through the external surface of the organism) via different molecular interactions such as ionic interaction, Vander Waals forces, ligand-receptor interaction, or hydrophobic interaction. For example, the targeting peptide of the present invention can also be a peptide ligand, receptor, or fragment thereof that specifically recognizes a target microbial organism. In one example, the targeting peptide of the present invention can be a glucan binding protein of *Streptococcus mutans* that can specifically bind insoluble glucans on the surface of *S. mutans*. For another example, the targeting peptides can be a bacterial pheromone or a fragment thereof.

The targeting peptide according to the present invention comprises about 4 to about 40 amino acids, from about 5 to about 30, or from about 6 to about 20. In one preferred embodiment, the targeting peptide has a length of 5, 6, 7, 8, 9, 10, 11, 12, 13, 14, 16, 17, 18, 19, 20, 21, 22, 23, 24, 25, 26, 27, 28, 29, or 30 amino acids.

It is contemplated that the targeting peptides includes peptides which specifically bind a target cell or tissue (e.g., a plant call, an animal cell, or fungal organism). The examples of these targeting peptides include Chitinase, Lectins, and targeting fragments thereof.

The targeting peptide according to the present invention can be produced by any suitable method known to one skilled in the art by itself or in combination with a linker peptide and an antimicrobial peptide. For example, the targeting peptides can be chemically synthesized via a synthesizer or recombinantly made using an expression system, e.g., a bacterial, yeast, or eukaryotic cell expression system. In the chemical synthesis, the targeting peptide can be made by L-amino acid enantiomers or D-amino acid enantiomers. It is observed that the targeting peptide consisting of D-enantiomers increases the stability without compromising the activity of the targeting peptide.

The linker peptide according to the present invention is a peptide that can be used to connect a targeting peptide to an antimicrobial peptide without interfering or reducing the activity of the targeting peptide or the antimicrobial peptide. The peptide linker is from about 2 to 20 amino acids, from 2 to 12, or from 3 to 12 amino acids. Examples of the peptide linkers include, for example, GGG (SEQ ID NO 17), AAA (SEQ ID NO 18), SAT (SEQ ID NO 19), ASA (SEQ ID NO 20), SGG (SEQ ID NO 21), PYP (SEQ ID NO 22), SGS (SEQ ID NO 23), GGS (SEQ ID NO 24), SPS(SEQ ID NO 25), PSGSP (SEQ ID NO 26), PSPSP (SEQ ID NO 27), or a combination (a multimer) of any two (dimer), three (trimer), four (tetramer), five (pentamer) or more than five of the listed peptide linkers. In one embodiment, the linker peptide is GGG (SEQ ID NO 17). In another embodiment, the linker peptide is a dimmer of GGS (SEQ ID NO 24), which is GGSGGS (SEQ ID NO 28).

The linker peptide according to the present invention can be produced by any suitable method known to one skilled in the art by itself or in combination with a targeting peptide and an antimicrobial peptide. For example, the linker peptides can be chemically synthesized via a synthesizer or recombinantly made using an expression system, e.g., a bacterial, yeast, or eukaryotic cell expression system. In the chemical synthesis, the linker peptide can be made by L-amino acid enantiomers or D-amino acid enantiomers. It is observed that peptides consisting of D-enantiomers increase the stability without comprising the activity of the peptides.

The antimicrobial peptide according to the present invention is a peptide capable of killing a microbial organism or inhibiting its growth. The antimicrobial activities of the antimicrobial peptides of the present invention include, without limitation, antibacterial, antiviral, or antifungal activities. Antimicrobial peptides include various classes of peptides, e.g., peptides originally isolated from plants as well as animals. In animals, antimicrobial peptides are usually expressed by various cells including neutrophils and epithelial cells. In mammals including human, antimicrobial peptides are usually found on the surface of the tongue, trachea, and upper intestine. Naturally occurring antimicrobial peptides are generally amphipathic molecules that contain fewer than 100 amino acids. Many of these peptides generally have a net positive charge (i.e., cationic) and most form helical structures.

In one embodiment, the antimicrobial peptide according to the present invention comprises about 2 to about 100 amino acids, from about 5 to about 50, or from about 7 to about 20. In one preferred embodiment, the targeting peptide has a length of 5, 6, 7, 8, 9, 10, 11, 12, 13, 14, 16, 17, 18, 19, 20, 21, 22, 23, 24, 25, 26, 27, 28, 29, or 30 amino acids.

In another embodiment, the antimicrobial peptide has the antimicrobial activity with a minimum inhibitory concentration (MIC) of no more than about 40 µM, no more than about 30 µM, no more than 20 µM, or no more than 10 µM.

In another embodiment, the antimicrobial peptides include those listed in Table 7 (SEQ ID Nos 34-35 and 54-97). In another embodiment, the antimicrobial peptide contains one or more antimicrobial peptides including, without limitation, alexomycin, andropin, apidaecin, bacteriocin, β-pleated sheet bacteriocin, bactenecin, buforin, cathelicidin, α-helical clavanin, cecropin, dodecapeptide, defensin, β-defensin, α-defensin, gaegurin, histatin, indolicidin, magainin, melittin, nisin, novispirin G10, protegrin, ranalexin, tachyplesin, and derivatives thereof.

Among these known antimicrobial peptides, tachyplesins are known to have antifungal and antibacterial activities. Andropin, apidaecin, bactencin, clavanin, dodecappeptide, defensin, and indolicidin are antimicrobial peptides having antibacterial activities. Buforin, nisin and cecropin peptides have been demonstrated to have antimicrobial effects on *Escherichia. coli, Shigella* disenteriae, *Salmonella typhimurium, Streptococcus pneumoniae, Staphylococcus aureus,* and *Pseudomonas aeroginosa.* Magainin and ranalexin peptides have been demonstrated to have antimicrobial effects on the same organisms, and in addition have such effects on *Candida albicans, Cryptococcus neoformans, Candida krusei,* and *Helicobacter pylori.* Magainin has also been demonstrated to have antimicrobial effects on herpes simplex virus. Alexomycin peptides have been demonstrated to have antimicrobial effects on *Campylobacter jejuni, Moraxella catarrhalis* and *Haemophilus influenzae* while defensin and β-pleated sheet defensin peptides have been shown to have antimicrobial effects on *Streptococcus pneumoneae.* Histatin peptides and the derivatives thereof are another class of antimicrobial peptides, which have antifungal and antibacterial activities against a variety of organisms including *Streptococcus mutans* (MacKay, B. J. et al., Infect. Immun. 44:695-701 (1984); Xu, et al., J. Dent. Res. 69:239 (1990)).

In one embodiment, the antimicrobial peptide of the present invention contains one or more antimicrobial peptides from a class of histatin peptides and the derivatives thereof. For example, the antimicrobial peptide of the present invention contains one or more derivatives of histatin including, without limitation, histatin 5 having an amino acid sequence of DSHAKRHHGY KRKFHEKHHS HRGY (SEQ ID NO 32) or dhvar-1 having an amino acid sequence of KRLFKELKFS LRKY (SEQ ID NO 33).

In another embodiment, the antimicrobial peptide of the present invention contains one or more antimicrobial peptides from a class of protegrins and the derivatives thereof. For example, the antimicrobial peptide of the present invention contains protegrin PG-1 having an amino acid sequence of RGGRLCYCRRRFCVCVGR (SEQ ID NO 34). The protegrin peptides have been shown to have antimicrobial effects on *Streptococcus mutans, Neisseria gonorrhoeae, Chlamydia trachomatis* and *Haempohilus influenzae.* Protegrin peptides are described in U.S. Pat. Nos. 5,693,486, 5,708,145, 5,804,558, 5,994,306, and 6,159,936, all of which are incorporated herein by reference.

In yet another embodiment, the antimicrobial peptide of the present invention contains one or more antimicrobial peptides from a class of novispirin and the derivatives thereof for treating cariogenic organisms, e.g., *Streptococcus mutans* or *Pseudomonas* aeroginosa. For example, the antimicrobial peptide of the present invention includes novispirin G10 having an amino acid sequence KNLRRI-IRKGIHIIKKYG (SEQ ID NO 35) and G2 (a derivative of novispirin G10) which has one C-terminal amino acid deletion, and one internal deletion from G10 and an amidated C-terminus having the amino acid sequence of KNL-RIIRKGIHIIKKY* (SEQ ID NO 3) (* denotes C-terminal amidation).

In yet another embodiment, the antimicrobial peptide of the present invention contains peptides rationally designed and tested to possess the antimicrobial activity against a microbial organism (e.g., *Streptococcus mutans*). The examples of these peptides include, without any limitation, S6L3-33 having an amino acid sequence of FKKFWKW-FRRF (SEQ ID NO 7) and BD2.21 having an amino acid sequence of KLFKFLRKHLL (SEQ ID NO 11).

The antimicrobial peptide according to the present invention can be produced by any suitable method known to one skilled in the art by itself or in combination with a targeting peptide and a linker peptide. For example, the antimicrobial peptides can be chemically synthesized via a synthesizer or recombinantly made using an expression system, e.g., a bacterial, yeast, or eukaryotic cell expression system. In the chemical synthesis, the antimicrobial peptide can be made by L-amino acid enantiomers or D-amino acid enantiomers.

In yet another embodiment, the STAMP comprises a targeting peptide and an antimicrobial peptide, wherein the targeting peptide is covalently linked to the antimicrobial peptide via a peptide bond, wherein the targeting peptide is selected from the group consisting of C16 (SEQ ID NO 2), M8 (SEQ ID NO 5), and 1903 (SEQ ID NO 10); and wherein the antimicrobial peptide is selected from the group consisting of G2 (SEQ ID NO 3), S6L3-33 (SEQ ID NO 7) and BD2.21 (SEQ ID NO 11).

In yet another embodiment, the STAMP comprises a targeting peptide which is covalently linked to a linker peptide via a peptide bond and an antimicrobial peptide which is covalently linked to the linker peptide via a peptide bond, wherein the targeting peptide is selected from the group consisting of C16 (SEQ ID NO 2), M8 (SEQ ID NO 5), and 1903 (SEQ ID NO 10); wherein the antimicrobial peptide is selected from the group consisting of G2 (SEQ ID NO 3), S6L3-33 (SEQ ID NO 7) and BD2.21 (SEQ ID NO 11). In yet another embodiment, the peptide linker is selected from the group consisting of GGG (SEQ ID NO 17), AAA (SEQ ID NO 18), SAT (SEQ ID NO 19), ASA (SEQ ID NO 20), SGG (SEQ ID NO 21), PYP (SEQ ID NO 22), SGS (SEQ ID NO 23), GGS (SEQ ID NO 24), SPS (SEQ ID NO 25), PSGSP (SEQ ID NO 26), PSPSP (SEQ ID NO 27), and GGSGGS (SEQ ID NO 28). Examples of such STAMPs include but are not limited to the STAMPS listed in Table 1: C16G2 (SEQ ID NO 4); C16-33 (SEQ ID NO 8); C16-BD2.21 (SEQ ID NO 14); M8G2 (SEQ ID NO 6); M8-33 (SEQ ID NO 9); M8-BD2.21 (SEQ ID NO 15); 1903-G2 (SEQ ID NO 12); 1903-33 (SEQ ID NO 16); and 1903-BD2.21 (SEQ ID NO 13).

Another aspect of the present invention relates to a composition comprising a plurality of STAMPS, wherein the composition comprises a first STAMP and a second STAMP and the first STAMP is different from the second STAMP. In one embodiment, the first STAMP comprises a first targeting peptide covalently linked to a first antimicrobial peptide via a peptide bond. The second STAMP comprises a second targeting peptide covalently linked to a second antimicrobial peptide via a peptide bond. The difference between the first STAMP and the second STAMP is such that at least one corresponding moiety of the two STAMPs is different from each other. For example, in one embodiment, the first targeting peptide is different from the second targeting peptide or the first antimicrobial peptide is different from the second antimicrobial peptide. In another embodiment, the first targeting peptide is different from the second targeting peptide and the first antimicrobial peptide is different from the second antimicrobial peptide.

In another embodiment, the first STAMP comprises a first targeting peptide which is covalently linked to a first linker peptide via a peptide bond and a first antimicrobial peptide which is covalently linked to the first linker peptide via a peptide bond. The second STAMP comprises a second targeting peptide which is covalently linked to a second linker peptide via a peptide bond and a second antimicrobial peptide which is covalently linked to the second linker peptide via a peptide bond. The difference between the first STAMP and the second STAMP is such that at least one corresponding moiety of the two STAMPs is different from each other. For example, in one embodiment, the first targeting peptide is different from the second targeting peptide (the first linker peptide is the same as the second linker peptide and the first antimicrobial peptide is the same as the second antimicrobial peptide); or the first linker peptide is different from the second peptide linker; or the first antimicrobial peptide is different from the second antimicrobial peptide. In another embodiment, the first targeting peptide is the same as the second targeting peptide (the first linker peptide is different from the second linker peptide and the first antimicrobial peptide is different from the second antimicrobial peptide); or the first peptide linker is the same as the second peptide linker; or the first antimicrobial peptide is the same the second antimicrobial peptide. In another embodiment, the first targeting peptide is different from the second targeting peptide, the first linker peptide is different from the second peptide linker; and the first antimicrobial peptide is different from the second antimicrobial peptide.

The STAMP of the present invention can be made by any suitable means known to one skilled in the art. In one embodiment, a nucleotide sequence encoding the STAMP can be synthesized through a DNA synthesizer or a nucleotide sequence encoding a targeting peptide can be ligated to a nucleotide sequence encoding an antimicrobial peptide moiety, either directly or via a nucleotide sequence encoding a peptide linker. The nucleotide can be expressed in an appropriate expression system, e.g., a commercially available bacterial, yeast, or eukaryotic cell expression system. In the chemical synthesis, the STAMP can be made by L-amino acid enantiomers or D-amino acid enantiomers. It is observed that the STAMP consisting of D-enantiomers increases the stability without comprising the activity of the STAMP.

Another aspect of the present invention relates to a STAMP composition comprising a STAMP and an antibiotic. A synergistic antimicrobial effect has been unexpectedly observed when a STAMP is co-administered with an antibiotic in killing or reducing the growth of a target microbial organism. Antibiotics suitable for co-administration with the STAMP include substances, produced synthetically or naturally, which can inhibit the growth of or kill microbial organisms. Such antibiotics include, without any limitation, β-lactam antibiotics (e.g., ampicillin, aziocillin, aztreonam, carbenicillin, cefoperazone, ceftriaxone, cephaloridine, cephalothin, cloxacillin, moxalactam, penicillin, piperacillin, and ticarcillin), amoxicillin, bacitracin, chloramphenicol, clindamycin, capreomycin, colistimethate, ciprofloxacin, doxycycline, erythromycin, fusidic acid, fosfomycin, fusidate sodium, gramicidin, gentamycin, lincomycin, minocycline, macrolides, monobactams, nalidixic acid, novobiocin, ofloxcin, rifamycins, tetracyclines, vancomycin, tobramycin, and trimethoprim. In one example, the STAMP composition comprises a G10KHc STAMP (SEQ ID NO 36) and tobramycin and exhibits a synergistic enhancement of antimicrobial activity to $P.$ $aeruginosa$ in both biofilms and planktonic cultures.

Another aspect of the present invention relates to a STAMP composition comprising a STAMP and an agent which can enhance, maintain, or facilitate the function or activity of the STAMP. In one embodiment, the chemical is a protease inhibitor. The STAMP composition is exposed to a protease-present environment where the presence of the protease may reduce the antimicrobial activity of the STAMP via, for example, enzymatic degradation. The combination of a protease inhibitor and a STAMP stabilizes the STAMP from the protease degradation and thus enhance the activity of the STAMP. The protease-present environment includes, for example, body fluid (e.g., urine, blood, serum, salvia, sputum, mucosal fluid). The protease includes, for example, neutrophil elastase, proteinase-3, cysteine protease, metalloprotease, serine-protease, or other proteases derived from bacteria and/or hosts. The protease inhibitor includes, for example, BMF, EDTA, PMFS, benzamidine, and/or recombinant α-1 antitrypsin (rAAT).

In yet another embodiment, the agent is human DNase. One example of the STAMP composition is the combination of a STAMP (G10KHc (SEQ ID NO 36) and a DNase. The composition was used to reduce $P.$ $areruginosa$ in sputum and exhibited enhanced antimicrobial activity of G10KHc, as the DNase reduced sputum viscosity and enhanced the STAMP diffusion.

Another aspect of the present invention relates to a pharmaceutical composition comprising a STAMP and a suitable pharmaceutical carrier. The term "pharmaceutically acceptable carrier" as used herein means a pharmaceutically-acceptable material, composition or vehicle, such as a liquid or solid filler, diluent, excipient, solvent or encapsulating material, involved in carrying or transporting a STAMP from one location, body fluid, tissue, organ, or portion of the body, to another location, body fluid, tissue, organ, or portion of the body. Each carrier must be "pharmaceutically acceptable" in the sense of being compatible with the other ingredients, e.g., a STAMP, of the formulation and suitable for use in contact with the tissue or organ of humans and animals without excessive toxicity, irritation, allergic response, immunogenicity, or other problems or complications, commensurate with a reasonable benefit/risk ratio. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (1) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Another aspect of the present invention is a diagnostic agent comprising a targeting peptide and a detectable agent. The diagnostic agent of this invention can be useful in diagnostic assays, e.g., for detecting the presence or amount of a target or target microbial organism in a place where the target organism is susceptible to exist (e.g., tissues, organs, body fluid, sputum, surface of a body or organ, mucosal surface, implant, biofilm, or serum, device, air, fluid, cell culture, surface of an industry article or a device), or for detecting the onset, development, or remission of a condition (e.g., an infection or a disease) associated with the target microorganism.

In one embodiment, the targeting peptide typically will be labeled with or conjugated to a detectable agent. Numerous detectable agents are available which can be generally grouped into the following categories:

(a) Radioisotopes, such as $^{35}S$, $^{14}C$, $^{13}C$, $^{15}N$, $^{125}I$, $^{3}H$, and $^{131}I$. The peptide can be labeled with the radioisotope using the techniques known in the art and radioactivity can be measured using scintillation counting; in addition, the peptide can be spin labeled for electron paramagnetic resonance for carbon and nitrogen labeling.

(b) Fluorescent agents such as BODIPY, BODIPY analogs, rare earth chelates (europium chelates), fluorescein and its derivatives, FITC, 5,6 carboxyfluorescein, rhodamine and its derivatives, dansyl, Lissamine, phycoerythrin, green fluorescent protein, yellow fluorescent protein, red fluorescent protein and Texas Red. Fluorescence can be quantified using a fluorometer.

(c) Various enzyme-substrate agents, such luciferases (e.g., firefly luciferase and bacterial luciferase), luciferin, 2,3-dihydrophthalazinediones, malate dehydrogenase, urease, peroxidase such as horseradish peroxidase (HRPO), alkaline phosphatase, β-glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

In another embodiment, the detectable agent is not necessarily conjugated to the targeting peptide but is capable of recognizing the presence of the targeting peptide and the agent can be detected. For example, the detectable agent is an antibody that specifically binds to the targeting peptide. The antibody can then be detected or quantified through various methods known in the art (See Harlow & Lane, Antibodies—A Laboratory Manual (1988)).

In another embodiment, the diagnostic agent of the present invention can be provided in a kit, i.e., a packaged combination of reagents in predetermined amounts with instructions for performing the diagnostic assay. Where the targeting peptide is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

According to another aspect of the present invention, the compositions (e.g., the STAMPs or the STAMP compositions) of the present invention can be used to kill, inhibit or reduce the growth of a target microbial organism to which the targeting peptide specifically binds.

In one embodiment, the compositions of the present invention provide antimicrobial effect to a target microbial organism and can be used to treat a disease or infection associated with the target microbial organism. An antimicrobial effect includes inhibiting the growth or killing of the target microbial organisms, or interfering with any biological functions of the target microbial organisms. In general, the compositions of the present invention can be used to treat a disease or infection at any place in a host, e.g., at any tissue including surfaces of any tissue or implant. In one embodiment, the compositions are used to specifically kill or inhibit planktonic target microbial organisms in body fluid (e.g., blood, sputum). In one embodiment, the compositions of the present invention are used to treat a disease or infection on a mucosal surface or a surface containing a biofilm.

The term "biofilm" refers to an accumulation of microbial organisms that produce an extracellular polysaccharide and proteinaceous material that act as a natural glue to immobilize or embed the organisms. Biofilms may form on solid biological or non-biological surfaces. A biofilm consisting essentially of non-harmful, non-pathogenic, commensal microbial organisms is essential for maintaining a healthy and normal microbial flora to prevent the invasion and establishment of other pathogenic microbial organisms, e.g., yeast infection. However, if the microorganism population in a biofilm is disturbed by overpopulation of pathogenic microbial organisms (e.g., cariogenic organisms like *Streptococcus mutans*), the resulting biofilm may lead to biofilm-associated microbial infection. Examples of biofilm-associated microbial infections include infections of oral soft tissues, teeth and dental implants; middle ear; gastrointestinal tract; urogenital tract; airway/lung tissue; eye; urinary tract prostheses; peritoneal membrane and peritoneal dialysis catheters, indwelling catheters for hemodialysis and for chronic administration of chemotherapeutic agents (Hickman catheters); cardiac implants such as pacemakers, prosthetic heart valves, ventricular assist devices, and synthetic vascular grafts and stents; prostheses, internal fixation devices, and percutaneous sutures; and tracheal and ventilator tubing. Both indwelling and subcutaneous biomedical implants or devices are potential sites for microbial or boilfilm-based infections and represent important targets for the control of infection, inflammation, and the immune response. Biomedical systems such as blood oxygenators, tracheal lavage, dental water units, and dialyzers are also susceptible to bacterial contamination and biofilm formation.

In yet another embodiment, the composition of present invention can be used to disturb the balance of pathogen-containing biofilm (e.g., a biofilm overpopulated by pathogenic microbial organisms) such that undesirable, pathogenic microbial organisms (target microbial organisms) are selectively killed, inhibited or reduced and the desirable, non-pathogenic microbial populations (non-target microbial organisms) are minimally impacted. The composition can be used in many places in an animal or human body which have mucosal surfaces colonized by multiple species microbial biofilms. Examples of these places include mouth, vagina, gastrointestinal (GI) tract, esophageal tract, respiratory tract, implants. For example, in human mouth there usually exist many different microbes including yeasts and bacteria. Most of the bacteria are non-harmful commensal bacteria. Administering the composition of the present invention targets specifically to, for example, cariogenic organisms (e.g. *Streptococcus mutans*) and will have minimum effect on non-targeted microbial organisms, and thus will not have an undesirable effect on non-targeted microbial organisms.

The composition of the present invention can also be used to inhibit target microbial organisms or apply to various biofilm surfaces outside of a human body, e.g., industrial articles or applications. For example, in food processing industry the composition of the present invention can be administered to food processing equipments or food itself to prevent infections related to food consumption, e.g., *Salmonella* in a poultry processing facility.

The target microbial organism of the present invention can be any bacteria, *rickettsia*, fungi, yeasts, protozoa, or parasites. In one embodiment, the target microbial organism is a cariogenic organism, e.g., *Streptococcus mutans*. In another embodiment, the target microbial organisms of the present invention include, without limitation, *Escherichia coli, Candida, Salmonella, Staphylococcus*, and *Pseudomonas*, especially *Campylobacter jejuni, Candida albicans, Candida krusei, Chlamydia trachomatis, Clostridium difficile, Cryptococcus neoformans, Haempohilus influenzae, Helicobacter pylor, Moraxella catarrhalis, Neisseria gonorrhoeae, Pseudomonas aeroginosa, Salmonella typhimurium, Shigella disenteriae, Staphylococcus aureus*, and *Streptococcus pneumoniae*.

For example, *S. mutans* infection is commonly found in mouth and causes dental caries. *Porphyromonas gingivalis*, various *Actinomyces* species, spirochetes, and black-pigmented bacteroides are commonly associated with infections of gingival and surrounding connective tissues, which cause periodontal diseases. *Streptococcus pneumoniae, Haemophilius influenza*, or *Moraxella cararrhalis* infections are commonly found in acute otitis media (AOM) and otitis media effusion (OME) as complications of upper respiratory infections in young children.

*Helicobacter pylori* (*H. pylori*) bacteria are found in the gastric mucous layer or adherent to the epithelial lining of the stomach, and cause more than 90% of duodenal ulcers and up to 80% of gastric ulcers. Other GI tract infections include, without limitation, *campylobacter* bacterial infection, primarily *Campylobacter jejuni* associated with diarrhea, cholera caused by *Vibrio cholerae* serogroups, *salmonellosis* caused by bacteria *salmonella* such as *S. typhimurium* and *S. enteritidis*, shigellosis caused by bacteria *Shigella*, e.g., *Shigella dysenteriae* and traveler's diarrhea caused by enterotoxigenic *Escherichia coli* (ETEC). *Clostridium difficile* infection is also commonly found in the gastrointestinal tract or esophageal tract.

*Pseudomonas* organisms have been associated with common-source nosocomial outbreaks; in addition, they have been incriminated in bacteremia, endocarditis, and osteomyelitis in narcotic addicts. Infections with *Pseudomonas* organisms can also occur in the ear, lung, skin, or urinary tract of patients, often after the primary pathogen has been eradicated by antibiotics. Serious infections are almost invariably associated with damage to local tissue or with diminished host resistance. Patients compromised by cystic fibrosis and those with neutropenia appear at particular risk to severe infection with *P. aeruginosa*. Premature infants; children with congenital anomalies and patients with leukemia; patients with burns; and geriatric patients with debilitating diseases are likely to develop *Pseudomonas* infections. The organism is prevalent in urine receptacles and on catheters, and on the hands of hospital staff.

The staphylococci, of which *Staphylococcus aureus* is the most important human pathogen, are hardy, gram-positive bacteria that colonize the skin of most human beings. If the skin or mucous membranes are disrupted by surgery or trauma, staphylococci may gain access to and proliferate in the underlying tissues, giving rise to a typically localized, superficial abscess. Although these cutaneous infections are most commonly harmless, the multiplying organisms may invade the lymphatics and the blood, leading to the potentially serious complications of staphylococcal bacteremia. These complications include septic shock and serious metastatic infections, including endocarditis, arthritis, osteomyelitis, pneumonia, and abscesses in virtually any organ. Certain strains of *S. aureus* produce toxins that cause skin rashes or that mediate multisystem dysfunction, as in toxic shock syndrome. Coagulase-negative staphylococci, particularly *S. epidermidis*, are important nosocomial pathogens, with a particular predilection for infecting vascular catheters and prosthetic devices. *S. saprophyticus* is a common cause of urinary tract infection.

Yeast or *Candida* infections (Candidiasis) typically occur either orally (Oropharyngeal *Candida* or OPC) or vaginally (Vulvovaginal *Candida* or VVC). Candidiasis is caused by a shift in the local environment that allows *Candida* strains (most commonly *Candida albicans*) already present on skin and on mucosal surfaces such as mouth and vagina to multiply unchecked. Gonorrhea, *chlamydia*, syphilis, and trichommoniasis are infections in the reproductive tract, which cause sexually transmitted diseases, e.g., pelvic inflammatory disease.

Administration of the compositions according to the present invention. The STAMP or the STAMP composition can be administered to a subject by any administration route known in the art, including without limitation, oral, enteral, buccal, nasal, topical, rectal, vaginal, aerosol, transmucosal, epidermal, transdermal, ophthalmic, pulmonary, and/or parenteral administration. A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

The STAMP or the STAMP composition can be given to a subject in the form of formulations or preparations suitable for each administration route. The formulations useful in the methods of the present invention include one or more STAMPs, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of a STAMP which can be combined with a carrier material to produce a pharmaceutically effective dose will generally be that amount of a STAMP which produces a therapeutic effect. Generally, out of one hundred percent, this amount will range from about 1 percent to about ninety-nine percent of the STAMP, preferably from about 5 percent to about 70 percent.

Methods of preparing these formulations or compositions include the step of bringing into association a STAMP with one or more pharmaceutically acceptable carriers and, optionally, one or more accessory ingredients. In general, the formulations are prepared by uniformly and intimately bringing into association a STAMP with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a STAMP as an active ingredient. A compound may also be administered as a bolus, electuary, or paste. For example, in one embodiment, the compositions of the present invention are used to treat or prevent cariogenic organism infections, e.g., *S. mutans* infection associated with dental caries and are prepared as additives to food or any products having direct contact to an oral environment, especially an oral environment susceptible to dental caries. To treat or prevent dental caries one or more compositions of the present invention can be formulated into a baby formula, mouthwash, lozenges, gel, varnish, toothpaste, toothpicks, tooth brushes, or other tooth cleansing devices, localized delivery devices such as sustained release polymers or microcapsules, oral irrigation solutions of any kind whether mechanically delivered or as oral rinses, pacifiers, and any food including, without limitation, chewing gums, candies, drinks, breads, cookies, and milk.

In solid dosage forms for oral administration (e. g., capsules, tablets, pills, dragees, powders, granules and the like), the STAMP is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a STAMP therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the STAMP(s) only, or preferentially, in a certain portion of the gastrointestinal tract, optionally, in a delayed manner. Examples of embedding compositions which can be used include polymeric substances and waxes. The STAMP can also be in microencapsulated form, if appropriate, with one or more of the above-described excipients.

Liquid dosage forms for oral administration include pharmaceutically acceptable emulsions, microemulsions, solutions, suspensions, syrups and elixirs. In addition to the STAMP, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the STAMP, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more STAMPs with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Formulations for the topical or transdermal or epidermal administration of a STAMP composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. The ointments, pastes, creams and gels may contain, in addition to the STAMP composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the STAMP composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The STAMP composition can be alternatively administered by aerosol. This is accomplished by preparing an aqueous aerosol, liposomal preparation or solid particles containing the STAMPs. A nonaqueous (e. g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches can also be used to deliver STAMP compositions to an infection site. Such formulations can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Formulations suitable for parenteral administration comprise a STAMP in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e. g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of a STAMP or in biodegradable polymers such as polylactide-polyglycolide. Depending on the ratio of the STAMP to polymer, and the nature of the particular polymer employed, the rate of drug release can be controlled. Examples of other biodegradable polymers include poly (orthoesters) and poly (anhydrides). Depot injectable formulations are also prepared by entrapping the STAMP in liposomes or microemulsions which are compatible with body tissue.

In a preferred embodiment of the invention, a STAMP composition is delivered to a disease or infection site in a therapeutically effective dose. As is known in the art of pharmacology, the precise amount of the pharmaceutically effective dose of a STAMP that will yield the most effective results in terms of efficacy of treatment in a given patient will depend upon, for example, the activity, the particular nature, pharmacokinetics, pharmacodynamics, and bioavailability of a particular STAMP, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, and the severity or propensity of a disease caused by pathogenic target microbial organisms, to name a few. However, the above guidelines can be used as the basis for fine-tuning the treatment, e. g., determining the optimum dose of administration, which will require no more than routine experimentation consisting of monitoring the subject and adjusting the dosage. Remington: The Science and Practice of Pharmacy (Gennaro ed. 20.sup.th edition, Williams & Wilkins PA, USA) (2000).

EXAMPLES

Example 1. Targeted Killing of *Streptococcus mutans* by a List of Antimicrobial Peptides 1.1 Design and construction of STAMPs used in the example and STAMP components (e.g., selectively targeting domains/peptides, antimicrobial peptides, and linker peptides). STAMPs and their components designed and synthesized in the examples are listed in Table 1. An initial STAMP was constructed by synthesizing full length *S. mutans*-specific competence stimulating peptide (CSP, 21 amino acids, SEQ ID NO 1, pheromone produced by *S. mutans*) with the antimicrobial peptide G2 (SEQ ID NO 3) (16 amino acids, derived from the wide spectrum antimicrobial peptide novispirin G10 (SEQ ID NO 35) (Eckert et al., 2006) at either the C-terminus or the N-terminus. Biological testing of these STAMPs did not reveal any antimicrobial activity. The C-terminal 16 amino acids of CSP, called $CSP_{C16}$ (SEQ ID NO 2), which in previous studies was shown to still have pheromone activity (Qi et al., 2005)), was used as a substitute for CSP. Peptides containing $CSP_{C16}$ at either the N or C-terminus of G2, with different linker regions of flexible amino acids in between, were then synthesized and screened for their antimicrobial activities (data not shown). From among the potential STAMPs, C16G2 (SEQ ID NO 4) which consisted of (from N to C terminus) $CSP_{C16}$, a short linker peptide (GGG; SEQ ID NO:17) and G2 (Table 1), was selected for further study due to its improved minimum inhibitory concentration (MIC), greatly enhanced killing kinetics and selectivity against *S. mutans* (when compared to G2 alone), as disclosed in detail below.

TABLE 1

Peptide sequences (single-letter amino acid code) of selected STAMPs, and STAMP components

| Peptide | Properties | Amino-acid sequence | SEQ ID No. |
|---|---|---|---|
| CSP | Pheromone | SGSLSTFFRLFNRSFTQALGK | 1 |
| C16 ($CSP_{C16}$) | Targeting | TFFRLFNRSFTQALGK | 2 |
| G2 | Antimicrobial | KNLRIIRKGIHIIKKY* | 3 |
| C16G2 | STAMP | TFFRLFNRSFTQALGK<u>GGG</u>KNLRIIRKGIHIIKKY* | 4 |
| M8 or $CSP_{M8}$ | Targeting | TFFRLFNR | 5 |
| M8G2 | STAMP | TFFRLFNR<u>GGG</u>KNLRIIRKGIHIIKKY* | 6 |
| S6L3-33 | Antimicrobial | FKKFWKWFRRF | 7 |
| C16-33 | STAMP | TRRRLFNRSFTQALGK<u>SGGG</u>FKKFWKWFRRF | 8 |
| M8-33 | STAMP | TFFRLFNR<u>SGGG</u>FKKFWKWFRRF | 9 |
| 1903 | Targeting | NIFEYFLE | 10 |
| BD2.21 | Antimicrobial | KLFKFLRKHLL | 11 |
| 1903-G2 | STAMP | NIFEYFLE<u>GGG</u>KNLRIIRKGLHIIKKY | 12 |
| 1903-BD2.21 | STAMP | NIFEYFLE<u>GGG</u>KLFKFLRKHLL | 13 |
| C16-BD2.21 | STAMP | TFFRLFNRSFTQALGK<u>GGG</u>KLFKFLRKHLL | 14 |
| M8-BD2.21 | STAMP | TFFRLFNR<u>GGG</u>KLFKFLRKHLL | 15 |
| 1903-33 | STAMP | NIFEYFLE<u>GGG</u>FKKFWKWFRRF | 16 |

*Denotes peptide C-terminal amidation
Linker regions between targeting and killing peptides are underlined To determine whether there was a region within the $CSP_{C16}$ sequence that was responsible for S. mutans-specific binding, we synthesized a series of fluorescently labeled $CSP_{C16}$ fragments, and analyzed their ability to bind to S. mutans. The following strategies were utilized in dissecting the $CSP_{C16}$ sequence (Table 2): First, a series of fragments were constructed by generating deletions of 3 or 4 amino acids, from the N to C terminus, across the $CSP_{C16}$ sequence (C16-1 to C16-5). Peptides lacking larger portions of the C or N termini of $CSP_{C16}$ were also synthesized (C16-6 to C16-12). Additionally, peptides with Arg to Asn (a positive to negative change in charge) (C16-4) or Phe to Gly substitutions (for a general decrease in hydrophobicity) (C16-3), as well as peptides representing a 4-residue Ala scan of the C16 sequence were constructed (C16-15 to C16-18). Binding assays were performed as described previously (15), and the results summarized in Table 2. $CSP_{C16}$ and any peptides containing Thr6 through Arg13 (TFFRLFNR, SEQ ID NO 5) of CSP were detected as bound to S. mutans UA159 or comD cells while any interruption to this region via deletion, substitution or Ala scanning reduced the detected fluorescent binding compared to $CSP_{C16}$. Some peptides, such as C16-3, -11, -16 and -17, which contained only Thr6-Phe11 and Phe7-Phe11, showed binding but at a weaker intensity than $CSP_{C16}$ or any other peptides with the complete Thr6-Arg13 region. Additionally, we observed that Arg to Asn or Phe to Gly substitutions were deleterious to cell binding, suggesting that these residues within TFFRLFNR (SEQ ID NO 5, called M8 or $CSP_{M8}$) are required for binding to S. mutans. $CSP_{M8}$ exhibited little or no binding to the other oral streptococci listed in Table 3, indicating that $CSP_{M8}$ may also be capable of specifically binding to S. mutans surfaces. In general, the peptides listed in Table 2 that showed positive binding to S. mutans can be used as targeting peptides against S. mutans. These peptides include C16 (SEQ ID NO 2), C16-3 (SEQ ID NO 39), C16-4 (SEQ ID NO 40), C16-5 (SEQ ID NO 41), C16-6 (SEQ ID NO 42), C16-11 (SEQ ID NO 47), C16-12 (SEQ ID NO 5), C16-16 (SEQ ID NO 51), C16-17 (SEQ ID NO 52), and C16-18 (SEQ ID NO 53).

TABLE 2

Binding of CSP-fragment peptides to S. mutans.
Reported relative binding represents results from both UA159 and comD.

| Peptide | Amino acid sequence | Relative S. mutans binding |
|---|---|---|
| C16 (SEQ ID NO 2) | T F F R L F N R S F T Q A L G K | +++ |

*3 to 4 amino acid internal deletions*

| Peptide | Amino acid sequence | Relative S. mutans binding |
|---|---|---|
| C16-1 (SEQ ID NO 37) | - - - R L F N R S F T Q A L G K | - |
| C16-2 (SEQ ID NO 38) | T F F - - - N R S F T Q A L G K | - |
| C16-3 (SEQ ID NO 39) | T F F R L F - - - - T Q A L G K | ++ |
| C16-4 (SEQ ID NO 40) | T F F R L F N R S - - - A L G K | +++ |
| C16-5 (SEQ ID NO 41) | T F F R L F N R S F T Q - - - K | +++ |

*Terminal deletions*

| Peptide | Amino acid sequence | Relative S. mutans binding |
|---|---|---|
| C16-6 (SEQ ID NO 42) | T F F R L F N R S - - - - - - - | +++ |
| C16-7 (SEQ ID NO 43) | - - - R L F N R S F T Q A - - - | - |
| C16-8 (SEQ ID NO 44) | - - - - - - - R S F T Q A L G K | - |
| C16-9 (SEQ ID NO 45) | T F F - - - - - - - - - - - - - | - |
| C16-10 (SEQ ID NO 46) | T F F R - - - - - - - - - - - - | - |
| C16-11 (SEQ ID NO 47) | T F F R L - - - - - - - - - - - | + |
| C16-12 (SEQ ID NO 5) ($CSP_{M8}$) | T F F R L F N R - - - - - - - - | +++ |

*Substitutions*

| Peptide | Amino acid sequence | Relative S. mutans binding |
|---|---|---|
| C16-13 (SEQ ID NO 48) | T G G R L G N R S G T Q A L G K | - |
| C16-14 (SEQ ID NO 49) | T F F N L F N N S F T Q A L G K | - |

*Alanine-scanning*

| Peptide | Amino acid sequence | Relative S. mutans binding |
|---|---|---|
| C16-15 (SEQ ID NO 50) | A A A A L F N R S F T Q A L G K | - |
| C16-16 (SEQ ID NO 51) | T F F R A A A A S F T Q A L G K | + |
| C16-17 (SEQ ID NO 52) | T F F R L F N R A A A A A L G K | ++ |
| C16-18 (SEQ ID NO 53) | I F F R L F N R S F T Q A A A A | +++ |

Targeting peptides specific to S. mutans 1903 (SEQ ID NO 10) and antimicrobial peptides S6L3-33 (SEQ ID NO 7) and BD2.21 (SEQ ID NO 13) were developed in the inventors' laboratory (See Example 4). Targeting peptides were conjugated to antimicrobial peptides via a linker GGG (SEQ ID NO 17) to yield the STAMPS C16-33 (SEQ ID NO 8), M8-33 (SEQ ID NO 9), 1903-BD2.21 (SEQ ID NO. 13), and C16-BD2.21 (SEQ ID NO 14), all of which were tested in the similar manner as C16G2 and M8G2.

All peptides listed in Tables 1 and 2 were synthesized using double-coupling cycles by standard 9-fluorenylmethyloxycarbonyl (Fmoc) solid-phase synthesis methods (431A Peptide Synthesizer, Applied Biosciences or Apex396, Advanced Chemtech) as described previously (Eckert et al., 2006). Completed peptides were cleaved from the resin with 95% trifluoroacetic acid (TFA) with appropriate scavengers and purified by reverse-phase high performance liquid chromatography (RP-HPLC) (ACTA Purifier, Amersham) to 90-95%. Peptide molecular mass was determined by matrix-assisted laser desorption/ionization (MALDI) mass spectrometry. Peptides C16G2, G2, and M8G2 were synthesized with amidated C-termini using Fmoc-Tyr(tBu)-Rink Amide MBHA resin (Anaspec). All other peptides were synthesized with the appropriately-substituted Wang resins.

1.2 Fluorescent labeling of peptides and fluorescence microscopy. Aliquots of $CSP_{C16}$ (SEQ ID NO 2), CSP-fragment peptides (Table 2), and C16G2 (SEQ ID NO 4) were labeled with carboxyfluorescein (Sigma) as described previously (Eckert et al., 2006). After peptide cleavage but prior to the bacterial labeling assay, fluorescence intensity per μM peptide was checked fluorimetrically ($\lambda_{ex}$=488 nm, $\lambda_{em}$=520 nm VersaFluor, BioRad) and found to be relatively similar (data not shown). To evaluate the level of peptide binding to bacteria, streptococci from an overnight culture ($OD_{600}$ of 0.7-1.0) were washed with phosphate buffered saline (1×PBS), diluted 1:2 into 1×PBS, and exposed to peptide (16 μM) for 5 min at 25° C. After incubation with peptide, unbound agent was removed from the bacteria by three cycles of centrifugation (5 min, 16,000×g) and resuspension in 1×PBS. Labeling of oral streptococci was evaluated using brightfield and fluorescence microscopy (Nikon E400) at a 40× magnification. The digital images utilized for the semi-quantitative binding assessment were acquired with the factory-supplied software (SPOT, Diagnostics).

1.3 Determination of antimicrobial activity. The general antimicrobial activity of peptides against planktonic bacteria was determined by a MIC assay in TH broth (all oral streptococci) (Qi et al., 2005).

S. mutans, S. gordonii Challis (DL1), and S. sanguinis NY101 strains were grown in Todd Hewitt (TH, Fisher) broth medium at 37° C. under anaerobic conditions (80% $N_2$, 10% $CO_2$, and 10% $H_2$). S. mutans strains UA159 (Ajdic et al., 2002), ATCC 25175, and T8 (Rogers, 1975), are wild-type clinical isolates, while comD is a knockout mutant that was constructed previously from the wild-type UA140 background (Qi et al., 2005). Luciferase expressing S. mutans strain JM11 was constructed from UA140 as described (Merritt et al., 2005). Exponentially growing bacterial cells were diluted to ~1×10⁵ cfu/mL in TH and placed into 96-well plates (Fisher). Peptides were then serially diluted and added to the bacteria. MIC was determined by identifying the concentration of peptide that completely inhibited bacterial growth after ~24 h incubation.

1.4 Determination of bactericidal kinetics. To determine the short term killing rate and selectivity of C16G2 and G2 we performed time-kill experiments, essentially as described previously (Eckert et al., 2006). S. mutans UA159, S. gordonii, or S. sanguinis were grown to log phase and diluted to ~1×10$^5$ cfu/mL in growth medium. Under aerobic conditions, 25 µM G2 or C16G2 was added to the cell suspension and incubated at 25° C. At 1 min, 10 µL of cell suspension was removed, rescued by dilution into growth medium (1:50) and kept on ice. For plating, 20-500 µL of rescued cells were spread on growth medium agar plates and colonies were counted after overnight incubation at 37° C. under anaerobic conditions. We considered 60 cfu/mL as the detection limit for this assay. Values of surviving cfu/mL were expressed as the ratio of survivors from C16G2-treated cultures to cfu/mL from samples exposed to G2.

1.5 Examination of antimicrobial activity against single-species biofilms. To initiate biofilm formation, ~1×10$^7$ bacteria per well (from overnight cultures) were seeded in TH medium (100 µL) to a 96-well flat-bottom plate. For all streptococci except S. mutans, the medium was supplemented with 0.5% (w/v) mannose and glucose. S. mutans UA159 biofilms were grown with 0.5% (w/v) sucrose. Plates were then centrifuged briefly to pellet the cells, and bacteria were incubated for 3-4 hours at 37° C. for biofilm formation. After incubation, the supernatant was carefully removed and biofilms were treated with 25 µM peptide in 1×PBS or 1×PBS alone for 1 min. The peptide solution was then removed and 100 µL TH was added to further dilute any remaining peptide. To minimize biofilm loss, cells were briefly centrifuged after TH addition, after which the supernatants were removed and fresh medium plus appropriate sugars were returned. Cells were then incubated anaerobically at 37° C. and biofilm growth was monitored over time by measuring absorbance at $OD_{600}$ with a microplate spectrophotometer (Benchmark Plus, BioRad).

1.6 Evaluation of antimicrobial activity against bacterial biofilm in saliva. For these experiments, we employed methods similar to those previously described (Bleher et al., 2003). A day prior to the assay, saliva was collected and pooled from 5 adult volunteers in the laboratory, diluted 1:4 in TH broth and centrifuged 2,000×g for 10 min. The supernatant was then filter sterilized (0.2 µm filter, Nunc) and stored at 4° C. A portion of pooled saliva was also diluted 1:2 in 1×PBS and processed as before. On the day of the assay, overnight cultures of JM11 and other oral streptococci were normalized to $OD_{600}$ 1.0 and ~3×10$^6$ cfu/mL of each species was added to 10 mL of the TH-diluted saliva. Sucrose, mannose, and glucose (1% w/v each) were then added and the solution mixed. Aliquots (500 µL) of the saliva and bacteria mixture were then placed into 1.5 mL Eppendorf tubes (Fisher). After a brief centrifugation (4,000×g, 2 min), the tubes were incubated for 3-4 hours at 37° C. to form multi-species biofilms. The supernatants were then removed and the spent media replaced with 100 µL PBS-diluted saliva (1:2) plus 25 µM (freshly added) peptide. After biofilms were exposed to the agent for 5 minutes, the PBS-saliva was removed, cells briefly centrifuged, and 500 µL fresh TH-saliva with sugars was returned. At each time point, total biofilm growth was measured by reading absorbance at $OD_{600}$, and the health of S. mutans within the population examined by relative luciferase expression (relative light unit, (RLU) production), as described previously (Merritt et al., 2005). Briefly, biofilms were resuspended by vortex and aspiration and 100 µL of each sample transferred to a new Eppendorf tube with 25 µL 1 mM D-luciferin (Sigma) solution suspended in 0.1 M citrate buffer, pH 6.0. For the 2 h timepoint, biofilms were stimulated after resuspension by the addition of 1% sucrose 30 min prior to recording luciferase activity. RLU production was measured using a TD 20/20 luminometer (Turner Biosystems) and reported values were obtained from the average of 3 independent samples. The data were plotted as the $RLU/OD_{600}$ over time.

1.7 C16G2 has enhanced antimicrobial activity and specificity against planktonic S. mutans cells. To evaluate the antimicrobial activity and general specificity of C16G2, minimum inhibitory concentration (MIC) tests were performed against a panel of bacterial species including various strains of S. mutans and closely related oral streptococci (Gilmore et al., 1987). As shown in Table 3, the MIC values of C16G2 ranged from 3-5 µM for all S. mutans strains tested, a 4-5 fold increase in antimicrobial activity over the parental antimicrobial peptide G2 (12-20 µM). In comparison, we observed little difference in susceptibility between G2 and C16G2 (2 fold or less) against S. gordonii and S. sanguinis.

Figure 1:
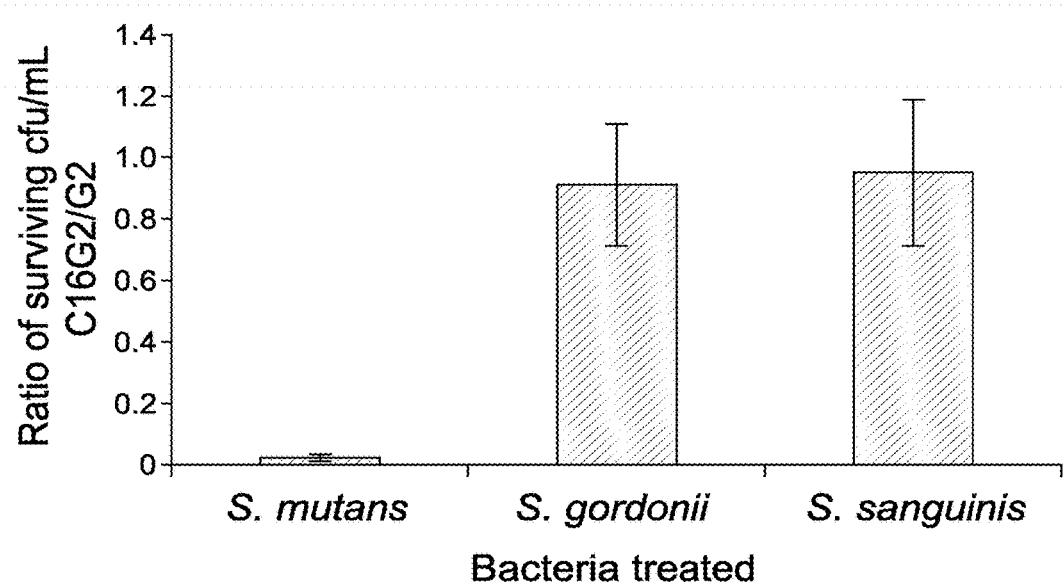
FIG. 1: Selective killing activity of C16G2 against *S. mutans*. *S. mutans*, *S. sanguinis*, and *S. gordonii* planktonic cells were exposed to 25 μM of the STAMP C16G2, or its untargeted parent antimicrobial peptide G2, for 1 min. Surviving cfu/mL were detected and compared. Data represent averages from at least 3 independent experiments.

G10KHc (SEQ ID No 36) did not show much improvement in MIC after 24 h incubation, but displayed greatly enhanced killing kinetics and specificity against the targeted bacteria during short time exposure (when compared to the untargeted parental antimicrobial peptide (Eckert et al., 2006). Therefore, comparative experiments were performed to examine the killing ability C16G2 and G2 against its targeted and untargeted bacteria after a short time exposure. As shown in FIG. 1, with 1 min exposure, C16G2 was over 20-fold more active against its targeted bacterium S. mutans, in comparison to G2, while it exhibited a similar level of activity as G2 against other oral streptococci tested. These findings provided the first indications that the addition of the $CSP_{C16}$ targeting domain to G2 had resulted in an antimicrobial with selective activity against S. mutans, and not other closely related oral streptococci.

TABLE 3

MIC of G2-containing STAMPs and STAMP components against bacteria.
MICs represent averages of at least 3 independent experiments with standard deviations.

| Strains | MIC (µM) of: | | | | | |
|---|---|---|---|---|---|---|
| | CSP | $CSP_{C16}$ | G2 | C16G2 | $CSP_{M8}$ | M8G2 |
| *S. mutans* | | | | | | |
| UA159 | 50.8 ± 9.3 | >60 | 12.1 ± 4.5 | 3.0 ± 1.6 | >60 | 3.25 ± 1.9 |
| 25175 | >60 | >60 | 14.8 ± 2.0 | 3.8 ± 0.3 | >60 | 3.5 ± 0.5 |
| T8 | >60 | >60 | 14.2 ± 1.5 | 3.7 ± 0.2 | >60 | nt |
| comD | >60 | >60 | 15.3 ± 4.2 | 5.1 ± 2.4 | >60 | 4.0 ± 2.0 |

TABLE 3-continued

MIC of G2-containing STAMPs and STAMP components against bacteria.
MICs represent averages of at least 3 independent experiments with standard deviations.

| | MIC (µM) of: | | | | | |
|---|---|---|---|---|---|---|
| Strains | CSP | $CSP_{C16}$ | G2 | C16G2 | $CSP_{M8}$ | M8G2 |
| Non-mutans streptococci | | | | | | |
| S. gordonii | >60 | >60 | 41.3 ± 14.0 | 23.5 ± 7.8 | >60 | 20 ± 5.0 |
| S. sanguinis | >60 | >60 | 33.6 ± 7.5 | 19.1 ± 4.0 | >60 | 15 ± 2.5 |

Figure 2:
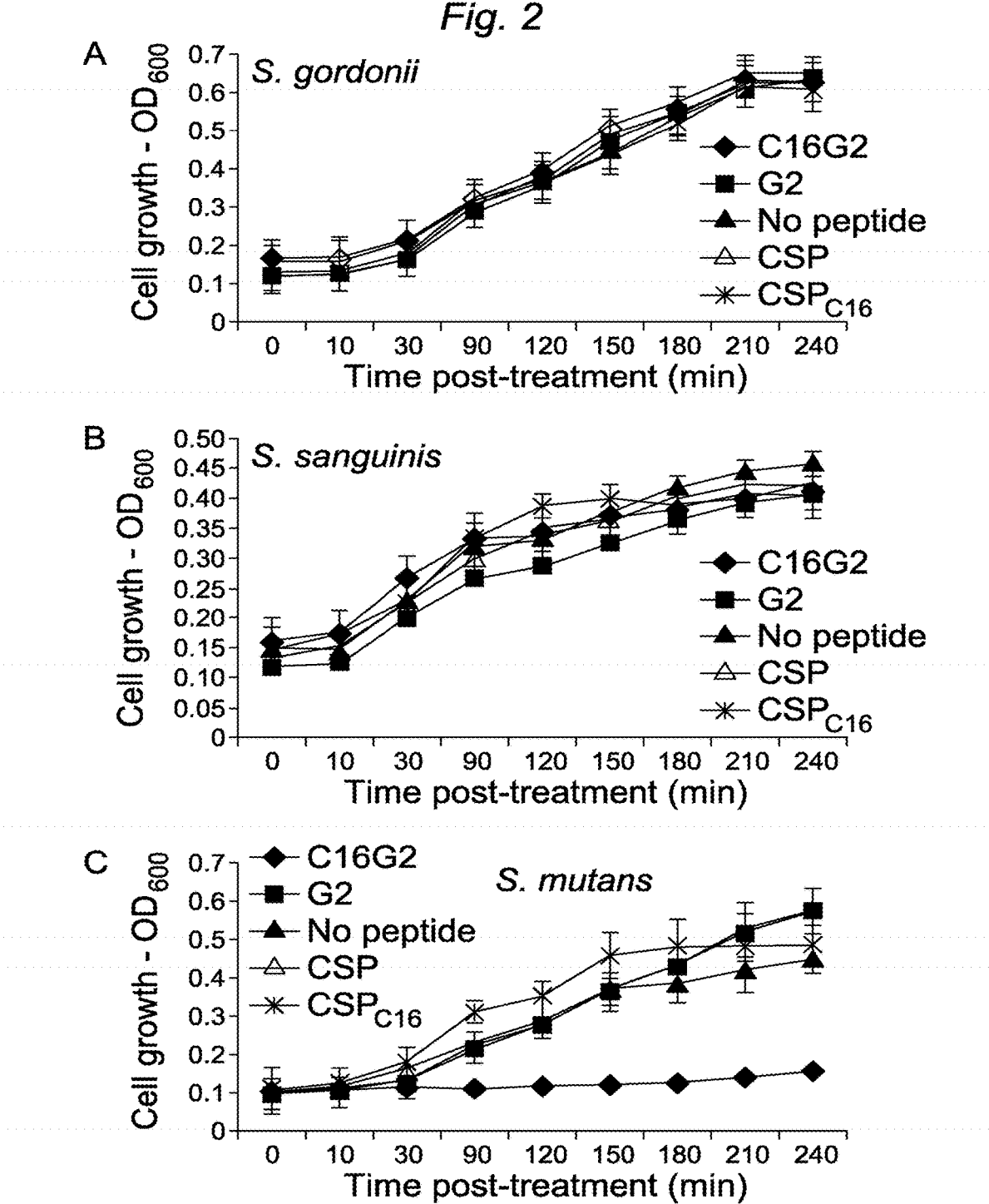
FIG. 2: Inhibitory activity of G2 and C16G2 against single-species biofilms. *S. gordonii* (A), *S. sanguinis* (B) and *S. mutans* (C) monoculture biofilms were grown and then exposed for 1 min to 25 μM STAMP or STAMP component (as indicated in the figure), washed, and regrown with fresh medium. Biofilm recovery was monitored over time by $OD_{600}$. Data represent averages from 3 independent experiments.

1.8 C16G2 is also active against biofilm cells. *S. mutans* predominantly exist in a biofilm growth state in vivo. It is known in the art that biofilm-associated cells are 100-1000 fold more resistant to antibiotics (Donlan et al., 2002). To test whether C16G2 still has activity against *S. mutans* biofilms in vitro, biofilm-associated *S. mutans*, *S. gordonii*, or *S. sanguinis*, were treated with 25 µM C16G2, G2, CSP, $CSP_{C16}$, or 1×PBS, for 1 min, washed, and their re-growth was monitored over time. As shown in FIG. 2, *S. gordonii* or *S. sanguinis* biofilms exposed to any of the peptides tested grew similarly to untreated biofilms after peptide addition and removal (FIG. 2A-B). In contrast, *S. mutans* strains UA159 (FIG. 2C) as well as T8 and 25175 (data not shown) were severely inhibited by treatment with C16G2, but were unaffected by treatment with the other peptides. These results indicate that C16G2 can function as an anti-*S. mutans* STAMP in a biofilm environment with only a short period of exposure (1 min), a time-frame which is relevant for clinical treatments in the oral cavity (Axelsson & Lindhe, 1987).

Figure 3:
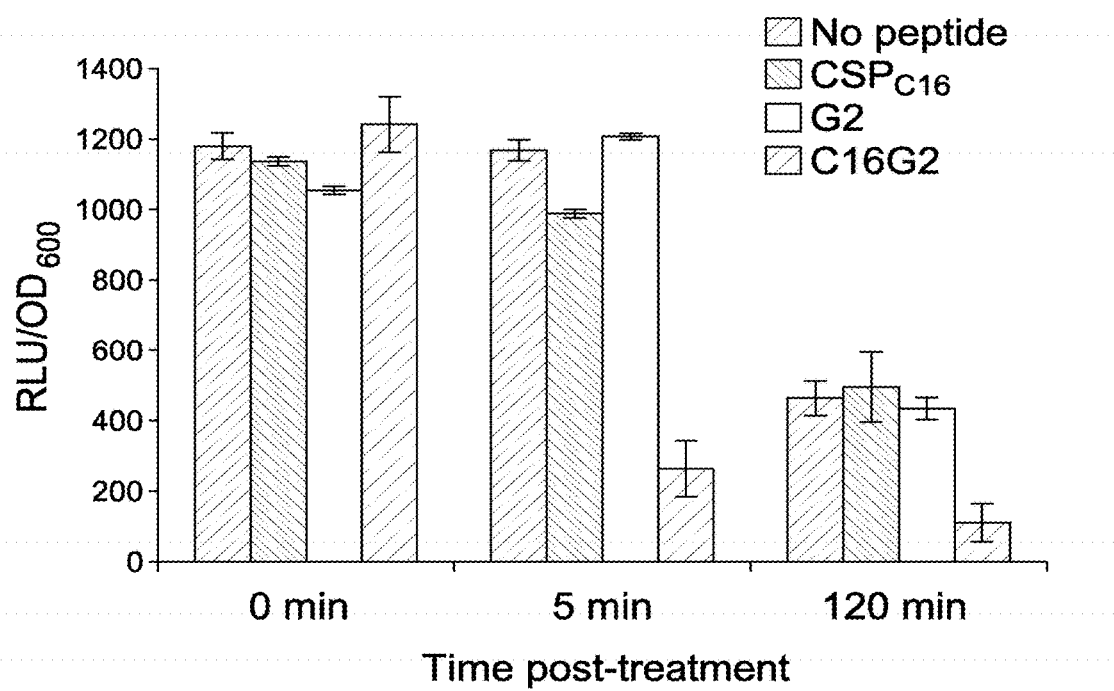
FIG. 3: C16G2 activity against *S. mutans* within a multi-species biofilm. Mixed cultures of *S. mutans*, *S. sanguinis*, and *S. gordonii* were allowed to form a biofilm in saliva and were then exposed to 25 μM C16G2, $CSP_{C16}$, or G2. After washing, the biofilms were allowed to recover in fresh medium/saliva. The regrowth of the biofilm over time was monitored by measuring absorbance at $OD_{600}$, while the health of the *S. mutans* within the biofilm was measured by luciferase activity (RLU production). The data were plotted as $RLU/OD_{600}$ and represent averages of at least 3 independent experiments.

1.9 C16G2 can selectively eliminate *S. mutans* from a mixed species biofilm. In addition to growing as biofilm in vivo, *S. mutans* are also constantly bathed in saliva as they adhere to the tooth surface. To examine whether C16G2 could selectively kill *S. mutans* under these conditions, 2 species of non-cariogenic oral streptococci (*S. gordonii* and *S. sanguinis*), were mixed with *S. mutans* JM11, a strain harboring a transcriptional fusion between luciferase (luc) and the promoter for the constitutively active gene lactate dehydrogenase (ldh), which has the same susceptibility to C16G2 as the wild type UA159. JM11 has been previously utilized to measure the fitness of *S. mutans* populations, and decreasing relative light unit (RLU) production was shown to strongly correlate with reduced cell viability (Merritt et al., 2005). The mixed-species biofilms were formed with saliva, and then peptides (25 µM) suspended in saliva were added for 5 min and removed, and the post-treatment growth of the biofilm was further monitored. The number of viable *S. mutans* cells within the biofilm was quantified in parallel by luciferase expression. It was found that C16G2 was able to dramatically reduce the *S. mutans* population within the mixture (reflected in the low luciferase activity) after 5 min exposure, compared to $CSP_{C16}$ and G2 (FIG. 3). Interestingly, even after 120 min post treatment, the total number of *S. mutans* within the mixture remained low (FIG. 3). Taken together, these results indicate that a short exposure of C16G2 is capable of selectively inhibiting the growth of *S. mutans* within a multi-species biofilm and in the presence of saliva for a minimum of 2 h without harming bystander bacteria or affecting the overall health of the biofilm.

1.10 Enhanced antimicrobial activity of C16G2 is related to targeted ComD-independent binding of $CSP_{C16}$ to *S. mutans*. To further explore the mechanism of C16G2 enhanced activity against *S. mutans*, $CSP_{C16}$ and C16G2 were fluorescently labeled and tested their ability to bind *S. mutans* and other streptococci. Consistent with observed killing activity, it was found that $CSP_{C16}$ and C16G2 could specifically bind to *S. mutans* with a very short time exposure (1-2 min), but not to other oral streptococci (data not shown). Previous genetic studies suggested that CSP may interact with ComD to activate DNA competence in *S. mutans* (Li et al, 2001). It was unexpected to find that a similar MIC was observed for UA159 and the comD strain (Table 3). Consistent with this observation, it was also found that fluorescent labeled $CSP_{C16}$ and C16G2 bound to UA159 and the comD mutant in a similar manner, indicating that the specific binding ability of CSP to *S. mutans* is independent of ComD.

1.11 M8G2 has similar anti-*S. mutans* activity as C16G2. Based on the data above, it was hypothesized that $CSP_{M8}$ would be sufficient to function as an alternative targeting domain for an anti-*S. mutans* STAMP. To test this hypothesis, $CSP_{M8}$ and G2 were synthesized together to form the STAMP M8G2 (Table 1). As shown in Table 3, M8G2 displayed similar MICs against *S. mutans* and other oral streptococci when compared to C16G2. Furthermore, single-species biofilm inhibition assays showed that M8G2, like C16G2, was capable of inhibiting the recovery of *S. mutans* biofilms (FIG. 4A), but not those of *S. sanguinis* (FIG. 4B), after 1 min exposure. Since the $CSP_{M8}$ domain is much smaller than $CSP_{C16}$ and consequently easier to chemically synthesize, these results provide a basis for a future design of shorter anti-*S. mutans* STAMPs based on $CSP_{M8}$.

Figure 5:
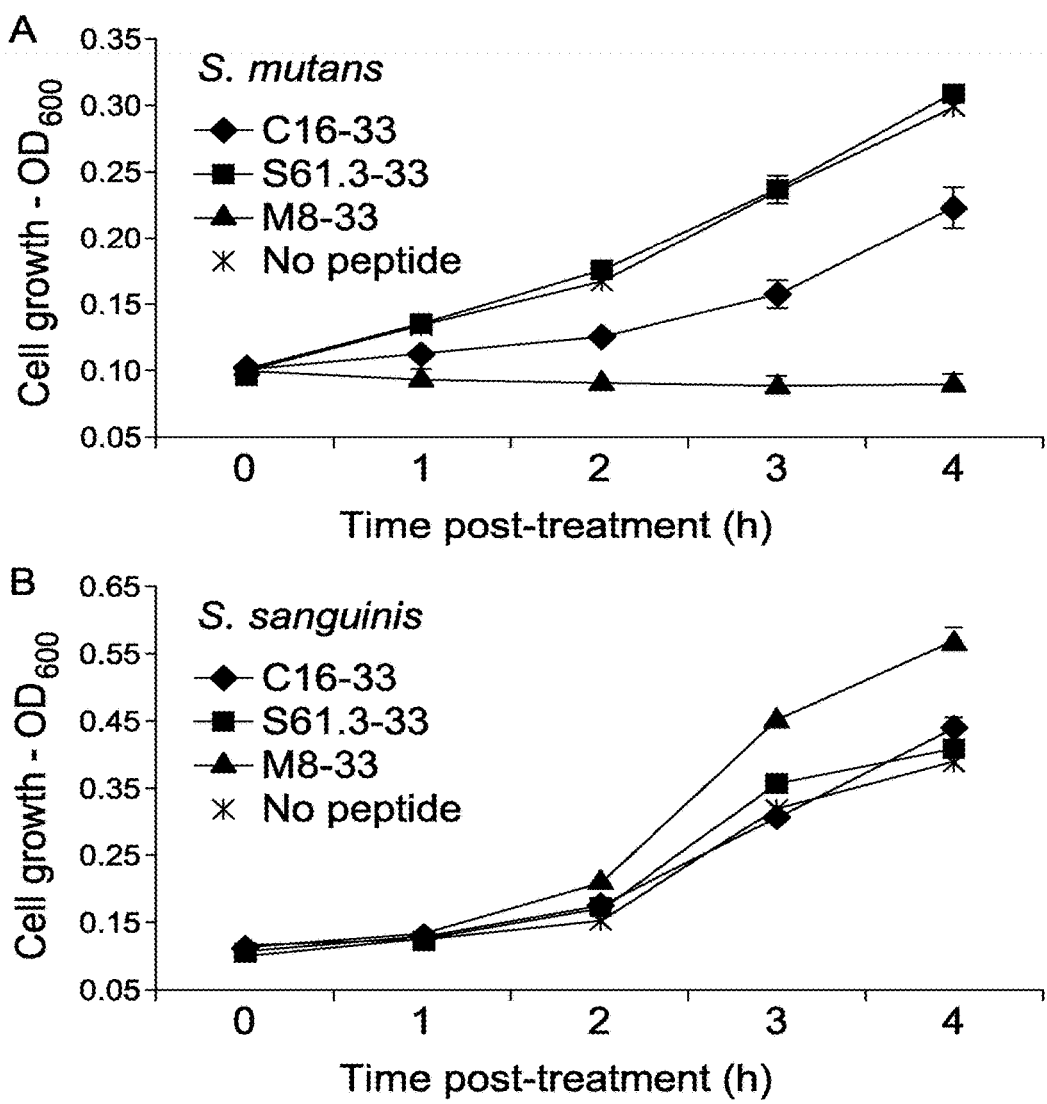
FIG. 5: Biofilm inhibitory activity of S6L3-33 and S6L3-33-containing STAMPs. Single-species biofilms of *S. mutans* (A) or *S. sanguinis* (B) were treated with M8-33, C16-33 or S6L3-33 alone (specified in the figure) for 1 min. After agent removal and stringent washing, the regrowth of the biofilms was tracked over 4 h by measuring absorbance at $OD_{600}$ after the addition of fresh medium. The data represent an average value obtained from at least 3 independent assays.

1.12 $CSP_{C16}$/$CSP_{M8}$-guided STAMPs are functional with an alternative killing domain. Since the targeting and antimicrobial components of a STAMP are functionally independent, despite being synthesized as one peptide (Eckert et al, 2006), it was reasoned that a combination of $CSP_{C16}$ or $CSP_{M8}$ with a different general antimicrobial peptide could also result in increased killing activity and selectivity towards *S. mutans* when compared with the untargeted killing peptide alone. Therefore, both targeting peptides were conjugated to S6L3-33, a model wide-spectrum antimicrobial peptide, in a similar arrangement as C16G2 and M8G2, to yield the STAMPs C16-33 and M8-33 (Table 1). As shown in Table 4, a 2-3 fold difference in MIC between S6L3-33 and the derived STAMPs was observed against *S. mutans* and the other oral streptococci tested. However, when single-species biofilm studies were conducted (shown in FIG. 5), the *S. mutans*-selective activity of the STAMPs was readily apparent: both C16-33 and M8-33 were capable of retarding *S. mutans* biofilm growth after a short exposure (FIG. 5A), while cultures of *S. sanguinis* were not affected by STAMP administration (FIG. 5B). These results indicate a clear enhancement of STAMP activity selective for *S. mutans* biofilms.

TABLE 4

MIC of STAMPs constructed with the S6L3-33 antimicrobial region. MICs represent averages of at least 3 independent experiments with standard deviations.

| Peptide | MIC (μM) | | | |
|---|---|---|---|---|
| | UA159 | comD | S. sanguinis | S. gordonii |
| S6L3-33 | 7.0 ± 3.0 | 6.5 ± 2.5 | 40 ± 7.5 | 20 ± 5.0 |
| C16-33 | 2.5 ± 2.1 | 2.2 ± 0.5 | 13.3 ± 5.8 | 14.6 ± 5.0 |
| M8-33 | 2.5 ± 2.0 | 2.5 ± 2.0 | 20 ± 2.0 | 10 ± 2.5 |

In general, a series of STAMPs which exhibited specificity for S. mutans and not other oral streptococci were synthesized and evaluated. The STAMPs were designed for S. mutans-selective activity by incorporating portions of a natural pheromone produced by these cariogenic bacteria (CSP) as the targeting domain within the linear STAMP peptide. By exclusively utilizing short (<3 kD) linear peptides for the targeting and antimicrobial regions, we were able to rapidly synthesize and isolate the complete STAMP molecule in once piece via solid-phase chemical methods, a distinct advantage over the recombinant expression and difficult purification routes necessary to construct the large (>70 kD) protein-based targeted antimicrobials that have been described (Qiu et al. 2005). Additionally, the flexibility provided by synthetic routes enabled us to easily increase STAMP diversity by switching between different combinations of targeting domains ($CSP_{M8}$ and $CSP_{C16}$) and killing domains (G2 and S6L3-33) when constructing STAMPs against S. mutans, a task that would otherwise require tedious cloning procedures.

As shown in FIG. 5, $CSP_{C16}$ and $CSP_{M8}$ were able to be conjugated to an alternative antimicrobial peptide (S6L3-33) without the loss of S. mutans selective killing ability. This finding further validates the notion that the STAMP targeting and antimicrobial domains function independently, and are capable of being linked in different combinations without the loss of activity. This suggests that future STAMP construction will be an unlimited "tunable" process whereby a myriad of combinations of antimicrobial, linker and targeting domains can be synthesized in order to select a STAMP with the best specific activity. Furthermore, bacterial STAMP resistance (should it evolve) (Perron et al, 2006) could be easily overcome by switching to alternative, functionally analogous STAMP components, as was done with G2 and S6L3-33 in this study. Additionally, peptide pheromones are widely utilized by pathogenic bacteria especially Gram-positive organisms, and therefore represent a large and growing pool from which future targeting peptides could be selected for STAMP construction.

C16G2, M8G2, C16-33 and M8-33 displayed robust specific activity against targeted S. mutans bacteria in planktonic cultures and in biofilms with both single and multi-species, suggesting that we were able to construct a set of functional STAMPs that can discriminate between S. mutans and other non-cariogenic oral streptococci. This selective activity, combined the low cytotoxicity of these peptides (Eckert, et al, unpublished data) indicates that they are useful for anti-caries therapeutic development. Currently, treatments for S. mutans infection include abstinence from dietary sugars, mechanical removal of the dental plaque, and general biocide mouthwashes. While all are temporarily effective to varied degrees, the unavoidable loss of normal flora that occurs with mechanical removal or general antibiotic treatment allows S. mutans to re-establish a niche in the oral cavity without difficulty (Caufield et al., 2000). Therefore, a STAMP with a pathogen-selective (e.g., S. mutans-selective) killing ability is an ideal solution which selectively kills or reduces the pathogen (e.g., S. mutans) in the flora and allows the normal flora to outgrow affected S. mutans populations. Such an "antibiotic-probiotic" therapeutic will help prevent dental caries progression and the high health care costs associated with this disease (Anderson & Shi, 2006).

Example 2. Enhancement of Antimicrobial Activity Against Pseudomonas aeruginosa by Co-Administration of G10KHc and Tobramycin 2.1 Pseudomonas aeruginosa is a common opportunistic human pathogen that is associated with life-threatening acute infections and chronic airway colonization during cystic fibrosis. In the US Patent Application Publication NO. 20040137482, novispirin G10, a wide-spectrum antimicrobial peptide was converted into a selectively-targeted antimicrobial peptide (STAMP), G10KHc. Compared to novispirin G10 the G10KHc STAMP had an enhanced killing ability against Pseudomonas mendocina. In this experiment, we explored the antimicrobial activity of G10KHc against P. aeruginosa and a synergistic enhancement in killing activity when the G10KHc STAMP was co-administered with tobramycin.

2.2 The G10KHc STAMP and its components. G10Hc STAMP has the following sequence and components:

```
G10KHc [targeting peptide-linker peptide-
antimicrobial peptide, the linker is underlined]:
                                    (SEQ ID NO 36)
KKHRKHRKHRKHGGSGGSKNLRRIIRKGIHIIKKYG G10 (Novispirin) antimicrobial peptide:
                                    (SEQ ID NO 35)
KNLRRIIRKGIHIIKKYG Cat-1(also called KH) targeting peptide:
                                    (SEQ ID NO 31)
KKHRKHRKHRKH Linker peptide:
                                    (SEQ ID NO 28)
GGSGGS.
```

Figure 6:
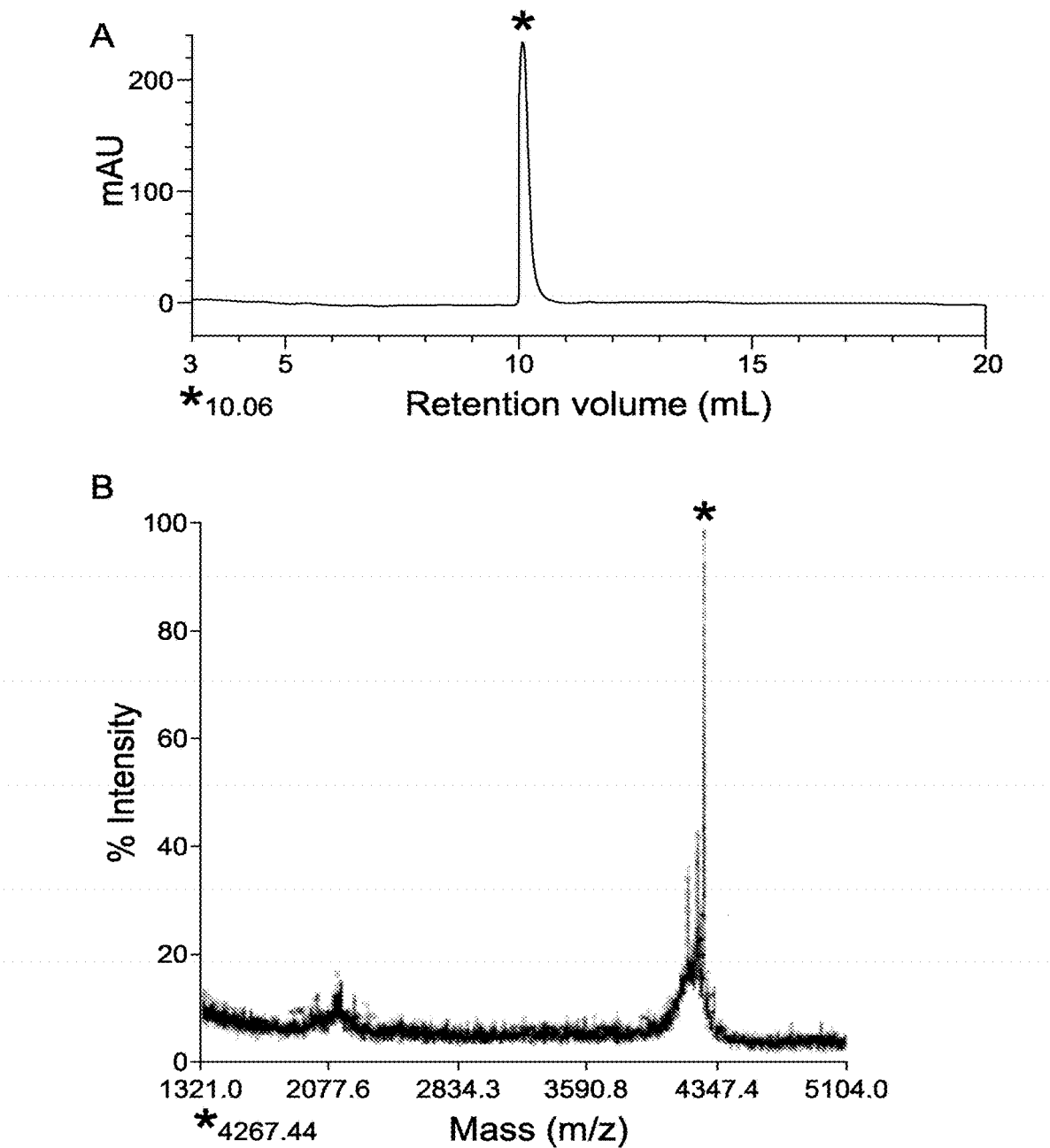
FIG. 6: HPLC and MALDI spectra for G10KHc. The quality of purified G10KHc was assessed by HPLC (a) and MALDI mass spectrometry (b). By monitoring UV 215, a single peak was detected during HPLC (at 10.06 mL) that had the correct mass for G10KHc (4267.44).

Solid-phase peptide synthesis of G10 (KNLRRIIRKGIHIIKKYG, SEQ ID NO 35) and G10KHc (KKHRKHRKHRKH-GGSGGS-KNLRRIIRKGIHIIKKYG, SEQ ID NO 36) was carried out using the Fast-Fmoc (9-fluorenylmethoxycarbonyl) methodology on a 431A Peptide Synthesizer (Applied Biosciences). Completed peptides were cleaved from the resin using 95% TFA with the appropriate scavengers. Peptide mass was confirmed by matrix-assisted laser desorption/ionization (MALDI) mass spectroscopy (Voyager System 4291, Applied Biosystems) and crude peptides purified by reverse-phase high-pressure liquid chromatography (HPLC, ACTA Purifier, Amersham) while monitoring UV 215. The mobile phase during HPLC consisted of water/acetonitrile (with 0.1% trifluoroacetic acid) at a flow rate of 0.5 mL/min (Source 15 RPC column, Amersham). The HPLC and MALDI profiles for purified G10KHc are shown in FIG. 6. Specifically, after purification, a single peak for G10KHc was observed at retention volume 10.06 mL (FIG. 6A), which was found to have the expected mass for G10KHc (predicted 4267.08, observed 4267.44) as shown in FIG. 6B.

2.3 Antimicrobial Activities. The general antimicrobial activities of G10KHc, G10, and tobramycin against clinical isolates of P. aeruginosa were evaluated by minimum inhibitory concentration (MIC) assay as previously described (Eckert et al., 2006) and shown in Table 5. MICs are reported in µM, though for familiarity, 1 µM tobramycin=0.468 µg/mL. P. aeruginosa were grown to log phase and adjusted to ~1×10$^5$ cfu/mL in Mueller-Hinton (MH) broth and added to 96-well plates. Two-fold serial dilutions of peptide were then added to bacteria and the plates incubated for 18-24 hours at 37° C. MIC was determined as the concentration of peptide present in the last clear well (no growth). As expected, G10KHc was significantly more active against the P. aeruginosa clinical isolates when compared with G10 alone (Student's t test, p=0.001): the MICs for G10KHc ranged from 0.5 to 29 µM (mean 622 µM), compared with the MICs for G10, which ranged from 10 to 60 µM (mean 23.4 µM). Since the KH domain (or the Cat-1 peptide) itself does not have any antimicrobial activity, the increased anti-P. aeruginosa activity of G10KHc is likely due to the targeted binding ability of KH to Pseudomonas spp, as previously reported (Eckert et al., 2006). In contrast to tobramycin, G10KHc was also effective against aminoglycoside and multiple-antibiotic resistant P. aeruginosa isolated from CF patients (AGR10, MR15). Additionally, as mucoid P. aeruginosa are often associated with reduced susceptibility to antimicrobial agents, we were encouraged to find that G10KHc was active against one such strain, PDO300. Overall, G10KHc was not as active as tobramycin against the sensitive isolates examined (typically 1-2 dilution steps less effective).

TABLE 5

MICs of tobramycin, G10, and G10KHc against P. aeruginosa lab and clinical isolates. The average MIC from at least 3 independent experiments is shown. The KH targeting domain alone does not have any antimicrobial activity (data not shown). For reference, 1 µM tobramycin = 0.468 µg/mL.

| Strain | MIC (µM) | | |
|---|---|---|---|
| | G10KHc | novispirin G10 | tobramycin |
| PAO1 | 6 | 23 | 2.5 |
| PA14 | 5.5 | 10 | 0.7 |
| PAK | 5.5 | 13 | 2.12 |
| PDO300* | 6 | 45 | nt |
| ATCC 15692 | 6 | 16 | 3.05 |
| ATCC 27583 | 6 | 16 | 1.75 |
| ATCC 10145 | 4.5 | 14.5 | 1.75 |
| ATCC 9027 | 5.5 | 15 | 2.12 |
| AGR10 | 1.1 | 18 | 55 |
| MR15 | 0.5 | 14 | 55 |
| S40 | 29 | 60 | 0.4 |
| S60 | 3.13 | 30 | 0.4 |
| S100 | 1.1 | 30 | 3.5 |

*mucoid phenotype,
nt: not tested

Time-Kill (killing kinetics) experiments were performed essentially as described previously (Eckert et al., 2006). Briefly, P. aeruginosa were grown to log phase and diluted to ~1×10$^5$ cfu/mL (moderate density planktonic cultures) in LB with 30% mouse serum (MP Biomedicals) prior to the addition of 10 µM tobramycin, G10 or G10KHc to the cell suspensions. At each time point, 10 µL of the culture was removed and P. aeruginosa cells rescued by dilution in 500 µL LB and kept on ice until plating. Surviving cfu/mL were quantitated after plating on LB agar and incubating overnight at 37° C. under aerobic conditions.

Figure 7:
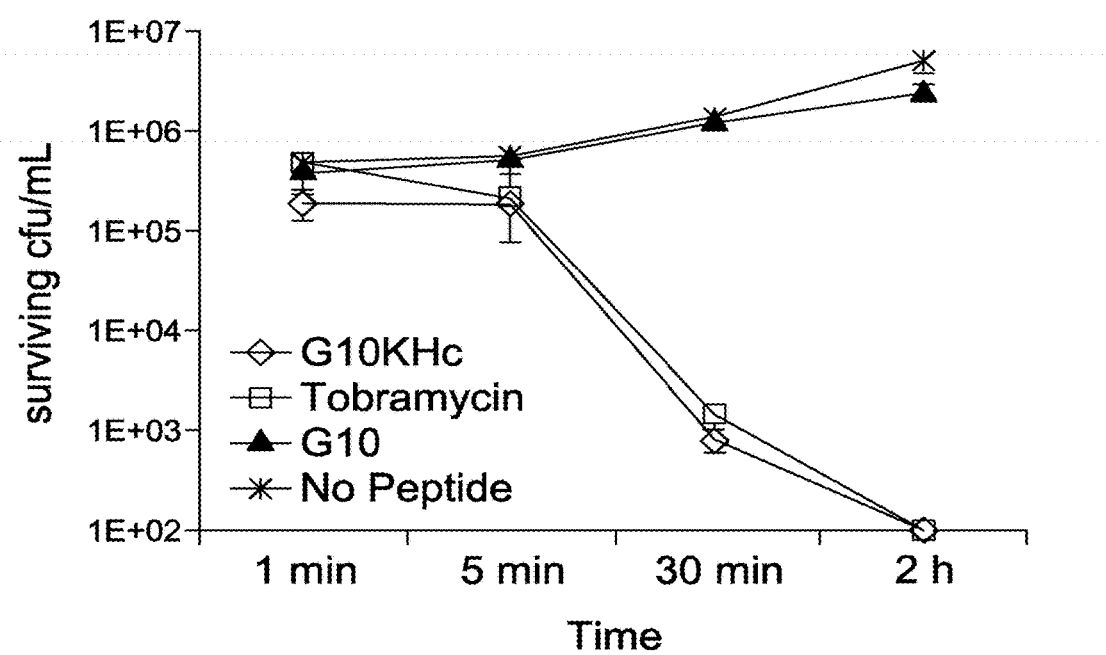
FIG. 7: Antimicrobial kinetics of G10KHc, G10, and tobramycin. *P. aeruginosa* strain ATCC 15692 was either mock treated or challenged with the STAMP G10KHc, untargeted G10, or tobramycin (10 μM) and the surviving cfu/mL quantitated after 1 min, 5 min, 30 min and 2 h. The assay was conducted in 30% mouse serum and represents the average of at least three independent experiments.

As shown in FIG. 7, the killing kinetics assay revealed that G10KHc had an obvious improvement in killing versus G10 against P. aeruginosa: 10 µM G10KHc treatment of the cultures was associated with a decrease in viable P. aeruginosa (to under 100 cfu/mL by 30 min), while G10 was ineffective over the time course examined. The rate of G10KHc antimicrobial activity was similar to an equimolar dosage of tobramycin (4.68 µg/mL). These results suggest that G10KHc and tobramycin have similar potency against clinical isolates as well as lab strains, and that G10KHc can inhibit the growth of drug-resistant P. aeruginosa. Furthermore, the data indicate that G10KHc appears to require the KH Pseudomonas spp targeting domain for effective P. aeruginosa cell killing: G10 alone showed poor activity unless incubated 18-24 h (Table 5).

2.4 Synergistic killing effect of G10KHc and tobramycin. For evaluation of enhanced activity between G10KHc and tobramycin against high density planktonic cultures, ATCC 15692 were grown overnight were adjusted to ~1×10$^8$ cfu/mL in ddH$_2$O (pH 7.4) and exposed to 5 µM tobramycin, 5 µM G10KHc or a combination of both agents (a combination of 5 µM tobramycin (2.34 µg/mL) and 5 µM G10KHc or G10). 10 µL of the treated cultures was rescued by dilution after 24 h and the surviving cfu/mL plated on LB and counted after growth on LB agar.

Figure 8:
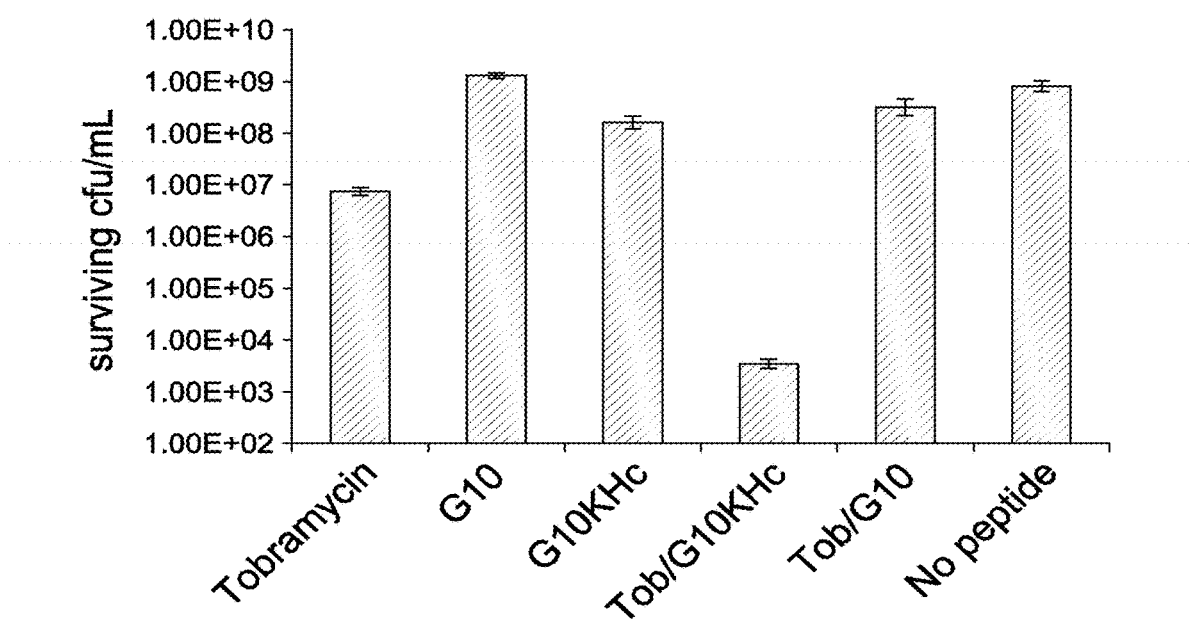
FIG. 8: Time-kill assay against high-density planktonic *P. aeruginosa*. Cultures ($1\times10^8$ cfu/mL) were exposed to 5 μM G10KHc or G10 with and without equal molar tobramycin co-treatment, as well as administered tobramycin alone. After 24 h, surviving cfu/mL were determined by plating. Data points represent the averages of three independent experiments.

As shown in FIG. 8, we observed a clear enhancement in killing activity when tobramycin and the STAMP (but not G10) were co-administered. Surviving cfu/mL from co-treated cultures (~1×10$^3$ cfu/mL) were 5 log$_{10}$ lower than the level recovered from untreated cultures (~1×10$^8$ cfu/mL) or those exposed to either tobramycin or G10KHc (1×10$^7$ cfu/mL and ~1×10$^8$ cfu/mL, respectively). These results suggest that when applied together, these agents are markedly more effective against planktonic P. aeruginosa than either constituent singly and can eliminate nearly all of a high cell-density culture by 24 hours, even when G10KHc was administered at a concentration below the MIC for the tested strain.

2.5 Synergistic killing effect of G10KHc and tobramycin on biofilm. A synergistic killing effect between tobramycin and G10KHc was also observed against biofilm-associated P. aeruginosa. In this experiment, a rotating-disk biofilm reactor system was used for generating quantitative data on biofilm susceptibility to tobramycin, G10 and G10KHc. The system consisted of a reactor vessel containing 250 mL of diluted trypticase-soy broth (TSB) (1:100) medium. Reactors were inoculated with overnight cultures (1%, v/v). After static overnight growth in TSB, a flow of fresh medium was initiated (dilution rate, 0.7 h$^{-1}$). After 24 h in a flow of medium, the polycarbonate chips with attached biofilm bacteria were aseptically removed from the spinning disk and washed three times in ddH$_2$O (pH 7.4) and incubated in 1 mL ddH$_2$O. G10 (100 µg/mL), G10KHc (100 µg/mL), tobramycin (100 µg/mL), or a combination of the two was added as indicated. The chips were then incubated for 4 or 24 h in 24-well tissue culture plates (Falcon no. 353047; Becton Dickinson Labware, Franklin Lakes, N.J.). To estimate the number of viable P. aeruginosa remaining, the disks were placed in 1 mL PBS and the cells were dispersed using a tissue homogenizer (Brinkmann Instruments, Westbury, N.Y.) and the total cfu per chip was determined by serial dilution and plating on LB agar.

Figure 9:
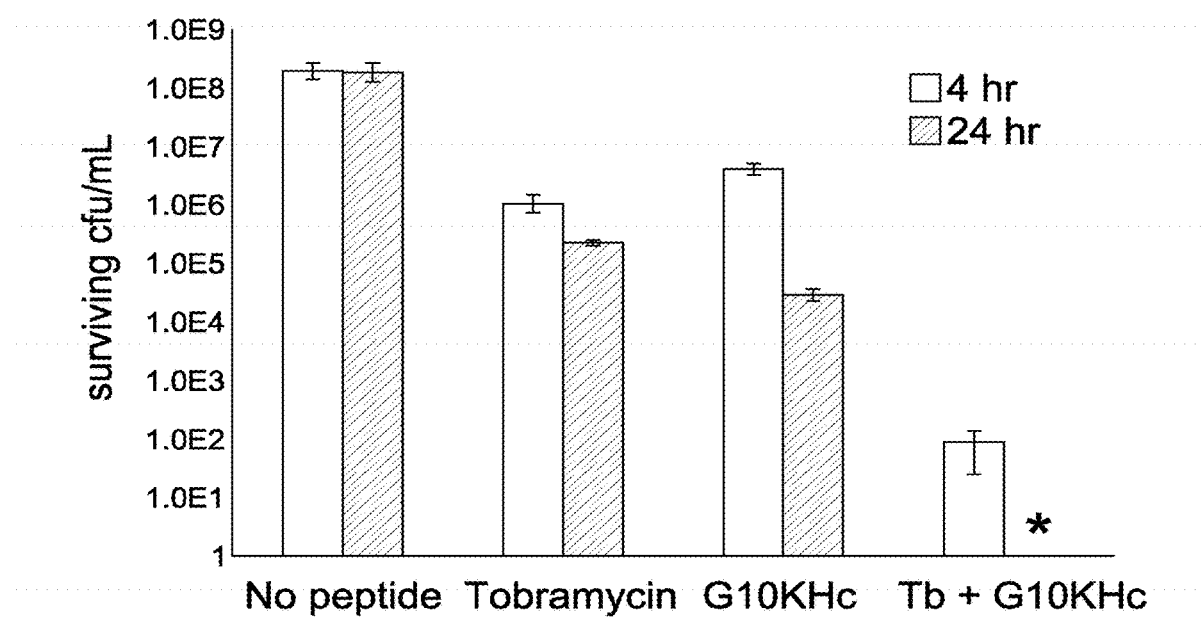
FIG. 9: Enhanced antimicrobial activity of G10KHc and tobramycin against biofilm *P. aeruginosa*. Biofilms were grown on disk reactors and challenged with 100 μg/mL of agent as indicated. After 4 and 24 h, surviving bacteria were harvested and plated for quantitation from at least 3 independent experiments.

As shown in FIG. 9, 100 µg/mL G10KHc or 100 µg/mL tobramycin alone had very limited killing effects against P. aeruginosa biofilms after 4 h or even 24 h. However, the combination of 100 µg/mL G10KHc and 100 µg/mL tobramycin dramatically reduced the level of surviving cfu/mL after 4 h, a 4 $\log_{10}$ improvement in killing ability when compared to either agent alone. More strikingly, no cfu/mL were recovered when the combined agents were co-incubated with *P. aeruginosa* for 24 h (a decrease of nearly 5 $\log_{10}$ from individual applications). These data indicate a strong enhancement in killing activity when G10KHc and tobramycin are used against in vitro *P. aeruginosa* biofilms. Additionally, these results were consistent with FIG. 8, suggesting that G10KHc and tobramycin may be synergistic against *P. aeruginosa* in planktonic or biofilm modes of growth, though further experiments are necessary to fully establish synergistic activity.

2.6 G10KHc mediated membrane permeability. The results from FIGS. 8 and 9 suggest that the rate of tobramycin cell killing could be increased by G10KHc co-treatment. In the absence of peptide, robust bacterial uptake of tobramycin is an active process that requires an intact $\Delta\Psi$ gradient (electric potential of the proton motive force) which is maximized during aerobic respiration. This process may be slowed or eliminated in anoxic environments, (such as the interior of biofilms), suggesting that tobramycin diffusion across *P. aeruginosa* membranes (or lack thereof) is critical to at least one mechanism of aminoglycoside tolerance in these bacteria (14, 33, 40). Therefore, due to the membrane-disrupting AMP domain in G10KHc and its previously described anti-outer membrane activity (11), it was contemplated that G10KHc was permeabilizing the *P. aeruginosa* outer and inner membranes, enabling increased tobramycin uptake and leading to the observed synergy.

In order to confirm that G10KHc-membrane disruption could mediate cellular accumulation of a small molecule, overnight cultures of *P. aeruginosa* were diluted 1:50 in LB and grown to log phase (3-4 h, ~1×10$^5$ cfu/mL) prior to mock treatment or treatment with 2 µM G10KHc. After 5 min, membrane-compromised cells were stained with propidium iodide (PI) (LIVE/DEAD Baclight Viable Stain, Invitrogen) in the presence or absence of sub-lethal G10KHc concentrations (2 µM) in accordance with the manufacturer's protocol. PI is a small molecule dye that binds double stranded DNA and fluoresces red upon excitation and was used as a surrogate for tobramycin as the internalization of an aminoglycoside is not easily assayable. The dye cannot cross an intact cytoplasmic membrane and is commonly used for cell viability analysis. Dye intercalation into DNA (red stain), was detected by fluorescence microscopy (Nikon E400) at a 40× magnification. Brightfield and red fluorescence images were collected using the factory default settings (SPOT, Diagnostics). To determine bactericidal activity after peptide treatment and PI staining, samples prepared in parallel to visualized cultures were plated on LB agar after 1:5 serial dilutions. Images of surviving cfu/mL were taken with a GelDoc (BioRad) using QuantityOne software.

It was expected that G10KHc-induced membrane disruption would lead to an increase in nucleic acid staining when compared to PI alone. As shown in FIG. 10, bacteria treated with PI alone remained unstained. In comparison, intracellular PI staining was clearly visible in cultures exposed to PI and G10KHc. Additionally, the amount of red fluorescence observed was proportional to the amount and length of G10KHc treatment (data not shown). To ensure that we were not simply staining *P. aeruginosa* killed by G10KHc, the viable cfu/mL were evaluated from the visualized cultures. From the serial dilutions shown below the images in FIG. 10, it was clear the number of viable *P. aeruginosa* recovered was similar between cultures treated with PI alone or PI/G10KHc. Overall, these data suggest that a sub-lethal dosage of G10KHc can induce membrane damage and promote the uptake of small molecules, such as tobramycin or PI into metabolically active *P. aeruginosa* cells.

2.7 Conclusion. In general, In this study, we explored the antimicrobial activity of G10KHc against *P. aeruginosa*. G10KHc was found to be highly active (equal to tobramycin) against *P. aeruginosa* clinical isolates. Most interestingly, we observed a synergistic-like enhancement in killing activity when biofilms and planktonic cultures of *P. aeruginosa* were co-treated with G10KHc and tobramycin. The data indicate that the mechanism of enhanced activity may involve increased tobramycin uptake due to G10KHc-mediated cell membrane disruption. These results suggest that G10KHc may be useful against *P. aeruginosa* during acute and chronic infection states, especially when co-administered with tobramycin.

*P. aeruginosa* is a persistent and recurrent opportunistic pathogen responsible for life-threatening recurrent infections during CF. Frequent isolation of antibiotic-resistant *P. aeruginosa* suggests that it is critical that new therapies be developed to inhibit and treat *P. aeruginosa* colonization of airway mucosal surfaces before currently-prescribed treatment options are no longer effective.

Figure 4:
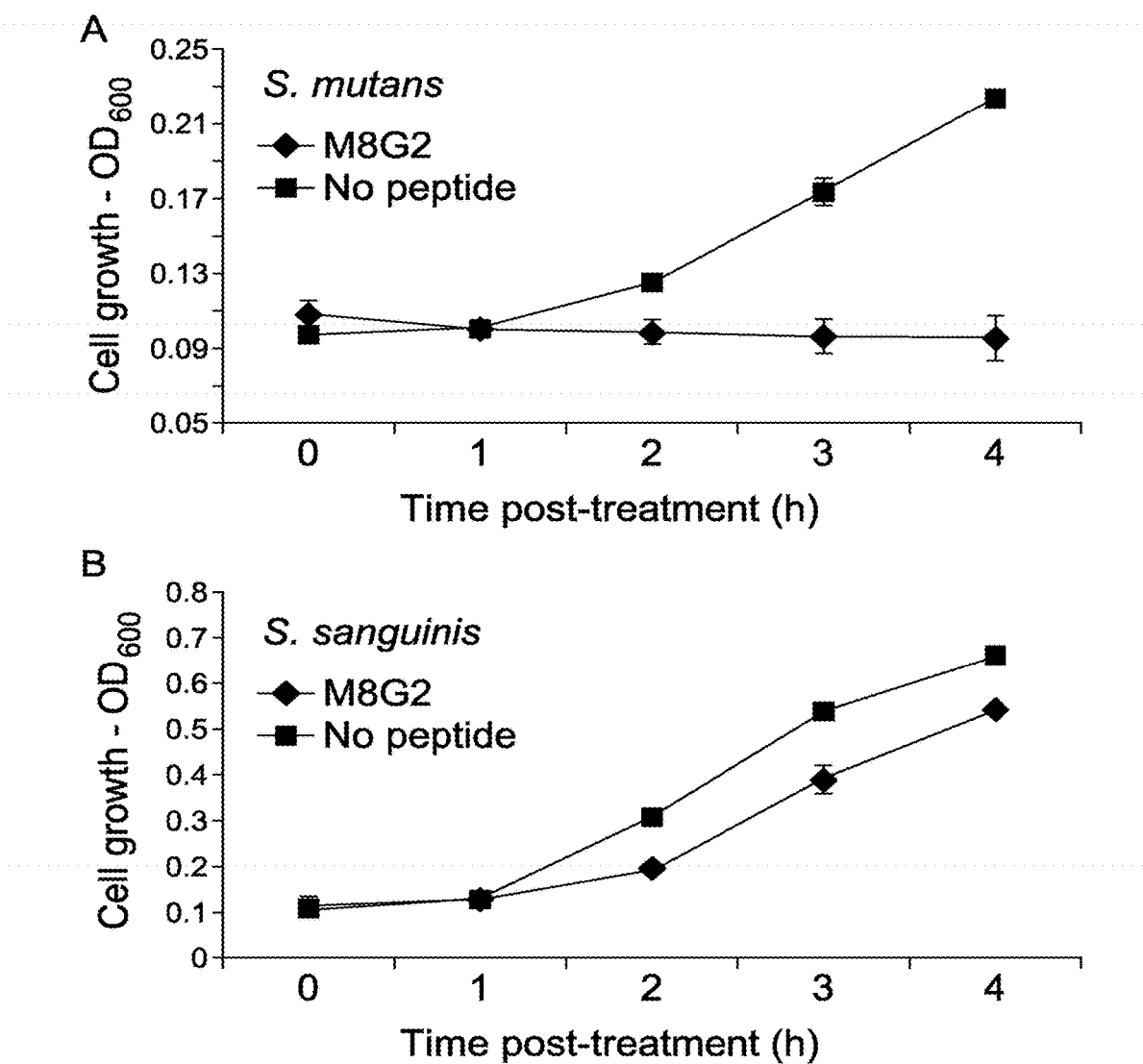
FIG. 4: Activity of M8G2 against oral bacteria in biofilms. *S. mutans* (A) or *S. sanguinis* (B) single-species biofilms were mock-treated or exposed to 25 μM M8G2 (specified in the figure). After removal of the STAMP and the addition of fresh medium, biofilm recovery was monitored over time by monitoring absorbance at $OD_{500}$. The data represent the average of 3 independent experiments.

This experiment shows that G10KHc is markedly improved in comparison to its wide-spectrum parent peptide G10, and is similar to that of tobramycin. Additionally, G10KHc is effective against high density planktonic cultures and *P. aeruginosa* biofilms in vitro (FIG. 3-4). When compared to tobramycin, G10KHc was nearly 10-fold more effective per µM at reducing biofilm viability (100 µg/mL tobramycin=213 µM, 100 µg/mL G10KHc=23.5 µM). Against high-density planktonic cells, however, 5 µM (2.34 µg/mL) tobramycin alone was markedly more bactericidal than either 5 µM G10 or G10KHc after 24 hours (1-2 $\log_{10}$ improvement). The difference in tobramycin activity may be linked to the anaerobic environment found at the interior of *P. aeruginosa* biofilms, which inhibits robust aminoglycoside cellular uptake.

The highest level of anti-*P. aeruginosa* activity observed in planktonic or biofilm cultures occurred when both agents were applied together. Co-administered tobramycin and G10KHc resulted in a marked enhancement of killing activity: nearly 10,000-fold more bacteria were eliminated by co-treatment than by either agent alone in planktonic and biofilm cultures. Though additive and synergistic anti-*P. aeruginosa* activity has been described between an antimicrobial peptide and tobramycin (Saiman et al., 2001), as well as tobramycin plus numerous other conventional small-molecule antibiotic (Bonacorsi et al., 1999), the current experiment represents the first reported example of biofilm-associated *P. aeruginosa* being synergistically or additively eliminated by an aminoglycoside/peptide combination.

Aerosolized tobramycin has been approved for the control of *P. aeruginosa* infections in CF patients, and not unexpectedly, tobramycin and aminoglycoside-resistant strains of *P. aeruginosa* and other organisms have been isolated from CF sputum. This fact, combined with the relatively high rate of unpleasant post-treatment dyspnea, bronchospasm, and increased cough, suggests that tobramycin may be best utilized in a smaller dosage size in combination with another agent. It is concluded that G10KHc can be a candidate for co-administration due to its engineered *Pseudomonas* selectivity, and potent antimicrobial effects against *P. aeruginosa* biofilms and multi-drug and aminoglycoside-resistant strains.

Example 3. Enhanced Stability and Activity of the G10KHc STAMP by Using D-Amino Acid Enantiomer to Synthesize the STAMP and/or Chemical Antagonists (e.g., rhDNase)

3.1 Material preparation and methods. G10KHc (KKHRKHRKHRKH-GGSGGS-KNLRRIIRKGIHIIK-KYG, SEQ ID NO 36, [targeting domain-linker-antimicrobial domain]), and the D-enantiomer G10KHc-D were synthesized by Fast-Fmoc (9-fluorenylmethoxycarbonyl) methodology on a 431A Peptide Synthesizer (Applied Biosciences), as described previously (Eckert et al., 2006), using D-amino acids for G10KHc-D purchased from Anaspec (San Jose, Calif.).

Eight expectorated sputum samples from different patients were obtained from patients with CF at Children's Hospital Los Angeles (Los Angeles, Calif., USA) during routine clinical practice and stored at −80° C. within 1 h of collection. Sputum sample collection for this study was approved by the institutional review board at Children's Hospital Los Angeles (CCI #05-00040). All personal identifiers, including age, gender and prognosis, were unknown to our laboratory.

3.2 Activity and stability of G10KHc and G10KHc-D in sputum. Determination of peptide antimicrobial effects or activity in sputum was investigated in a similar manner to previous reports (Sajjan et al., 2001). To assay the activity of G10KHc and G10KHc-D against exogenous *P. aeruginosa* in sputum, collected sputum samples were diluted 1:10 in 10 mM PBS (PBS) and pooled (referred to as pooled sputum). In 100 μL pooled sputum, ATCC 15692 was added to a final concentration of 5×10⁶ cfu/mL prior to 25 μM peptide addition.

In samples examining the effect of protease inhibitors on peptide activity, pooled sputum samples were pre-treated for 30 min with 1 mM protease inhibitor, either phenylmethylsulphonylfluoride (PMSF), beta-mercaptoethanol (BME), or ethylenediaminetetraacetic acid (EDTA), (all acquired from Sigma-Aldrich), followed by addition of 25 μM G10KHc and ATCC 15692 (~5×10⁶ cfu/mL).

Bacteria surviving peptide treatment were rescued by dilution (1:50) in growth media at 4 h and kept on ice before appropriate dilution and plating on LB agar supplemented with ampicillin (25 μg/mL) After overnight incubation at 37° C., colonies were counted and the surviving cfu/mL quantitated. 100 cfu/mL was considered as the countable limit for all plating procedures. Endogenous organisms already present in the pooled sputum were observed, but were a minority of the population compared to the exogenously added cells (less than 1%, data not shown). As a result endogenous and exogenous cfu/mL were not differentiated for these cultures.

The general antimicrobial effect of G10KHc in sputum samples from CF patients was evaluated by a killing kinetics assay. As shown in FIG. 11A, at 4 h post-peptide addition G10KHc was not active against exogenously added *P. aeruginosa* when mixed with pooled sputum samples. This finding was in contrast to G10KHc activity in growth medium, were the G10KHc STAMP was found to reduce the recoverable cfu/mL over 90% after 30 min of exposure, and eliminate all *P. aeruginosa* cfu/mL by 2 h of treatment (See Experiment 2).

Considering it likely that the loss of G10KHc activity was due to degradation, the G10KHc STAMP stability in sputum was examined over time. Stability of peptides in sputum was monitored by HPLC. Briefly, pooled sputum samples were diluted 1:10 in PBS and centrifuged repeatedly to remove insoluble materials. G10KHc or G10KHc-D (100 μM) was then added to 100 μL diluted pooled sputum (with or without 1 mM PMSF pretreatment for 1 h) and mixed at room temperature. At the indicated timepoints, 20 μL 10% HCl was added to stop peptide degradation and the sample was filtered twice (0.2 μm nylon, Nunc) prior to injection to the column (Source 15 RPC, Amersham). Water/acetonitrile with 0.1% trifluoroacetic acid was used as the mobile phase and samples were eluted with a linear gradient of increasing acetonitrile composition (from 10% to ~35%) at a flow rate of 0.25 mL/min, 11.5 mL of mobile phase per run. Intact G10KHc and degradation products were monitored by UV (215 nm) and fractions collected where indicated. Collected fractions from successive runs were pooled and lyophilized overnight prior to evaluation of antimicrobial activity by the MIC assay described above. HPLC profiles were obtained using the manufacturers protocol (Unicorn, Amersham), and differentially colored and overlayed using Photoshop 7.0 (Adobe) for construction of FIG. 11B.

As shown in FIG. 11B, the signature peak (retention volume 10.29) for G10KHc was almost entirely degraded after 30 min of exposure to sputum. Several of the resultant fractions were collected and possible degradation products were identified by mass spectrometry, none of which showed an MIC below 100 μM against several clinical *P. aeruginosa* isolates (Table 6).

TABLE 6

MIC (μM) of G10KHc, G10KHc-D and sputum-digested products

|  | MIC (μM)[a] | | |
| --- | --- | --- | --- |
|  | ATCC 15692 | ATCC 9027 | ATCC 27853 |
| Synthesized Peptides: | | | |
| G10KHc[b] | 6 | 5.5 | 6 |
| G10KHc-D | 15 | 15 | 10 |
| HPLC collected fractions[c]: | | | |
| 10.29 (G10KHc) | 6 | 6 | 6 |
| 8.50 | >100 | >100 | >100 |
| 7.49 | >100 | >100 | >100 |
| 4.04 | >100 | >100 | >100 |

[a]MIC range of 3 independent experiments
[b]data previously reported included for comparison (6)
[c]Factions shown in FIG. 1B It is known in the art that the increased levels of serine proteases present in CF sputum. Thus, it was contemplated that we hypothesized that this class of proteases were responsible for the rapid G10KHc degradation observed, and that protease inhibitors could stabilize G10KHc in sputum and restore antimicrobial function. To examine this possibility, *P. aeruginosa* and G10KHc were added to pooled sputum samples pre-treated with a variety of protease inhibitors, and the surviving bacteria were quantitated. Samples treated with BME (a cysteine protease inhibitor) or EDTA (metalloprotease inhibitor) were ineffective in rescuing G10KHc activity or stability (data not shown). As shown in FIG. 11A, however, *P. aeruginosa* were effectively killed (a reduction of over 3 $\log_{10}$ in surviving cfu/mL) by the G10KHc STAMP in samples pre-treated with the general serine protease inhibitor PMSF. The inhibitor alone had only a small affect on *P. aeruginosa* viability. Accordingly, the G10KHc signal from PMSF-treated sputum remained high through 4 h when examined by HPLC (FIG. 11B). Overall these data indicate that G10KHc is active against *P. aeruginosa* in sputum when protected from serine protease degradation.

3.3 D-enantiomer G10KHc STAMP and its activity. Because of the chiral requirement of most senile proteases (Milton et al., 1992), an all D-amino acid enantiomer of G10KHc, G10KHc-D, was synthesized as an alternative means to circumvent protease activity without the use of inhibitors. G10KHc-D was synthesized by standard solid phase methods as mentioned and confirmed by mass spectrometry.

As shown in FIG. 11A, G10KHc-D reduced the level of recovered *P. aeruginosa* 3-4 $\log_{10}$ (compared to untreated samples) after 4 h of peptide exposure, indicating that G10KHc-D has a level of activity in sputum similar to that of L-G10KHc when stabilized. However, the enantiomer was less affective against *P. aeruginosa* in growth medium after 24 h (as evaluated by MIC, Table 6), suggesting that G10KHc-D and L-G10KHc do not have completely identical activities.

3.4 Effect of rhDNase on STAMP activity in sputum. Recombinant human DNase, which is commonly used during treatment of CF to reduce sputum viscosity and promote airway clearing (Fuchs et al., 1994), was added to pooled, concentrated sputum samples to determine if G10KHc/PMSF and G10KHc-D activity could be improved during co-treatment under these conditions. To determine the effect of rhDNase (Genentech, San Francisco, Calif.) on STAMP killing ability, individual sputum samples were diluted 1:2 in 100 µg/mL rhDNase, briefly vortexed, and incubated at room temperature for 10 min. Treated samples were then pooled, followed by 1 mM PMSF addition, where appropriate, and incubation for 1 h. 25 µM G10KHc or G10KHc-D was then added with ~5×10$^6$ cfu/mL ATCC 15692 and incubated 4 h. Survivors were then rescued and quantitated by plating as described above.

As shown in FIG. 12, we observed a clear enhancement of antimicrobial activity when rhDNase was utilized in conjunction with G10KHc/PMSF or G10KHc-D (fewer than 5% of untreated cfu/mL remaining), when compared to samples not treated with rhDNase (~30% of untreated cfu/mL recovered). *P. aeruginosa* were not affected by rhDNase treatment alone. These results suggest that the killing effects of G10KHc/PMSF or G10KHc-D in sputum can be further enhanced by co-treatment with a sputum mucolytic agent, which may reduce sputum viscosity and enhance peptide diffusion.

3.5 Conclusions. In general, the activity of G10KHc can be extended in expectorated sputum when protected from proteolytic cleavage, either by constructing D-version peptides and/or by co-administering a protease inhibitor and/or in combination with rhDNase. In particular, it was found that robust G10KHc STAMP activity could be maintained in expectorated sputum if serine protease-dependant digestion associated with this fluid was inhibited, either by chemical antagonists or by the construction of a D-amino acid enantiomer of G10KHc. Further it was revealed that STAMP activity in sputum can be further enhanced when samples were treated with a combination of peptide and rhDNase. The results illustrates the importance of exploring a combination therapy to treat CF, especially if protease-sensitive peptide-based agents, such as G10KHc, are used as alternatives to, or in conjunction with, conventional small-molecule antibiotics.

Experiment 4. Identification of Peptide 1903 and BD2.21 and the STAMPs Thereof

The targeting peptide 1903 was obtained by scanning the genomic sequence of *S. mutans* UA140. The predicted open reading frames (ORFs) of the publicly-available genome were examined and those ORFs that encoded for proteins under 50 amino acids were noted and re-examined after scanning the entire genome. A number of peptides predicted to be encoded by these ORFs were selected, synthesized with fluorescent labels, tested for binding to *S. mutans* biofilms. Peptide 1903 showed the binding activity to *S. mutans* and then was used to synthesize 1903 based STAMPs.

BD2.21 was rationally-designed as part of the "Beta-deletion 2" antimicrobial peptide library. A common alpha helical residue arrangement, HHCCHHCHHH(n), was replaced using mostly positive (C) and hydrophobic (H) residues at the positions indicated. There is some variability in the pattern of residues we used, and some non-hydrophobic and uncharged residues were incorporated. The replacement was limited to 3-5 cationic amino acids per peptide, and 4-7 hydrophobic residues (9 to 12 total). The antimicrobial affects of modified peptides were tested and BD2.21 showed an MIC of 5.5 uM against planktonic *S mutans*. BD2.21 was then used to synthesize BD2.21 based STAMP such as 1903-BD2.21 having an amino acid sequence of NIFEYFLE-GGG-KLFKFLRKHLL as shown in SEQ ID NO. 13 and C16-BD2.21 having an amino acid sequence of TFFRLFNRSFTQALGK-GGG-KLFKFLRKHLL as shown in SEQ ID NO 14.

Killing of single-species *Streptococcus mutans* mature biofilms. *S. mutans* biofilms were seeded with 10$^5$ cells/well and grown overnight with 1% sucrose (TH medium) in 48-well plates (final volume 400 µL). After incubation, the supernatant was removed from the biofilms and replaced with 200 µL PBS with 50 µM STAMP. PBS alone was used for the negative control (100% survival) with ethanol as the control for complete killing of the biofilms (0% survival). Biofilms were treated with peptide for 20 min, then washed 1× with PBS. To measure biofilm survival, 20 µL CellTiterBlue diluted into 160 µL TH medium was added per well. After 3-5 min, the supernatants were removed to a 96 well plate and the absorbance read at 570 nm. High absorbance at 570 indicated more substrate reduction by viable cells remaining in the biofilm. As shown in FIG. 13, the results indicate that C16-BD2.21 and 1903-BD2.21 can kill 66% and 85% of the viable *S. mutans* within the biofilm, respectively, after a treatment time of only 20 min.

Selectivity of STAMPs against multi-species biofilms of oral streptococci. To measure selectivity of STAMPs, mixed biofilms were seeded to 48-well plates. *Streptococcus mitis, S. sobrinus, S. gordonii,* and *S. sanguinis* were mixed with *S. mutans* strain JM11 (spectinomycin resistant) at a 1:1:1:1:10 ratio, total of 10$^5$ cells/well. Biofilms were grown overnight in TH medium with 1% sucrose, 1% dextrose, and 1% mannose, for 18-24 h. Mature biofilms were treated with PBS plus STAMP as described for the single-species biofilm assay, with the same controls. After treatment, biofilms were washed 2× in PBS and then physically disrupted with a sterile pipette tip in 100 µL PBS per well. Cell suspensions were then serially diluted 10-fold to 10$^{-6}$. Diluted suspensions were then plated on TH medium and TH supplemented with spectinomycin, 800 µg/mL. The total amount of biofilm killing (all streptococci) was determined by counting colonies from TH-only plates. Controls: 100% of untreated corresponds to the number of cfu/mL recorded from untreated biofilms, 0% survival was obtained from ethanol sterilized samples. *S. mutans* killing was determined from quantitating colonies on TH-spectinomycin plates, and combined total cfu/mL, was utilized to calculate the ratio of *S. mutans*:total population. 1:1 ratio indicates no selectivity.

As shown in FIG. 14, C16-BD2.21 has no impact on the total cfu/mL population, suggesting that non-*S. mutans* streptococci are not affected by the STAMP to a significant degree (See FIG. 14(A)). This is confirmed by the observed ratio of surviving *S. mutans* to total streptococci, which is 0.075 (See FIG. 14 (B)). 1903-BD2.21 also had a selective ratio (well under 1, see FIG. 14 (B)), though had some impact on other oral streptococci (See FIG. 14 (A)).

TABLE 7

Antimicrobial Peptides

Andropin (SEQ ID NO 54)
VFIDILDKMENAIHKAAQAGIGIAKPIEKMILPK

Apidaecin (SEQ ID NO 55)
GNRPVYIPPPRPPHPRL

Bacteriocin leucocin A (SEQ ID NO 56)
KYYGNGVHCTKSGCSVNWGEAFSAGVHRLANGGNGFW bactenecin (SEQ ID NO 57)
RLCRIVVIRVCR Buforin II (SEQ ID NO 58)
TRSSRAGLQFPVGRVHRLLRK Cathelicidin (human LL-37) (SEQ ID NO 59)
LLGDFFRKSKEKIGKEFKRIVQRIKDFLRNLVPRTES Clavanin A (SEQ ID NO 60)
VFQFLGKIIHHVGNFVHGFSHVF Cecropin (SEQ ID NO 61)
RWKIFKKIEKVGQNIRDGIVKAGPAVAVVGQAATI Cyclic Dodecapeptide (SEQ ID NO 62)
RICRIIFLRVCR β-defensin I (human) (SEQ ID NO 63)
DFASCHTNGGICLPNRCPGHMIQIGICFRPRVKCCRSW α-defensin (HNP-1) (SEQ ID NO 64)
ACYCRIPACIAGERRYGTCIYQGRLWAFCC Gaegurin (SEQ ID NO 65)
SLFSLIKAGAKFLGKNLLKQGACYAACKASKQC Histatin (SEQ ID NO 66)
DSHEERHHGRHGHHKYGRKFHEKHHSHRGYRSNYLYDN Indolicidin (SEQ ID NO 67)
ILPWKWPWWPWRR Magainin II (SEQ ID NO 68)
GIGKFLHSAKKFGKAFVGEIMNS Melittin B (SEQ ID NO 69)
GIGAVLKVLTTGLPALISWIKRKRQQ Nisin A (SEQ ID NO 70)
ITSISLCTPGCKTGALMGCNMKTATCHCSIHVSK novispirin G10 (SEQ ID NO 35)
KNLRRIIRKGIHIIKKYG Protegrin (SEQ ID NO 34)
RGGRLCYCRRRFCVCVGR Ranalexin (SEQ ID NO 71)
LGGLIKIVPAMICAVTKKC Tachyplesin (SEQ ID NO 72)
KWCFRVCYRGICYRRCR Maximin H5 (amphibians) (SEQ ID NO 73)
ILGPVLGLVSDTLDDVLGIL TABLE 7-continued Antimicrobial Peptides Surfactant Extract 1 (SEQ ID NO 74)
DDDDDD

DCD-1 (SEQ ID NO 75)
SSLLEKGLDGAKKAVGGLGKLGKDAVEDLESVGKGAVHDVKDVLDSV

SSL-25 (SEQ ID NO 76)
SSLLEKGLDGAKKAVGGLGKLGKDA

SSL-23 (SEQ ID NO 77)
SSLLEKGLDGAKKAVGGLGKLGK

Dermaseptin DS5 (SEQ ID NO 78)
GLWSKIKTAGKSVAKAAAKAAVKAVTNAV

Moricin (insect) (SEQ ID NO 79)
AKIPIKAIKTVGKAVGKGLRAINIASTANDVFNFLKPIKKRKA

Bombinin (frog) (SEQ ID NO 80)
GIGALSAKGALKGLAKGLAEHFAN

Pleurocidin (white flounder) (SEQ ID NO 81)
GWGSFFKKAAHVGKHVGKAALHTYL

SMAP29 (sheep) (SEQ ID NO 82)
RGLRRLGRKIAHGVKKYGPTVLRIIRIAG

PMAP-23 (pig) (SEQ ID NO 83)
RIIDLLWRVRRPQKPKFVTVWVR

VCP-5h (wasp) (SEQ ID NO 84)
FLPIIGKLLSGLL-NH$_2$

Abaecin (honeybee) (SEQ ID NO 85)
YVPLPNVPQPGRRPFPTFPGQGPFNPKIKWPQGY

Drosocin (fruitfly) (SEQ ID NO 86)
GKPRPYSPRPTSHPRPIRV

Pyrrhocoricin (sap-sucker bug) (SEQ ID NO 87)
VDKGSYLPRPTPPRPIYNRN $L_{15}K_7$ (SEQ ID NO 88)
KLLKLLLKLLKLLLKLLLKLLK KLApep (SEQ ID NO 89)
KLALKLALKAWKAALKLA-NH$_2$ $D_2A_{21}$ (SEQ ID NO 90)
FAKKFAKKFKKFAKKFAKFAFAF Modelin-1 (SEQ ID NO 91)
KLWKKWAKKWLKLWKAW LARL (SEQ ID NO 92)
Ac-LARLLARLLARL-Ac

YLK-P (SEQ ID NO 93)
YKLLKLLLPKLKGLLFKL-NH$_2$

KSL2 (SEQ ID NO 94)
KKVVFKFKFK-NH$_2$

CAM135 (SEQ ID NO 95)
GWRLIKKILRVFKGL-NH$_2$

PGAa (SEQ ID NO 96)
GILSKLGKALKKAAKHAAKA-NH$_2$

PGYa (SEQ ID NO 97)
GLLRRLRDFLKKIGEKFKKIGY-NH$_2$

References in the disclosures are listed below and are incorporated in their entirety.

Ajdic, D., W. M. McShan, R. E. McLaughlin, G. Savic, J. Chang, M. B. Carson, C. Primeaux, R. Tian, S. Kenton, H. Jia, S. Lin, Y. Qian, S. Li, H. Zhu, F. Najar, H. Lai, J.

White, B. A. Roe, and J. J. Ferretti. 2002. Genome sequence of *Streptococcus mutans* UA159, a cariogenic dental pathogen. Proc. Natl. Acad. Sci. USA 99:14434-9.

Anderson, M. H., and W. Shi. 2006. A probiotic approach to caries management. Pediatic Dentistry In Press.

Axelsson, P., and J. Lindhe. 1987. Efficacy of mouthrinses in inhibiting dental plaque and gingivitis in man. J. Clin. Periodontol. 14:205-12.

Blehert, D. S., R. J. Palmer, Jr., J. B. Xavier, J. S. Almeida, and P. E. Kolenbrander. 2003. Autoinducer 2 production by *Streptococcus gordonii* DL1 and the biofilm phenotype of a luxS mutant are influenced by nutritional conditions. J. Bacteriol. 185:4851-60.

Bonacorsi, S., F. Fitoussi, S. Lhopital, and E. Bingen. 1999. Comparative in vitro activities of meropenem, imipenem, temocillin, piperacillin, and ceftazidime in combination with tobramycin, rifampin, or ciprofloxacin against *Burkholderia cepacia* isolates from patients with cystic fibrosis. Antimicrob. Agents Chemother. 43:213-217.

Caufield, P. W., A. P. Dasanayake, Y. Li, Y. Pan, J. Hsu, and J. M. Hardin. 2000. Natural history of *Streptococcus sanguinis* in the oral cavity of infants: evidence for a discrete window of infectivity. Infect. Immun. 68:4018-23.

Donlan, R. M., and J. W. Costerton. 2002. Biofilms: survival mechanisms of clinically relevant microorganisms. Clin. Microbiol. Rev. 15:167-93.

Eckert, R., F. Qi, D. K. Yarbrough, J. He, M. H. Anderson, W. Shi. 2006. Adding selectivity to antimicrobial peptides: rational design of a multidomain peptide against *Pseudomonas* spp. Antimicrob. Agents. Chemother. 50:1480-1488.

Fuchs, H. J., D. S. Borowitz, D. H. Christiansen, E. M. Morris, M. L. Nash, B. W. Ramsey, B. J. Rosenstein, A. L. Smith, and M. E. Wohl. 1994. Effect of aerosolized recombinant human DNase on exacerbations of respiratory symptoms and on pulmonary function in patients with cystic fibrosis. The Pulmozyme Study Group. N Engl J Med 331:637-42.

Gilmour, M. N., T. S. Whittam, M. Kilian, and R. K. Selander. 1987. Genetic relationships among the oral streptococci. J. Bacteriol. 169:5247-57.

Li, Y. H., P. C. Lau, J. H. Lee, R. P. Ellen, and D. G. Cvitkovitch. 2001. Natural genetic transformation of *Streptococcus mutans* growing in biofilms. J. Bacteriol. 183:897-908.

Merritt, J., J. Kreth, F. Qi, R. Sullivan, and W. Shi. 2005. Non-disruptive, real-time analyses of the metabolic status and viability of *Streptococcus mutans* cells in response to antimicrobial treatments. J. Microbiol. Methods 61:161-70.

Milton, R. C., S. C. Milton, and S. B. Kent. 1992. Total chemical synthesis of a D-enzyme: the enantiomers of HIV-1 protease show reciprocal chiral substrate specificity [corrected]. Science 256:1445-8.

Perron, G. G., M. Zasloff, and G. Bell. 2006. Experimental evolution of resistance to an antimicrobial peptide. Proc. Biol. Sci. 273:251-6.

Qi, F., J. Kreth, C. M. Levesque, O. Kay, R. W. Mair, W. Shi, D. G. Cvitkovitch, and S. D. Goodman. 2005. Peptide pheromone induced cell death of *Streptococcus mutans*. FEMS Microbiol. Lett. 251:321-6.

Qiu, X. Q., J. Zhang, H. Wang, G. Y. Wu. 2005. A novel engineered peptide, a narrow-spectrum antibiotic, is effective against vancomycin-resistant *Enterococcus faecalis*. Antimicrob. Agents Chemother. 49:1184-1189.

Rogers, A. H. 1975. Bacteriocin types of *Streptococcus mutans* in human mouths. Arch. Oral Biol. 20:853-858.

Saiman, L., S. Tabibi, T. D. Starner, P. San Gabriel, P. L. Winokur, H. P. Jia, P. B. McCray, Jr., and B. F. Tack. 2001. Cathelicidin peptides inhibit multiply antibiotic-resistant pathogens from patients with cystic fibrosis. Antimicrob. Agents Chemother. 45:2838-44.

Sajjan, U. S., L. T. Tran, N. Sole, C. Rovaldi, A. Akiyama, P. M. Friden, J. F. Forstner, and D. M. Rothstein. 2001. P-113D, an antimicrobial peptide active against *Pseudomonas aeruginosa*, retains activity in the presence of sputum from cystic fibrosis patients. Antimicrob Agents Chemother 45:3437-44.

---

What is claimed is:

1. A method of reducing the ratio of living *Streptococcus mutans* to total streptococci in a biofilm, said method comprising contacting said *Streptococcus mutans* with an amount of a construct effective to kill an *Streptococcus mutans*, wherein said construct comprises a targeting peptide that binds *Streptococcus mutans* attached to an antimicrobial peptide, wherein the amino acid sequence of said targeting peptide consists of a fragment of the competence stimulating peptide (CSP) ranging in length from 8 to 20 amino acids.

2. The method of claim 1, wherein said fragment comprises the amino acid sequence TFFRLFNR (SEQ ID NO:5).

3. The method of claim 1, wherein said fragment comprises the amino acid sequence TFFRLFNRSFTQALGK (SEQ ID NO:2).

4. The method of claim 1, wherein said fragment consists of the amino acid sequence TFFRLFNRSFTQALGK (SEQ ID NO:2).

5. The method according to any one of claims 1-4, wherein the amino acid sequence of said antimicrobial peptide comprises a novispirin amino acid sequence or a fragment thereof having antimicrobial activity.

6. The method of claim 5, wherein the amino acid sequence of said antimicrobial peptide comprises the sequence KNLRIIRKGIHIIKKY (SEQ ID NO:3).

7. The method of claim 5, wherein the amino acid sequence of said antimicrobial peptide consists of the sequence KNLRIIRKGIHIIKKY (SEQ ID NO:3).

8. The method of claim 5, wherein the targeting peptide is attached to the antimicrobial peptide by a linker peptide.

9. The method of claim 8, wherein the targeting peptide is attached to the antimicrobial peptide by a linker peptide, where the amino acid sequence of said linker peptide is selected from the group consisting of GGG (SEQ ID NO:17), AAA (SEQ ID NO:18), SAT (SEQ ID NO:19), ASA (SEQ ID NO:20), SGG (SEQ ID NO: 21), PYP (SEQ ID NO:22), SGS (SEQ ID NO:23), GGS (SEQ ID NO:24), SPS(SEQ ID NO:25), PSGSP (SEQ ID NO:26), PSPSP (SEQ ID NO:27), and GGSGGS (SEQ ID NO:28).

10. The method of claim 5, wherein the amino acid sequence of said construct comprises the sequence TFFRLFNRSFTQALGKGGGKNLRIIRKGIHIIKKY (SEQ ID NO:4).

11. The method of claim 5, wherein the amino acid sequence of said construct consists of the sequence TFFRLFNRSFTQALGKGGGKNLRIIRKGIHIIKKY (SEQ ID NO:4).

12. The method of claim 11, wherein the carboxyl terminus of said antimicrobial peptide is amidated.

13. The method of claim 11, wherein said biofilm is on an oral soft tissue or on teeth.

14. The method of claim 5, wherein the carboxyl terminus of said antimicrobial peptide is amidated.

15. The method of claim 14, wherein said biofilm is on an oral soft tissue or on teeth.

* * * * *

SEQUENCE LISTING

```
<160> NUMBER OF SEQ ID NOS: 97

<210> SEQ ID NO 1
<211> LENGTH: 21
<212> TYPE: PRT
<213> ORGANISM: Artificial Sequence
<220> FEATURE:
<223> OTHER INFORMATION: synthetic bacterial pheromone competence
      stimulating peptide (CSP) targeting peptide

<400> SEQUENCE: 1

Ser Gly Ser Leu Ser Thr Phe Phe Arg Leu Phe Asn Arg Ser Phe Thr
1               5                   10                  15

Gln Ala Leu Gly Lys
            20

<210> SEQ ID NO 2
<211> LENGTH: 16
<212> TYPE: PRT
<213> ORGANISM: Artificial Sequence
<220> FEATURE:
<223> OTHER INFORMATION: synthetic C-terminal 16 amino acids of
      bacterial pheromone competence stimulating peptide (CSP),
      targeting peptide C16 (CSP-16)
```

```
<400> SEQUENCE: 2

Thr Phe Phe Arg Leu Phe Asn Arg Ser Phe Thr Gln Ala Leu Gly Lys
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: synthetic antimicrobial peptide G2, derivative
      of novispirin G10
<220> FEATURE:
<221> NAME/KEY: MOD_RES
<222> LOCATION: (16)...(16)
<223> OTHER INFORMATION: tyrosinamide

<400> SEQUENCE: 3

Lys Asn Leu Arg Ile Ile Arg Lys Gly Ile His Ile Ile Lys Lys Tyr
1               5                   10                  15

<210> SEQ ID NO 4
<211> LENGTH: 35
<212> TYPE: PRT
<213> ORGANISM: Artificial Sequence
<220> FEATURE:
<223> OTHER INFORMATION: synthetic selectively/specifically targeted
      antimicrobial peptide (STAMP) chimeric polypeptide C16G2
<220> FEATURE:
<221> NAME/KEY: MOD_RES
<222> LOCATION: (35)...(35)
<223> OTHER INFORMATION: tyrosinamide

<400> SEQUENCE: 4

Thr Phe Phe Arg Leu Phe Asn Arg Ser Phe Thr Gln Ala Leu Gly Lys
1               5                   10                  15

Gly Gly Gly Lys Asn Leu Arg Ile Ile Arg Lys Gly Ile His Ile Ile
            20                  25                  30

Lys Lys Tyr
        35

<210> SEQ ID NO 5
<211> LENGTH: 8
<212> TYPE: PRT
<213> ORGANISM: Artificial Sequence
<220> FEATURE:
<223> OTHER INFORMATION: synthetic targeting peptide M8 (CSP-M8),
      competence stimulating peptide (CSP) fragment peptide C16-12
      with C-terminal deletion

<400> SEQUENCE: 5

Thr Phe Phe Arg Leu Phe Asn Arg
1               5

<210> SEQ ID NO 6
<211> LENGTH: 27
<212> TYPE: PRT
<213> ORGANISM: Artificial Sequence
<220> FEATURE:
<223> OTHER INFORMATION: synthetic selectively/specifically targeted
      antimicrobial peptide (STAMP) chimeric polypeptide M8G2
<220> FEATURE:
<221> NAME/KEY: MOD_RES
<222> LOCATION: (27)...(27)
<223> OTHER INFORMATION: tyrosinamide

<400> SEQUENCE: 6

Thr Phe Phe Arg Leu Phe Asn Arg Gly Gly Gly Lys Asn Leu Arg Ile
1               5                   10                  15
```

Ile Arg Lys Gly Ile His Ile Ile Lys Lys Tyr
            20                  25

<210> SEQ ID NO 7
<211> LENGTH: 11
<212> TYPE: PRT
<213> ORGANISM: Artificial Sequence
<220> FEATURE:
<223> OTHER INFORMATION: synthetic antimicrobial peptide S6L3-33

<400> SEQUENCE: 7

Phe Lys Lys Phe Trp Lys Trp Phe Arg Arg Phe
1               5                   10

<210> SEQ ID NO 8
<211> LENGTH: 31
<212> TYPE: PRT
<213> ORGANISM: Artificial Sequence
<220> FEATURE:
<223> OTHER INFORMATION: synthetic selectively/specifically targeted
      antimicrobial peptide (STAMP) chimeric polypeptide C16-33

<400> SEQUENCE: 8

Thr Arg Arg Arg Leu Phe Asn Arg Ser Phe Thr Gln Ala Leu Gly Lys
1               5                   10                  15

Ser Gly Gly Gly Phe Lys Lys Phe Trp Lys Trp Phe Arg Arg Phe
            20                  25                  30

<210> SEQ ID NO 9
<211> LENGTH: 23
<212> TYPE: PRT
<213> ORGANISM: Artificial Sequence
<220> FEATURE:
<223> OTHER INFORMATION: synthetic selectively/specifically targeted
      antimicrobial peptide (STAMP) chimeric polypeptide M8-33

<400> SEQUENCE: 9

Thr Phe Phe Arg Leu Phe Asn Arg Ser Gly Gly Gly Phe Lys Lys Phe
1               5                   10                  15

Trp Lys Trp Phe Arg Arg Phe
            20

<210> SEQ ID NO 10
<211> LENGTH: 8
<212> TYPE: PRT
<213> ORGANISM: Artificial Sequence
<220> FEATURE:
<223> OTHER INFORMATION: synthetic targeting peptide 1903

<400> SEQUENCE: 10

Asn Ile Phe Glu Tyr Phe Leu Glu
1               5

<210> SEQ ID NO 11
<211> LENGTH: 11
<212> TYPE: PRT
<213> ORGANISM: Artificial Sequence
<220> FEATURE:
<223> OTHER INFORMATION: synthetic antimicrobial peptide BD2.21

<400> SEQUENCE: 11

Lys Leu Phe Lys Phe Leu Arg Lys His Leu Leu
1               5                   10

<210> SEQ ID NO 12

```
<211> LENGTH: 27
<212> TYPE: PRT
<213> ORGANISM: Artificial Sequence
<220> FEATURE:
<223> OTHER INFORMATION: synthetic selectively/specifically targeted
      antimicrobial peptide (STAMP) chimeric polypeptide 1903-G2

<400> SEQUENCE: 12

Asn Ile Phe Glu Tyr Phe Leu Glu Gly Gly Gly Lys Asn Leu Arg Ile
1               5                   10                  15

Ile Arg Lys Gly Ile His Ile Ile Lys Lys Tyr
            20                  25

<210> SEQ ID NO 13
<211> LENGTH: 22
<212> TYPE: PRT
<213> ORGANISM: Artificial Sequence
<220> FEATURE:
<223> OTHER INFORMATION: synthetic selectively/specifically targeted
      antimicrobial peptide (STAMP) chimeric polypeptide 1903-BD2.21

<400> SEQUENCE: 13

Asn Ile Phe Glu Tyr Phe Leu Glu Gly Gly Gly Lys Leu Phe Lys Phe
1               5                   10                  15

Leu Arg Lys His Leu Leu
            20

<210> SEQ ID NO 14
<211> LENGTH: 30
<212> TYPE: PRT
<213> ORGANISM: Artificial Sequence
<220> FEATURE:
<223> OTHER INFORMATION: synthetic selectively/specifically targeted
      antimicrobial peptide (STAMP) chimeric polypeptide C16-BD2.21

<400> SEQUENCE: 14

Thr Phe Phe Arg Leu Phe Asn Arg Ser Phe Thr Gln Ala Leu Gly Lys
1               5                   10                  15

Gly Gly Gly Lys Leu Phe Lys Phe Leu Arg Lys His Leu Leu
            20                  25                  30

<210> SEQ ID NO 15
<211> LENGTH: 22
<212> TYPE: PRT
<213> ORGANISM: Artificial Sequence
<220> FEATURE:
<223> OTHER INFORMATION: synthetic selectively/specifically targeted
      antimicrobial peptide (STAMP) chimeric polypeptide M8-BD2.21

<400> SEQUENCE: 15

Thr Phe Phe Arg Leu Phe Asn Arg Gly Gly Gly Lys Leu Phe Lys Phe
1               5                   10                  15

Leu Arg Lys His Leu Leu
            20

<210> SEQ ID NO 16
<211> LENGTH: 22
<212> TYPE: PRT
<213> ORGANISM: Artificial Sequence
<220> FEATURE:
<223> OTHER INFORMATION: synthetic selectively/specifically targeted
      antimicrobial peptide (STAMP) chimeric polypeptide 1903-33

<400> SEQUENCE: 16

Asn Ile Phe Glu Tyr Phe Leu Glu Gly Gly Gly Phe Lys Lys Phe Trp
1               5                   10                  15
```

Lys Trp Phe Arg Arg Phe
            20

<210> SEQ ID NO 17
<211> LENGTH: 3
<212> TYPE: PRT
<213> ORGANISM: Artificial Sequence
<220> FEATURE:
<223> OTHER INFORMATION: synthetic linker peptide

<400> SEQUENCE: 17

Gly Gly Gly
 1

<210> SEQ ID NO 18
<211> LENGTH: 3
<212> TYPE: PRT
<213> ORGANISM: Artificial Sequence
<220> FEATURE:
<223> OTHER INFORMATION: synthetic linker peptide

<400> SEQUENCE: 18

Ala Ala Ala
 1

<210> SEQ ID NO 19
<211> LENGTH: 3
<212> TYPE: PRT
<213> ORGANISM: Artificial Sequence
<220> FEATURE:
<223> OTHER INFORMATION: synthetic linker peptide

<400> SEQUENCE: 19

Ser Ala Thr
 1

<210> SEQ ID NO 20
<211> LENGTH: 3
<212> TYPE: PRT
<213> ORGANISM: Artificial Sequence
<220> FEATURE:
<223> OTHER INFORMATION: synthetic linker peptide

<400> SEQUENCE: 20

Ala Ser Ala
 1

<210> SEQ ID NO 21
<211> LENGTH: 3
<212> TYPE: PRT
<213> ORGANISM: Artificial Sequence
<220> FEATURE:
<223> OTHER INFORMATION: synthetic linker peptide

<400> SEQUENCE: 21

Ser Gly Gly
 1

<210> SEQ ID NO 22
<211> LENGTH: 3
<212> TYPE: PRT
<213> ORGANISM: Artificial Sequence
<220> FEATURE:
<223> OTHER INFORMATION: synthetic linker peptide

<400> SEQUENCE: 22

```
Pro Tyr Pro
 1

<210> SEQ ID NO 23
<211> LENGTH: 3
<212> TYPE: PRT
<213> ORGANISM: Artificial Sequence
<220> FEATURE:
<223> OTHER INFORMATION: synthetic linker peptide

<400> SEQUENCE: 23

Ser Gly Ser
 1

<210> SEQ ID NO 24
<211> LENGTH: 3
<212> TYPE: PRT
<213> ORGANISM: Artificial Sequence
<220> FEATURE:
<223> OTHER INFORMATION: synthetic linker peptide

<400> SEQUENCE: 24

Gly Gly Ser
 1

<210> SEQ ID NO 25
<211> LENGTH: 3
<212> TYPE: PRT
<213> ORGANISM: Artificial Sequence
<220> FEATURE:
<223> OTHER INFORMATION: synthetic linker peptide

<400> SEQUENCE: 25

Ser Pro Ser
 1

<210> SEQ ID NO 26
<211> LENGTH: 5
<212> TYPE: PRT
<213> ORGANISM: Artificial Sequence
<220> FEATURE:
<223> OTHER INFORMATION: synthetic linker peptide

<400> SEQUENCE: 26

Pro Ser Gly Ser Pro
 1               5

<210> SEQ ID NO 27
<211> LENGTH: 5
<212> TYPE: PRT
<213> ORGANISM: Artificial Sequence
<220> FEATURE:
<223> OTHER INFORMATION: synthetic linker peptide

<400> SEQUENCE: 27

Pro Ser Pro Ser Pro
 1               5

<210> SEQ ID NO 28
<211> LENGTH: 6
<212> TYPE: PRT
<213> ORGANISM: Artificial Sequence
<220> FEATURE:
<223> OTHER INFORMATION: synthetic linker peptide dimer

<400> SEQUENCE: 28

Gly Gly Ser Gly Gly Ser
```

```
1               5

<210> SEQ ID NO 29
<211> LENGTH: 17
<212> TYPE: PRT
<213> ORGANISM: Artificial Sequence
<220> FEATURE:
<223> OTHER INFORMATION: synthetic bacterial pheromone competence
      stimulating peptide (CSP) targeting peptide CSP1

<400> SEQUENCE: 29

Glu Met Arg Leu Ser Lys Phe Phe Arg Asp Phe Ile Leu Gln Arg Lys
1               5                   10                  15

Lys

<210> SEQ ID NO 30
<211> LENGTH: 17
<212> TYPE: PRT
<213> ORGANISM: Artificial Sequence
<220> FEATURE:
<223> OTHER INFORMATION: synthetic bacterial pheromone competence
      stimulating peptide (CSP) targeting peptide CSP2

<400> SEQUENCE: 30

Glu Met Arg Ile Ser Arg Ile Ile Leu Asp Phe Leu Phe Leu Arg Lys
1               5                   10                  15

Lys

<210> SEQ ID NO 31
<211> LENGTH: 12
<212> TYPE: PRT
<213> ORGANISM: Artificial Sequence
<220> FEATURE:
<223> OTHER INFORMATION: synthetic targeting peptide Cat-1 domain, KH
      domain

<400> SEQUENCE: 31

Lys Lys His Arg Lys His Arg Lys His Arg Lys His
1               5                   10

<210> SEQ ID NO 32
<211> LENGTH: 24
<212> TYPE: PRT
<213> ORGANISM: Artificial Sequence
<220> FEATURE:
<223> OTHER INFORMATION: synthetic antimicrobial peptide histatin 5

<400> SEQUENCE: 32

Asp Ser His Ala Lys Arg His His Gly Tyr Lys Arg Lys Phe His Glu
1               5                   10                  15

Lys His His Ser His Arg Gly Tyr
            20

<210> SEQ ID NO 33
<211> LENGTH: 14
<212> TYPE: PRT
<213> ORGANISM: Artificial Sequence
<220> FEATURE:
<223> OTHER INFORMATION: synthetic antimicrobial peptide dhvar-1

<400> SEQUENCE: 33

Lys Arg Leu Phe Lys Glu Leu Lys Phe Ser Leu Arg Lys Tyr
1               5                   10

<210> SEQ ID NO 34
```

```
<211> LENGTH: 18
<212> TYPE: PRT
<213> ORGANISM: Artificial Sequence
<220> FEATURE:
<223> OTHER INFORMATION: synthetic antimicrobial peptide protegrin PG-1

<400> SEQUENCE: 34

Arg Gly Gly Arg Leu Cys Tyr Cys Arg Arg Arg Phe Cys Val Cys Val
1               5                   10                  15

Gly Arg

<210> SEQ ID NO 35
<211> LENGTH: 18
<212> TYPE: PRT
<213> ORGANISM: Artificial Sequence
<220> FEATURE:
<223> OTHER INFORMATION: synthetic antimicrobial peptide novispirin G10

<400> SEQUENCE: 35

Lys Asn Leu Arg Arg Ile Ile Arg Lys Gly Ile His Ile Ile Lys Lys
1               5                   10                  15

Tyr Gly

<210> SEQ ID NO 36
<211> LENGTH: 36
<212> TYPE: PRT
<213> ORGANISM: Artificial Sequence
<220> FEATURE:
<223> OTHER INFORMATION: synthetic selectively/specifically targeted
      antimicrobial peptide (STAMP) chimeric polypeptide G10KHc,
      targeting peptide-linker peptide-antimicrobial peptide G10KHc

<400> SEQUENCE: 36

Lys Lys His Arg Lys His Arg Lys His Arg Lys His Gly Gly Ser Gly
1               5                   10                  15

Gly Ser Lys Asn Leu Arg Arg Ile Ile Arg Lys Gly Ile His Ile Ile
                20                  25                  30

Lys Lys Tyr Gly
        35

<210> SEQ ID NO 37
<211> LENGTH: 13
<212> TYPE: PRT
<213> ORGANISM: Artificial Sequence
<220> FEATURE:
<223> OTHER INFORMATION: synthetic competence stimulating peptide (CSP)
      fragment peptide C16-1 with N-terminal deletion

<400> SEQUENCE: 37

Arg Leu Phe Asn Arg Ser Phe Thr Gln Ala Leu Gly Lys
1               5                   10

<210> SEQ ID NO 38
<211> LENGTH: 13
<212> TYPE: PRT
<213> ORGANISM: Artificial Sequence
<220> FEATURE:
<223> OTHER INFORMATION: synthetic competence stimulating peptide (CSP)
      fragment peptide C16-2 with internal deletion

<400> SEQUENCE: 38

Thr Phe Phe Asn Arg Ser Phe Thr Gln Ala Leu Gly Lys
1               5                   10

<210> SEQ ID NO 39
```

-continued

```
<211> LENGTH: 12
<212> TYPE: PRT
<213> ORGANISM: Artificial Sequence
<220> FEATURE:
<223> OTHER INFORMATION: synthetic competence stimulating peptide (CSP)
      fragment peptide C16-3 with internal deletion

<400> SEQUENCE: 39

Thr Phe Phe Arg Leu Phe Thr Gln Ala Leu Gly Lys
1               5                   10

<210> SEQ ID NO 40
<211> LENGTH: 13
<212> TYPE: PRT
<213> ORGANISM: Artificial Sequence
<220> FEATURE:
<223> OTHER INFORMATION: synthetic competence stimulating peptide (CSP)
      fragment peptide C16-4 with internal deletion

<400> SEQUENCE: 40

Thr Phe Phe Arg Leu Phe Asn Arg Ser Ala Leu Gly Lys
1               5                   10

<210> SEQ ID NO 41
<211> LENGTH: 13
<212> TYPE: PRT
<213> ORGANISM: Artificial Sequence
<220> FEATURE:
<223> OTHER INFORMATION: synthetic competence stimulating peptide (CSP)
      fragment peptide C16-5 with internal deletion

<400> SEQUENCE: 41

Thr Phe Phe Arg Leu Phe Asn Arg Ser Phe Thr Gln Lys
1               5                   10

<210> SEQ ID NO 42
<211> LENGTH: 9
<212> TYPE: PRT
<213> ORGANISM: Artificial Sequence
<220> FEATURE:
<223> OTHER INFORMATION: synthetic competence stimulating peptide (CSP)
      fragment peptide C16-6 with C-terminal deletion

<400> SEQUENCE: 42

Thr Phe Phe Arg Leu Phe Asn Arg Ser
1               5

<210> SEQ ID NO 43
<211> LENGTH: 10
<212> TYPE: PRT
<213> ORGANISM: Artificial Sequence
<220> FEATURE:
<223> OTHER INFORMATION: synthetic competence stimulating peptide (CSP)
      fragment peptide C16-7 with N-terminal and C-terminal deletions

<400> SEQUENCE: 43

Arg Leu Phe Asn Arg Ser Phe Thr Gln Ala
1               5                   10

<210> SEQ ID NO 44
<211> LENGTH: 9
<212> TYPE: PRT
<213> ORGANISM: Artificial Sequence
<220> FEATURE:
<223> OTHER INFORMATION: synthetic competence stimulating peptide (CSP)
      fragment peptide C16-8 with N-terminal deletion

<400> SEQUENCE: 44
```

-continued

```
Arg Ser Phe Thr Gln Ala Leu Gly Lys
 1               5

<210> SEQ ID NO 45
<211> LENGTH: 3
<212> TYPE: PRT
<213> ORGANISM: Artificial Sequence
<220> FEATURE:
<223> OTHER INFORMATION: synthetic competence stimulating peptide (CSP)
      fragment peptide C16-9 with C-terminal deletion

<400> SEQUENCE: 45

Thr Phe Phe
 1

<210> SEQ ID NO 46
<211> LENGTH: 4
<212> TYPE: PRT
<213> ORGANISM: Artificial Sequence
<220> FEATURE:
<223> OTHER INFORMATION: synthetic competence stimulating peptide (CSP)
      fragment peptide C16-10 with C-terminal deletion

<400> SEQUENCE: 46

Thr Phe Phe Arg
 1

<210> SEQ ID NO 47
<211> LENGTH: 5
<212> TYPE: PRT
<213> ORGANISM: Artificial Sequence
<220> FEATURE:
<223> OTHER INFORMATION: synthetic competence stimulating peptide (CSP)
      fragment peptide C16-11 with C-terminal deletion

<400> SEQUENCE: 47

Thr Phe Phe Arg Leu
 1               5

<210> SEQ ID NO 48
<211> LENGTH: 16
<212> TYPE: PRT
<213> ORGANISM: Artificial Sequence
<220> FEATURE:
<223> OTHER INFORMATION: synthetic competence stimulating peptide (CSP)
      fragment peptide C16-13 with Phe to Gly substitutions

<400> SEQUENCE: 48

Thr Gly Gly Arg Leu Gly Asn Arg Ser Gly Thr Gln Ala Leu Gly Lys
 1               5                  10                  15

<210> SEQ ID NO 49
<211> LENGTH: 16
<212> TYPE: PRT
<213> ORGANISM: Artificial Sequence
<220> FEATURE:
<223> OTHER INFORMATION: synthetic competence stimulating peptide (CSP)
      fragment peptide C16-14 with Arg to Asn substitutions

<400> SEQUENCE: 49

Thr Phe Phe Asn Leu Phe Asn Asn Ser Phe Thr Gln Ala Leu Gly Lys
 1               5                  10                  15

<210> SEQ ID NO 50
<211> LENGTH: 16
<212> TYPE: PRT
<213> ORGANISM: Artificial Sequence
<220> FEATURE:
```

<223> OTHER INFORMATION: synthetic competence stimulating peptide (CSP)
      fragment peptide C16-15 with 4-residue Ala scan

<400> SEQUENCE: 50

Ala Ala Ala Ala Leu Phe Asn Arg Ser Phe Thr Gln Ala Leu Gly Lys
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: synthetic competence stimulating peptide (CSP)
      fragment peptide C16-16 with 4-residue Ala scan

<400> SEQUENCE: 51

Thr Phe Phe Arg Ala Ala Ala Ala Ser Phe Thr Gln Ala Leu Gly Lys
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: synthetic competence stimulating peptide (CSP)
      fragment peptide C16-17 with 4-residue Ala scan

<400> SEQUENCE: 52

Thr Phe Phe Arg Leu Phe Asn Arg Ala Ala Ala Ala Leu Gly Lys
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: synthetic competence stimulating peptide (CSP)
      fragment peptide C16-18 with 4-residue Ala scan

<400> SEQUENCE: 53

Thr Phe Phe Arg Leu Phe Asn Arg Ser Phe Thr Gln Ala Ala Ala Ala
1               5                   10                  15

<210> SEQ ID NO 54
<211> LENGTH: 34
<212> TYPE: PRT
<213> ORGANISM: Artificial Sequence
<220> FEATURE:
<223> OTHER INFORMATION: synthetic antimicrobial peptide andropin

<400> SEQUENCE: 54

Val Phe Ile Asp Ile Leu Asp Lys Met Glu Asn Ala Ile His Lys Ala
1               5                   10                  15

Ala Gln Ala Gly Ile Gly Ile Ala Lys Pro Ile Glu Lys Met Ile Leu
            20                  25                  30

Pro Lys

<210> SEQ ID NO 55
<211> LENGTH: 17
<212> TYPE: PRT
<213> ORGANISM: Artificial Sequence
<220> FEATURE:
<223> OTHER INFORMATION: synthetic antimicrobial peptide apidaecin

<400> SEQUENCE: 55

Gly Asn Arg Pro Val Tyr Ile Pro Pro Pro Arg Pro Pro His Pro Arg

```
1               5                   10                  15
Leu

<210> SEQ ID NO 56
<211> LENGTH: 37
<212> TYPE: PRT
<213> ORGANISM: Artificial Sequence
<220> FEATURE:
<223> OTHER INFORMATION: synthetic antimicrobial peptide bacteriocin
      leucocin A

<400> SEQUENCE: 56

Lys Tyr Tyr Gly Asn Gly Val His Cys Thr Lys Ser Gly Cys Ser Val
1               5                   10                  15

Asn Trp Gly Glu Ala Phe Ser Ala Gly Val His Arg Leu Ala Asn Gly
            20                  25                  30

Gly Asn Gly Phe Trp
        35

<210> SEQ ID NO 57
<211> LENGTH: 12
<212> TYPE: PRT
<213> ORGANISM: Artificial Sequence
<220> FEATURE:
<223> OTHER INFORMATION: synthetic antimicrobial peptide bactenecin

<400> SEQUENCE: 57

Arg Leu Cys Arg Ile Val Val Ile Arg Val Cys Arg
1               5                   10

<210> SEQ ID NO 58
<211> LENGTH: 21
<212> TYPE: PRT
<213> ORGANISM: Artificial Sequence
<220> FEATURE:
<223> OTHER INFORMATION: synthetic antimicrobial peptide buforin II

<400> SEQUENCE: 58

Thr Arg Ser Ser Arg Ala Gly Leu Gln Phe Pro Val Gly Arg Val His
1               5                   10                  15

Arg Leu Leu Arg Lys
            20

<210> SEQ ID NO 59
<211> LENGTH: 37
<212> TYPE: PRT
<213> ORGANISM: Artificial Sequence
<220> FEATURE:
<223> OTHER INFORMATION: synthetic antimicrobial peptide cathelicidin
      (human LL-37)

<400> SEQUENCE: 59

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 60
<211> LENGTH: 23
<212> TYPE: PRT
<213> ORGANISM: Artificial Sequence
<220> FEATURE:
```

<223> OTHER INFORMATION: synthetic antimicrobial peptide clavanin A

<400> SEQUENCE: 60

Val Phe Gln Phe Leu Gly Lys Ile Ile His His Val Gly Asn Phe Val
1               5                   10                  15

His Gly Phe Ser His Val Phe
            20

<210> SEQ ID NO 61
<211> LENGTH: 35
<212> TYPE: PRT
<213> ORGANISM: Artificial Sequence
<220> FEATURE:
<223> OTHER INFORMATION: synthetic antimicrobial peptide cecropin

<400> SEQUENCE: 61

Arg Trp Lys Ile Phe Lys Lys Ile Glu Lys Val Gly Gln Asn Ile Arg
1               5                   10                  15

Asp Gly Ile Val Lys Ala Gly Pro Ala Val Ala Val Val Gly Gln Ala
            20                  25                  30

Ala Thr Ile
        35

<210> SEQ ID NO 62
<211> LENGTH: 12
<212> TYPE: PRT
<213> ORGANISM: Artificial Sequence
<220> FEATURE:
<223> OTHER INFORMATION: synthetic antimicrobial peptide cyclic
      dodecapeptide

<400> SEQUENCE: 62

Arg Ile Cys Arg Ile Ile Phe Leu Arg Val Cys Arg
1               5                   10

<210> SEQ ID NO 63
<211> LENGTH: 38
<212> TYPE: PRT
<213> ORGANISM: Artificial Sequence
<220> FEATURE:
<223> OTHER INFORMATION: synthetic human antimicrobial peptide beta-
      defensin I

<400> SEQUENCE: 63

Asp Phe Ala Ser Cys His Thr Asn Gly Gly Ile Cys Leu Pro Asn Arg
1               5                   10                  15

Cys Pro Gly His Met Ile Gln Ile Gly Ile Cys Phe Arg Pro Arg Val
            20                  25                  30

Lys Cys Cys Arg Ser Trp
        35

<210> SEQ ID NO 64
<211> LENGTH: 30
<212> TYPE: PRT
<213> ORGANISM: Artificial Sequence
<220> FEATURE:
<223> OTHER INFORMATION: synthetic antimicrobial peptide alpha-defensin
      (HNP-1)

<400> SEQUENCE: 64

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 65
<211> LENGTH: 33
<212> TYPE: PRT
<213> ORGANISM: Artificial Sequence
<220> FEATURE:
<223> OTHER INFORMATION: synthetic antimicrobial peptide gaegurin

<400> SEQUENCE: 65

Ser Leu Phe Ser Leu Ile Lys Ala Gly Ala Lys Phe Leu Gly Lys Asn
1               5                   10                  15

Leu Leu Lys Gln Gly Ala Cys Tyr Ala Ala Cys Lys Ala Ser Lys Gln
            20                  25                  30

Cys

<210> SEQ ID NO 66
<211> LENGTH: 38
<212> TYPE: PRT
<213> ORGANISM: Artificial Sequence
<220> FEATURE:
<223> OTHER INFORMATION: synthetic antimicrobial peptide histatin

<400> SEQUENCE: 66

Asp Ser His Glu Glu Arg His His Gly Arg His Gly His His Lys Tyr
1               5                   10                  15

Gly Arg Lys Phe His Glu Lys His His Ser His Arg Gly Tyr Arg Ser
            20                  25                  30

Asn Tyr Leu Tyr Asp Asn
        35

<210> SEQ ID NO 67
<211> LENGTH: 13
<212> TYPE: PRT
<213> ORGANISM: Artificial Sequence
<220> FEATURE:
<223> OTHER INFORMATION: synthetic antimicrobial peptide indolicidin

<400> SEQUENCE: 67

Ile Leu Pro Trp Lys Trp Pro Trp Trp Pro Trp Arg Arg
1               5                   10

<210> SEQ ID NO 68
<211> LENGTH: 23
<212> TYPE: PRT
<213> ORGANISM: Artificial Sequence
<220> FEATURE:
<223> OTHER INFORMATION: synthetic antimicrobial peptide magainin II

<400> SEQUENCE: 68

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 69
<211> LENGTH: 26
<212> TYPE: PRT
<213> ORGANISM: Artificial Sequence
<220> FEATURE:
<223> OTHER INFORMATION: synthetic antimicrobial peptide melittin B

<400> SEQUENCE: 69

Gly Ile Gly Ala Val Leu Lys Val Leu Thr Thr Gly Leu Pro Ala Leu
1               5                   10                  15

```
Ile Ser Trp Ile Lys Arg Lys Arg Gln Gln
            20              25
```

<210> SEQ ID NO 70
<211> LENGTH: 34
<212> TYPE: PRT
<213> ORGANISM: Artificial Sequence
<220> FEATURE:
<223> OTHER INFORMATION: synthetic antimicrobial peptide nisin A

<400> SEQUENCE: 70

```
Ile Thr Ser Ile Ser Leu Cys Thr Pro Gly Cys Lys Thr Gly Ala Leu
 1               5                  10                  15

Met Gly Cys Asn Met Lys Thr Ala Thr Cys His Cys Ser Ile His Val
            20                  25                  30

Ser Lys
```

<210> SEQ ID NO 71
<211> LENGTH: 19
<212> TYPE: PRT
<213> ORGANISM: Artificial Sequence
<220> FEATURE:
<223> OTHER INFORMATION: synthetic antimicrobial peptide ranalexin

<400> SEQUENCE: 71

```
Leu Gly Gly Leu Ile Lys Ile Val Pro Ala Met Ile Cys Ala Val Thr
 1               5                  10                  15

Lys Lys Cys
```

<210> SEQ ID NO 72
<211> LENGTH: 17
<212> TYPE: PRT
<213> ORGANISM: Artificial Sequence
<220> FEATURE:
<223> OTHER INFORMATION: synthetic antimicrobial peptide tachyplesin

<400> SEQUENCE: 72

```
Lys Trp Cys Phe Arg Val Cys Tyr Arg Gly Ile Cys Tyr Arg Arg Cys
 1               5                  10                  15

Arg
```

<210> SEQ ID NO 73
<211> LENGTH: 20
<212> TYPE: PRT
<213> ORGANISM: Artificial Sequence
<220> FEATURE:
<223> OTHER INFORMATION: synthetic amphibian antimicrobial peptide
    maximin H5

<400> SEQUENCE: 73

```
Ile Leu Gly Pro Val Leu Gly Leu Val Ser Asp Thr Leu Asp Asp Val
 1               5                  10                  15

Leu Gly Ile Leu
            20
```

<210> SEQ ID NO 74
<211> LENGTH: 6
<212> TYPE: PRT
<213> ORGANISM: Artificial Sequence
<220> FEATURE:
<223> OTHER INFORMATION: synthetic antimicrobial peptide surfactant
    extract 1

<400> SEQUENCE: 74

Asp Asp Asp Asp Asp Asp
 1               5

<210> SEQ ID NO 75
<211> LENGTH: 47
<212> TYPE: PRT
<213> ORGANISM: Artificial Sequence
<220> FEATURE:
<223> OTHER INFORMATION: synthetic antimicrobial peptide DCD-1

<400> SEQUENCE: 75

Ser Ser Leu Leu Glu Lys Gly Leu Asp Gly Ala Lys Lys Ala Val Gly
 1               5                   10                  15

Gly Leu Gly Lys Leu Gly Lys Asp Ala Val Glu Asp Leu Glu Ser Val
                20                  25                  30

Gly Lys Gly Ala Val His Asp Val Lys Asp Val Leu Asp Ser Val
            35                  40                  45

<210> SEQ ID NO 76
<211> LENGTH: 25
<212> TYPE: PRT
<213> ORGANISM: Artificial Sequence
<220> FEATURE:
<223> OTHER INFORMATION: synthetic antimicrobial peptide SSL-25

<400> SEQUENCE: 76

Ser Ser Leu Leu Glu Lys Gly Leu Asp Gly Ala Lys Lys Ala Val Gly
 1               5                   10                  15

Gly Leu Gly Lys Leu Gly Lys Asp Ala
                20                  25

<210> SEQ ID NO 77
<211> LENGTH: 23
<212> TYPE: PRT
<213> ORGANISM: Artificial Sequence
<220> FEATURE:
<223> OTHER INFORMATION: synthetic antimicrobial peptide SSL-23

<400> SEQUENCE: 77

Ser Ser Leu Leu Glu Lys Gly Leu Asp Gly Ala Lys Lys Ala Val Gly
 1               5                   10                  15

Gly Leu Gly Lys Leu Gly Lys
                20

<210> SEQ ID NO 78
<211> LENGTH: 29
<212> TYPE: PRT
<213> ORGANISM: Artificial Sequence
<220> FEATURE:
<223> OTHER INFORMATION: synthetic antimicrobial peptide dermaseptin DS5

<400> SEQUENCE: 78

Gly Leu Trp Ser Lys Ile Lys Thr Ala Gly Lys Ser Val Ala Lys Ala
 1               5                   10                  15

Ala Ala Lys Ala Ala Val Lys Ala Val Thr Asn Ala Val
                20                  25

<210> SEQ ID NO 79
<211> LENGTH: 42
<212> TYPE: PRT
<213> ORGANISM: Artificial Sequence
<220> FEATURE:
<223> OTHER INFORMATION: synthetic insect antimicrobial peptide moricin

<400> SEQUENCE: 79

Ala Lys Ile Pro Ile Lys Ala Ile Lys Thr Val Gly Lys Ala Val Gly
1               5                   10                  15

Lys Gly Leu Arg Ala Ile Asn Ile Ala Ser Thr Ala Asn Asp Val Phe
            20                  25                  30

Asn Phe Leu Lys Pro Lys Arg Lys Ala
        35                  40

<210> SEQ ID NO 80
<211> LENGTH: 24
<212> TYPE: PRT
<213> ORGANISM: Artificial Sequence
<220> FEATURE:
<223> OTHER INFORMATION: synthetic frog antimicrobial peptide bombinin

<400> SEQUENCE: 80

Gly Ile Gly Ala Leu Ser Ala Lys Gly Ala Leu Lys Gly Leu Ala Lys
1               5                   10                  15

Gly Leu Ala Glu His Phe Ala Asn
            20

<210> SEQ ID NO 81
<211> LENGTH: 25
<212> TYPE: PRT
<213> ORGANISM: Artificial Sequence
<220> FEATURE:
<223> OTHER INFORMATION: synthetic white flounder antimicrobial peptide
      pleurocidin

<400> SEQUENCE: 81

Gly Trp Gly Ser Phe Phe Lys Lys Ala Ala His Val Gly Lys His Val
1               5                   10                  15

Gly Lys Ala Ala Leu His Thr Tyr Leu
            20                  25

<210> SEQ ID NO 82
<211> LENGTH: 29
<212> TYPE: PRT
<213> ORGANISM: Artificial Sequence
<220> FEATURE:
<223> OTHER INFORMATION: synthetic sheep antimicrobial peptide SMAP29

<400> SEQUENCE: 82

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 83
<211> LENGTH: 23
<212> TYPE: PRT
<213> ORGANISM: Artificial Sequence
<220> FEATURE:
<223> OTHER INFORMATION: synthetic pig antimicrobial peptide PMAP-23

<400> SEQUENCE: 83

Arg Ile Ile Asp Leu Leu Trp Arg Val Arg Arg Pro Gln Lys Pro Lys
1               5                   10                  15

Phe Val Thr Val Trp Val Arg
            20

<210> SEQ ID NO 84
<211> LENGTH: 13

```
<212> TYPE: PRT
<213> ORGANISM: Artificial Sequence
<220> FEATURE:
<223> OTHER INFORMATION: synthetic wasp antimicrobial peptide VCP-5h
<220> FEATURE:
<221> NAME/KEY: MOD_RES
<222> LOCATION: (13)...(13)
<223> OTHER INFORMATION: leucinamide

<400> SEQUENCE: 84

Phe Leu Pro Ile Ile Gly Lys Leu Leu Ser Gly Leu Leu
 1               5                  10

<210> SEQ ID NO 85
<211> LENGTH: 34
<212> TYPE: PRT
<213> ORGANISM: Artificial Sequence
<220> FEATURE:
<223> OTHER INFORMATION: synthetic honeybee antimicrobial peptide
      abaecin

<400> SEQUENCE: 85

Tyr Val Pro Leu Pro Asn Val Pro Gln Pro Gly Arg Arg Pro Phe Pro
 1               5                  10                  15

Thr Phe Pro Gly Gln Gly Pro Phe Asn Pro Lys Ile Lys Trp Pro Gln
            20                  25                  30

Gly Tyr

<210> SEQ ID NO 86
<211> LENGTH: 19
<212> TYPE: PRT
<213> ORGANISM: Artificial Sequence
<220> FEATURE:
<223> OTHER INFORMATION: synthetic fruitfly antimicrobial peptide
      drosocin

<400> SEQUENCE: 86

Gly Lys Pro Arg Pro Tyr Ser Pro Arg Pro Thr Ser His Pro Arg Pro
 1               5                  10                  15

Ile Arg Val

<210> SEQ ID NO 87
<211> LENGTH: 20
<212> TYPE: PRT
<213> ORGANISM: Artificial Sequence
<220> FEATURE:
<223> OTHER INFORMATION: synthetic sap-sucker bug antimicrobial peptide
      pyrrohocoricin

<400> SEQUENCE: 87

Val Asp Lys Gly Ser Tyr Leu Pro Arg Pro Thr Pro Pro Arg Pro Ile
 1               5                  10                  15

Tyr Asn Arg Asn
            20

<210> SEQ ID NO 88
<211> LENGTH: 22
<212> TYPE: PRT
<213> ORGANISM: Artificial Sequence
<220> FEATURE:
<223> OTHER INFORMATION: synthetic antimicrobial peptide L-15K-7

<400> SEQUENCE: 88

Lys Leu Leu Lys Leu Leu Leu Lys Leu Leu Lys Leu Leu Leu Lys Leu
 1               5                  10                  15
```

Leu Leu Lys Leu Leu Lys
            20

<210> SEQ ID NO 89
<211> LENGTH: 18
<212> TYPE: PRT
<213> ORGANISM: Artificial Sequence
<220> FEATURE:
<223> OTHER INFORMATION: synthetic antimicrobial peptide KLApep
<220> FEATURE:
<221> NAME/KEY: MOD_RES
<222> LOCATION: (18)...(18)
<223> OTHER INFORMATION: alaninamide

<400> SEQUENCE: 89

Lys Leu Ala Leu Lys Leu Ala Leu Lys Ala Trp Lys Ala Ala Leu Lys
1               5                   10                  15

Leu Ala

<210> SEQ ID NO 90
<211> LENGTH: 23
<212> TYPE: PRT
<213> ORGANISM: Artificial Sequence
<220> FEATURE:
<223> OTHER INFORMATION: synthetic antimicrobial peptide D-2A-21

<400> SEQUENCE: 90

Phe Ala Lys Lys Phe Ala Lys Lys Phe Lys Lys Phe Ala Lys Lys Phe
1               5                   10                  15

Ala Lys Phe Ala Phe Ala Phe
            20

<210> SEQ ID NO 91
<211> LENGTH: 17
<212> TYPE: PRT
<213> ORGANISM: Artificial Sequence
<220> FEATURE:
<223> OTHER INFORMATION: synthetic antimicrobial peptide modelin-1

<400> SEQUENCE: 91

Lys Leu Trp Lys Lys Trp Ala Lys Lys Trp Leu Lys Leu Trp Lys Ala
1               5                   10                  15

Trp

<210> SEQ ID NO 92
<211> LENGTH: 12
<212> TYPE: PRT
<213> ORGANISM: Artificial Sequence
<220> FEATURE:
<223> OTHER INFORMATION: synthetic antimicrobial peptide LARL
<220> FEATURE:
<221> NAME/KEY: MOD_RES
<222> LOCATION: (1)...(1)
<223> OTHER INFORMATION: acetyl-leucine
<220> FEATURE:
<221> NAME/KEY: MOD_RES
<222> LOCATION: (12)...(12)
<223> OTHER INFORMATION: acetyl-leucine

<400> SEQUENCE: 92

Leu Ala Arg Leu Leu Ala Arg Leu Leu Ala Arg Leu
1               5                   10

<210> SEQ ID NO 93
<211> LENGTH: 18
<212> TYPE: PRT
<213> ORGANISM: Artificial Sequence

```
<220> FEATURE:
<223> OTHER INFORMATION: synthetic antimicrobial peptide YLK-P
<220> FEATURE:
<221> NAME/KEY: MOD_RES
<222> LOCATION: (18)...(18)
<223> OTHER INFORMATION: leucinamide

<400> SEQUENCE: 93

Tyr Lys Leu Leu Lys Leu Leu Leu Pro Lys Leu Lys Gly Leu Leu Phe
 1               5                  10                  15
Lys Leu

<210> SEQ ID NO 94
<211> LENGTH: 10
<212> TYPE: PRT
<213> ORGANISM: Artificial Sequence
<220> FEATURE:
<223> OTHER INFORMATION: synthetic antimicrobial peptide KSL2
<220> FEATURE:
<221> NAME/KEY: MOD_RES
<222> LOCATION: (10)...(10)
<223> OTHER INFORMATION: lysinamide

<400> SEQUENCE: 94

Lys Lys Val Val Phe Lys Phe Lys Phe Lys
 1               5                  10

<210> SEQ ID NO 95
<211> LENGTH: 15
<212> TYPE: PRT
<213> ORGANISM: Artificial Sequence
<220> FEATURE:
<223> OTHER INFORMATION: synthetic antimicrobial peptide CAM135
<220> FEATURE:
<221> NAME/KEY: MOD_RES
<222> LOCATION: (15)...(15)
<223> OTHER INFORMATION: leucinamide

<400> SEQUENCE: 95

Gly Trp Arg Leu Ile Lys Lys Ile Leu Arg Val Phe Lys Gly Leu
 1               5                  10                  15

<210> SEQ ID NO 96
<211> LENGTH: 20
<212> TYPE: PRT
<213> ORGANISM: Artificial Sequence
<220> FEATURE:
<223> OTHER INFORMATION: synthetic antimicrobial peptide PGAa
<220> FEATURE:
<221> NAME/KEY: MOD_RES
<222> LOCATION: (20)...(20)
<223> OTHER INFORMATION: alaninamide

<400> SEQUENCE: 96

Gly Ile Leu Ser Lys Leu Gly Lys Ala Leu Lys Lys Ala Ala Lys His
 1               5                  10                  15
Ala Ala Lys Ala
            20

<210> SEQ ID NO 97
<211> LENGTH: 22
<212> TYPE: PRT
<213> ORGANISM: Artificial Sequence
<220> FEATURE:
<223> OTHER INFORMATION: synthetic antimicrobial peptide PGYa
<220> FEATURE:
<221> NAME/KEY: MOD_RES
<222> LOCATION: (22)...(22)
<223> OTHER INFORMATION: tyrosinamide
```

<400> SEQUENCE: 97

Gly Leu Leu Arg Arg Leu Arg Asp Phe Leu Lys Lys Ile Gly Glu Lys
1               5                   10                  15

Phe Lys Lys Ile Gly Tyr
            20